(12) United States Patent
Grasse et al.

(10) Patent No.: US 11,717,346 B2
(45) Date of Patent: Aug. 8, 2023

(54) SYSTEMS AND METHODS FOR MONITORING ENERGY APPLICATION TO DENERVATE A PULMONARY ARTERY

(71) Applicant: Gradient Denervation Technologies SAS, Paris (FR)

(72) Inventors: Martin Grasse, Basel (CH); David Amaoua, Versailles (FR)

(73) Assignee: Gradient Denervation Technologies SAS, Paris (FR)

( * ) Notice: Subject to any disclaimer, the term of this patent is extended or adjusted under 35 U.S.C. 154(b) by 0 days.

(21) Appl. No.: 17/935,881

(22) Filed: Sep. 27, 2022

(65) Prior Publication Data

US 2023/0018991 A1 Jan. 19, 2023

Related U.S. Application Data

(63) Continuation of application No. PCT/IB2022/055854, filed on Jun. 23, 2022.

(30) Foreign Application Priority Data

Jun. 24, 2021 (EP) .................................... 21305873

(51) Int. Cl.
*A61B 18/14* (2006.01)
*A61N 7/02* (2006.01)
(Continued)

(52) U.S. Cl.
CPC ............ *A61B 18/1492* (2013.01); *A61N 7/02* (2013.01); *A61B 2018/0022* (2013.01);
(Continued)

(58) Field of Classification Search
CPC .......... A61B 2018/00404; A61B 2018/00863; A61B 5/02007; A61M 2230/30
See application file for complete search history.

(56) References Cited

U.S. PATENT DOCUMENTS

| 4,955,377 A | 9/1990 | Lennox et al. |
| 6,117,101 A | 9/2000 | Diederich et al. |

(Continued)

FOREIGN PATENT DOCUMENTS

| AU | 2007290727 A1 | 3/2008 |
| EP | 0467422 A2 | 1/1992 |

(Continued)

OTHER PUBLICATIONS

Osorio et al., "Reflex Changes on the Pulmonary and Systemic Pressures Elicited by Stimulation of Baroreceptors in the Pulmonary Artery", Circulation Research, vol. X, pp. 664-667 (Year: 1962).*

(Continued)

*Primary Examiner* — Ronald Hupczey, Jr.
(74) *Attorney, Agent, or Firm* — Eversheds Sutherland (US) LLP; Christopher C. Bolten; Albert K. Heng

(57) ABSTRACT

A catheter system for ablation of tissue around a blood vessel, e.g., the pulmonary artery, to reduce neural activity of nerves surrounding the blood vessel. The catheter system includes an elongate shaft having a proximal portion coupled to a handle, and a distal portion. The distal portion includes a transducer and an expandable anchor, which may be actuated to transition between a collapsed delivery state and an expanded deployed state where the anchor centralizes the transducer within the blood vessel. The transducer may be actuated to emit energy to reduce neural activity of the nerves surrounding the blood vessel. Systems and method are further provided for confirming that neural activity of the nerves surround the blood vessel has been sufficiently reduced.

30 Claims, 44 Drawing Sheets

(51) Int. Cl.
    *A61B 18/00*    (2006.01)
    *A61N 7/00*    (2006.01)
(52) U.S. Cl.
    CPC ............... *A61B 2018/00434* (2013.01); *A61B 2018/00577* (2013.01); *A61N 2007/003* (2013.01); *A61N 2007/0091* (2013.01)

(56) References Cited

U.S. PATENT DOCUMENTS

| | | |
|---|---|---|
| 6,292,695 B1 | 9/2001 | Webster, Jr. et al. |
| 6,411,852 B1 | 6/2002 | Danek et al. |
| 6,493,589 B1 | 12/2002 | Medhkour et al. |
| 6,564,096 B2 | 5/2003 | Mest |
| 6,669,655 B1 | 12/2003 | Acker et al. |
| 6,690,971 B2 | 2/2004 | Schauerte et al. |
| 6,763,261 B2 | 7/2004 | Casscells, III et al. |
| 6,763,722 B2 | 7/2004 | Fjield et al. |
| 7,090,648 B2 | 8/2006 | Sackner et al. |
| 7,260,431 B2 | 8/2007 | Libbus et al. |
| 7,269,457 B2 | 9/2007 | Shafer et al. |
| 7,363,076 B2 | 4/2008 | Yun et al. |
| 7,367,951 B2 | 5/2008 | Bennett et al. |
| 7,587,238 B2 | 9/2009 | Moffitt et al. |
| 7,616,990 B2 | 11/2009 | Chavan et al. |
| 7,623,926 B2 | 11/2009 | Rossing et al. |
| 7,630,760 B2 | 12/2009 | Libbus et al. |
| 7,664,548 B2 | 2/2010 | Amurthur et al. |
| 7,711,430 B2 | 5/2010 | Errico et al. |
| 7,715,915 B1 | 5/2010 | Ryu et al. |
| 7,734,355 B2 | 6/2010 | Cohen et al. |
| 7,744,618 B2 | 6/2010 | Shuros et al. |
| 7,783,353 B2 | 8/2010 | Libbus et al. |
| 7,801,604 B2 | 9/2010 | Brockway et al. |
| 7,826,899 B1 | 11/2010 | Ryu et al. |
| 7,828,795 B2 | 11/2010 | Privitera et al. |
| 7,899,527 B2 | 3/2011 | Yun et al. |
| 7,925,342 B2 | 4/2011 | Amurthur et al. |
| 7,937,147 B2 | 5/2011 | Sih et al. |
| 8,019,435 B2 | 9/2011 | Hastings et al. |
| 8,027,724 B2 | 9/2011 | Wei et al. |
| 8,052,668 B2 | 11/2011 | Sih |
| 8,073,538 B2 | 12/2011 | Peters et al. |
| 8,088,127 B2 | 1/2012 | Mayse et al. |
| 8,249,705 B1 | 8/2012 | Kieval et al. |
| 8,585,601 B2 | 11/2013 | Sverdlik et al. |
| 8,634,921 B2 | 1/2014 | An et al. |
| 8,696,581 B2 | 4/2014 | Sverdlik et al. |
| 8,845,629 B2 | 9/2014 | Demarais et al. |
| 8,936,027 B2 | 1/2015 | Santamore et al. |
| 8,986,342 B2 | 3/2015 | Naghavi et al. |
| 9,005,100 B2 | 4/2015 | Gnanashanmugam et al. |
| 9,028,391 B2 | 5/2015 | Gnanashanmugam et al. |
| 9,028,417 B2 | 5/2015 | Sverdlik et al. |
| 9,179,916 B2 | 11/2015 | Brenneman et al. |
| 9,186,198 B2 | 11/2015 | Demarais et al. |
| 9,326,786 B2 | 5/2016 | Sverdlik et al. |
| 9,566,456 B2 | 2/2017 | Sverdlik et al. |
| 9,700,372 B2 | 7/2017 | Schaer |
| 9,707,034 B2 | 7/2017 | Schaer |
| 9,820,800 B2 | 11/2017 | Chen |
| 9,827,036 B2 | 11/2017 | Chen |
| 9,833,623 B2 | 12/2017 | Gnanashanmugam et al. |
| 9,839,408 B2 | 12/2017 | Roschak et al. |
| 9,872,720 B2 | 1/2018 | Chen |
| 9,918,776 B2 | 3/2018 | Chen |
| 9,943,666 B2 | 4/2018 | Warnking |
| 9,955,970 B2 | 5/2018 | Brenneman et al. |
| 9,981,108 B2 | 5/2018 | Warnking |
| 10,039,901 B2 | 8/2018 | Warnking |
| 10,223,786 B2 | 3/2019 | Dickrell, III et al. |
| 10,230,041 B2 | 3/2019 | Taylor et al. |
| 10,350,440 B2 | 7/2019 | Taylor et al. |
| 10,357,304 B2 | 7/2019 | Sverdlik et al. |
| 10,368,893 B2 | 8/2019 | Sverdlik et al. |
| 10,368,944 B2 | 8/2019 | Schaer |
| 10,456,605 B2 | 10/2019 | Taylor et al. |
| 10,499,937 B2 | 12/2019 | Warnking |
| 10,518,112 B2 | 12/2019 | Gilad |
| 10,568,688 B2 | 2/2020 | Hu et al. |
| 10,638,786 B2 | 5/2020 | Barnes et al. |
| 10,736,692 B2 | 8/2020 | Pilcher et al. |
| 10,842,556 B1 | 11/2020 | Tandri et al. |
| 10,874,454 B2 | 12/2020 | Chen |
| 10,893,809 B2 | 1/2021 | Denney, Jr. et al. |
| 10,933,259 B2 | 3/2021 | Sverdlik et al. |
| 11,007,001 B1 | 5/2021 | Carignan et al. |
| 11,241,267 B2 | 2/2022 | Chen |
| 11,318,331 B2 | 5/2022 | Shabtay et al. |
| 2001/0031987 A1 | 10/2001 | Saksena et al. |
| 2003/0216792 A1 | 11/2003 | Levin et al. |
| 2004/0019349 A1 | 1/2004 | Fuimaono et al. |
| 2004/0082859 A1 | 4/2004 | Schaer |
| 2005/0251127 A1 | 11/2005 | Brosch et al. |
| 2005/0261672 A1 | 11/2005 | Deem et al. |
| 2005/0283148 A1 | 12/2005 | Janssen et al. |
| 2006/0041277 A1 | 2/2006 | Deem et al. |
| 2006/0116737 A1 | 6/2006 | Libbus |
| 2006/0167498 A1 | 7/2006 | DiLorenzo |
| 2006/0217772 A1 | 9/2006 | Libbus et al. |
| 2007/0129720 A1 | 6/2007 | Demarais et al. |
| 2007/0129760 A1 | 6/2007 | Demarais et al. |
| 2007/0142879 A1 | 6/2007 | Greenberg et al. |
| 2007/0191904 A1 | 8/2007 | Libbus et al. |
| 2007/0255379 A1 | 11/2007 | Williams et al. |
| 2008/0255642 A1 | 10/2008 | Zarins et al. |
| 2008/0306570 A1 | 12/2008 | Rezai et al. |
| 2009/0024124 A1 | 1/2009 | Lefler et al. |
| 2009/0062873 A1 | 3/2009 | Wu et al. |
| 2009/0118780 A1 | 5/2009 | DiLorenzo |
| 2009/0177262 A1 | 7/2009 | Oberti et al. |
| 2009/0216290 A1 | 8/2009 | Ruse et al. |
| 2009/0254142 A1 | 10/2009 | Edwards et al. |
| 2009/0264741 A1 | 10/2009 | Markowitz et al. |
| 2010/0094196 A1 | 4/2010 | Nash et al. |
| 2010/0113928 A1 | 5/2010 | Thapliyal et al. |
| 2010/0114095 A1 | 5/2010 | Janssen et al. |
| 2010/0137860 A1 | 6/2010 | Demarais et al. |
| 2010/0217347 A1 | 8/2010 | Swoyer et al. |
| 2010/0228317 A1 | 9/2010 | Libbus et al. |
| 2010/0241188 A1 | 9/2010 | Errico et al. |
| 2010/0249773 A1 | 9/2010 | Clark et al. |
| 2010/0249859 A1 | 9/2010 | DiLorenzo |
| 2010/0268307 A1 | 10/2010 | Demarais et al. |
| 2010/0274221 A1 | 10/2010 | Sigg et al. |
| 2010/0286684 A1 | 11/2010 | Hata et al. |
| 2010/0286734 A1 | 11/2010 | Yun et al. |
| 2010/0298905 A1 | 11/2010 | Simon |
| 2011/0118725 A1 | 5/2011 | Mayse et al. |
| 2011/0152855 A1 | 6/2011 | Mayse et al. |
| 2011/0178569 A1 | 7/2011 | Parnis et al. |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0257523 A1 | 10/2011 | Hastings et al. |
| 2011/0257708 A1 | 10/2011 | Kramer et al. |
| 2011/0276103 A1 | 11/2011 | Maile et al. |
| 2011/0301587 A1 | 12/2011 | Deem et al. |
| 2011/0301679 A1 | 12/2011 | Rezai et al. |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0065554 A1 | 3/2012 | Pikus |
| 2012/0123258 A1 | 5/2012 | Willard |
| 2012/0123406 A1 | 5/2012 | Edmunds et al. |
| 2012/0143097 A1 | 6/2012 | Pike, Jr. |
| 2012/0143294 A1 | 6/2012 | Clark et al. |
| 2012/0157992 A1 | 6/2012 | Smith et al. |
| 2012/0157993 A1 | 6/2012 | Jenson et al. |
| 2012/0158104 A1 | 6/2012 | Huynh et al. |
| 2012/0165815 A1 | 6/2012 | Collins et al. |
| 2012/0172680 A1 | 7/2012 | Gelfand et al. |

(56) References Cited

U.S. PATENT DOCUMENTS

| | | |
|---|---|---|
| 2012/0172723 A1 | 7/2012 | Gertner |
| 2012/0172870 A1 | 7/2012 | Jenson et al. |
| 2012/0184952 A1 | 7/2012 | Jenson et al. |
| 2012/0232551 A1 | 9/2012 | Swanson et al. |
| 2012/0265227 A1 | 10/2012 | Sverdlik et al. |
| 2012/0277839 A1 | 11/2012 | Kramer et al. |
| 2012/0290024 A1 | 11/2012 | Zhang et al. |
| 2012/0294424 A1 | 11/2012 | Chin et al. |
| 2012/0302909 A1 | 11/2012 | Mayse et al. |
| 2013/0053792 A1 | 2/2013 | Fischell et al. |
| 2013/0204068 A1 | 8/2013 | Gnanashanmugam et al. |
| 2013/0204242 A1 | 8/2013 | Sverdlik et al. |
| 2013/0304062 A1 | 11/2013 | Chan et al. |
| 2014/0005706 A1 | 1/2014 | Gelfand et al. |
| 2014/0012133 A1 | 1/2014 | Sverdlik et al. |
| 2014/0031785 A1 | 1/2014 | Schwagten et al. |
| 2014/0058294 A1 | 2/2014 | Gross et al. |
| 2014/0163540 A1 | 6/2014 | Iyer et al. |
| 2014/0180227 A1 | 6/2014 | Robinson et al. |
| 2014/0180277 A1 | 6/2014 | Chen |
| 2014/0221975 A1 | 8/2014 | Gnanashanmugam et al. |
| 2014/0243809 A1 | 8/2014 | Gelfand et al. |
| 2014/0277033 A1 | 9/2014 | Taylor et al. |
| 2014/0316269 A1 | 10/2014 | Zhang et al. |
| 2014/0358140 A1 | 12/2014 | Emmons et al. |
| 2015/0057599 A1 | 2/2015 | Chen |
| 2015/0141810 A1 | 5/2015 | Weadock |
| 2015/0165244 A1 | 6/2015 | Kardosh et al. |
| 2015/0256592 A1 | 9/2015 | Young et al. |
| 2015/0257779 A1 | 9/2015 | Sinelnikov et al. |
| 2015/0272666 A1 | 10/2015 | Wang |
| 2016/0008058 A1 | 1/2016 | Hu et al. |
| 2016/0113699 A1 | 4/2016 | Sverdlik et al. |
| 2016/0220851 A1 | 8/2016 | Mayse et al. |
| 2016/0302857 A1 | 10/2016 | Rothman et al. |
| 2016/0303381 A1* | 10/2016 | Pierce ............... A61B 18/1815 |
| 2016/0317621 A1 | 11/2016 | Bright |
| 2017/0216032 A1 | 8/2017 | Van Bladel et al. |
| 2017/0348049 A1 | 12/2017 | Vrba et al. |
| 2017/0354461 A1 | 12/2017 | Rothman et al. |
| 2018/0140347 A1 | 5/2018 | Chen |
| 2018/0326227 A1 | 11/2018 | Sverdlik et al. |
| 2018/0360531 A1 | 12/2018 | Holmes, Jr. et al. |
| 2019/0104933 A1 | 4/2019 | Stern et al. |
| 2019/0105104 A1 | 4/2019 | Bertolero et al. |
| 2019/0183372 A1 | 6/2019 | Ruppersberg |
| 2019/0290350 A1 | 9/2019 | Sverdlik et al. |
| 2019/0308003 A1 | 10/2019 | Sverdlik et al. |
| 2019/0343579 A1 | 11/2019 | Tandri et al. |
| 2019/0366130 A1 | 12/2019 | Sverdlik et al. |
| 2020/0038638 A1 | 2/2020 | Gliner |
| 2020/0094080 A1 | 3/2020 | Shabtay et al. |
| 2020/0101270 A1 | 4/2020 | Sutherland |
| 2020/0101328 A1 | 4/2020 | Gilad |
| 2020/0146562 A1 | 5/2020 | Chronos et al. |
| 2020/0179045 A1 | 6/2020 | Levin et al. |
| 2020/0238107 A1 | 7/2020 | Shabtay et al. |
| 2020/0305952 A1 | 10/2020 | Sharma et al. |
| 2020/0368244 A1 | 11/2020 | Shabtay et al. |
| 2021/0178194 A1 | 6/2021 | Sverdlik et al. |
| 2021/0338305 A1 | 11/2021 | Chen |

FOREIGN PATENT DOCUMENTS

| | | |
|---|---|---|
| EP | 1637086 A1 | 3/2006 |
| EP | 2999411 A2 | 3/2016 |
| RU | 2074645 C1 | 3/1997 |
| RU | 2102090 C1 | 1/1998 |
| SU | 1119663 A1 | 10/1984 |
| SU | 1412745 A1 | 7/1988 |
| SU | 1734708 A1 | 5/1992 |
| WO | WO-9301862 A1 | 2/1993 |
| WO | WO-9965561 A1 | 12/1999 |
| WO | WO-2007078997 A2 | 7/2007 |
| WO | WO-2010110785 A1 | 9/2010 |
| WO | WO-2011075328 A1 | 6/2011 |
| WO | WO-2011091069 A1 | 7/2011 |
| WO | WO-2012068268 A2 | 5/2012 |
| WO | WO-2012120495 A2 | 9/2012 |
| WO | WO-2012149341 A1 | 11/2012 |
| WO | WO-2012149511 A2 | 11/2012 |
| WO | WO-2012154800 A1 | 11/2012 |
| WO | WO-2013090848 A1 | 6/2013 |
| WO | WO-2015102951 A2 | 7/2015 |
| WO | WO-2016007851 A1 | 1/2016 |
| WO | WO-2019148094 A1 | 8/2019 |
| WO | WO-2020039442 A1 | 2/2020 |
| WO | WO-2020091125 A1 | 5/2020 |

OTHER PUBLICATIONS

ACCF/AHA 2009 Expert Consensus Document on Pulmonary Hypertension, J. Am. Coll. Cardiology, 53(17):1573-1619 (Apr. 2009).

Banasiak, et al., Normalization of pulmonary hypertension after experimental pulmonary denervation therapy and MitraClip implantation in a patient initially disqualified from heart transplant, Kardiologia Polska (Polish Heart Journal), 78(9):945-946 (2020).

Brace; Radiofrequency and Microwave Ablation of the Liver . . . ; National Institute of Health/NIH Public Access Author Manuscript; Curr Probl Diagn Radiol., 38(3); pp. 135-143, doi:10.1067, 2009.

Breitling, et al., The pathophysiology of pulmonary hypertension in left heart disease, Am. J. Physiol. Lung Cell Mol. Physiol, 309:L924-L941 (Aug. 2015).

Chen, et al., Pulmonary Artery Denervation: An Alternative Therapy for Pulmonary Hypertension, J. Am. Coll. Cardiol. Intv., 12(7):691-692 (Apr. 2019).

Chernyavskiy, et al., Radiofrequency Pulmonary Artery Ablation For Treatment of Residual Pulmonary Hypertension After Pulmonary Endarterectomy, Kardiologiia, 4:15-21 (Apr. 2018).

Constantine, et al., Pulmonary artery denervation for pulmonary arterial hypertension, Trends in Cardiovascular Medicine, 31(4):252-260 (May 2021).

Cruz et al., Cardiopulmonary Effects Following Endoscopic Thoracic Sympathectom. ; European Journal of Cardio-Toracic Surgery, pp. 491-496, Elsevier B.V., 2009.

Dimopoulos, et al., Pulmonary Artery Denervation: A New, Long-Awaited Interventional Treatment for Combined Pre- and Post-Capillary Pulmonary Hypertension?, J. Am. Coll. Cardiol. Cardiovasc. Interv., 12(3):285-288 (Feb. 2019).

Domingo, et al., Reproducibility of In Vivo Pulmonary Arterial Remodeling Assessment in Stable Pulmonary Arterial Hypertension, J. Am. Coll. Cardiol., 73(9S1):1937 (Mar. 2019).

Ferguson et al., "Effect of Lung Denervation on Pulmonary Hypertension and Edema", Circulation Research, vol. V, pp. 310-314, 1957.

Feshchenko, et al., Cryoablation method for pulmonary artery sympathetic denervation in patients with pulmonary hypertension secondary to left sided heart disease: interventional technique, safety and results of the hospital phase, Russian Journal of Cardiology, 29(8):29-35 (May 2019).

Flues et al., "Cardiac and pulmonary arterial remodeling after sinoaortic denervation in normotensive rates," Autonomic Neuroscience: Basic and Clinical, vol. 166, Issue 1-2, pp. 47-53, 2012.

Garcia-Lunar, et al., Effect of pulmonary artery denervation in postcapillary pulmonary hypertension: results of a randomized controlled study, Basic Research in Cardiology, 114(2):5 (Mar. 2019).

Garutti et al., Surgical Upper Thoracic Sympathectomy Reduces Arterial Oxygenation . . . , Letters to the Editor, p. 703-4, doi; 10.1053/j.jvca.2004.12.008, 2005.

Goncharova, et al., Electrical Stimulation-Guided Approach to Pulmonary Artery Catheter Ablation in Patients With Idiopathic Pulmonary Arterial Hypertension: A Pilot Feasibility Study with a 12-Month Follow-Up, BioMed Research International, Feb. 2020.

Huang, et al., Transthoracic Pulmonary Artery Denervation for Pulmonary Arterial Hypertension, Arteriosclerosis, Thrombosis, and Vascular Biology, 39(4):704-718 (Apr. 2019).

(56) References Cited

OTHER PUBLICATIONS

Hyman, A., Pulmonary Vasoconstriction Due to Nonocclusive Distention of Large Pulmonary Arteries in the Dog, Circulation Research, 23(3):401-413 (Sep. 1968).

Jiang, et al., Sympathetic innervation of canine pulmonary artery and morphometric and functional analysis in dehydromonocrotaline-induced models after pulmonary artery denervation, Interactive Cardiovascular and Thoracic Surgery, 31(5):708-717 (Oct. 2020).

Juratsch, et al., Pulmonary Arterial Hypertension Induced by Distention of the Main Pulmonary Artery in Conscious Newborn, Young, and Adult Sleep, Pediatric Research, 14(12):1332-1338 (Dec. 1980).

Kim, et al., Pulmonary Artery Denervation as an Innovative Treatment for Pulmonary Hypertension With and Without Heart Failure, Cardiology in Review, 29(2):89-95 (Mar. 2021).

Klinger and Frantz, Respiratory Medicine—Diagnosis and Management of Pulmonary Hypertension, Humana Press, 2015.

Le, et al., Pulmonary artery denervation: a novel treatment modality for pulmonary hypertension, J. Thorac. Dis., 11(4):1094-1096 (Apr. 2019).

Leandro, et al., Stimulation mapping of the pulmonary artery for denervation procedures: an experimental study, Journal of Cardiovascular Translational Research, 14(3):546-555 (Jun. 2021).

Naeije et al., "Pulmonary vascular responses to surgical chemodenervation and chemical sympathectomy in dogs," American Physiological Society, pp. 42-50, 1989.

Ntiloudi, et al., Pulmonary arterial hypertension: the case for a bioelectronic treatment, Bioelectronic Medicine, 5(1):1-3 (Dec. 2019).

Ogo, T., Transthoracic Pulmonary Artery Denervation: New Insight Into Autonomic Nervous System in Pulmonary Arterial Hypertension, Arteriosclerosis, Thrombosis, and Vascular Biology, 39(6):979-981 (May 2019).

Osorio, et al., Reflex Changes on the Pulmonary and Systemic Pressures Elicited by Stimulation of Baroreceptors in the Pulmonary Artery, Circulation Research, 10(4):664-667 (Apr. 1962).

Oswald-Mammosser, et al., Prognostic Factors in COPD Patients Receiving Long-term Oxygen Therapy—Importance of Pulmonary Artery Pressure, Chest, 107(5):1193-1198 (May 1995).

Pritzker, M., Zapping the Pulmonary Artery Nerves, Cardiovascular Interventions, 13(8):1000-2 (Apr. 2020).

Razee, et al., Pulmonary Artery Denervation for Pulmonary Hypertension: Recent Updates and Future Perspectives, Trends in Cardiovascular Medicine, 31(4):261-263 (May 2021).

Redfield, et al., Effect of phosphodiesterase-5 inhibition on exercise capacity and clinical status in heart failure with preserved ejection fraction: a randomized clinical trial, JAMA, 309(12):1268-1277 (Mar. 2013).

Romanov, et al., Pulmonary Artery Denervation for Patients With Residual Pulmonary Hypertension After Pulmonary Endarterectomy, Journal of the American College of Cardiology, 76(8):916-926 (Aug. 2020).

Rothman, et al., Intravascular Ultrasound Pulmonary Artery Denervation to Treat Pulmonary Arterial Hypertension (TROPHY1): Multicenter, Early Feasibility Study, JACC: Cardiovascular Interventions, 13(8):989-999 (Apr. 2020).

Savarese, et al., Global Public Health Burden of Heart Failure, Cardiac Failure Review, 3(1):7 (Apr. 2017).

Stone, M.D., Gregg, Pulmonary Artery Denervation (PADN): An Emerging Treatment For Pulmonary Hypertension, Mount Sinai School of Medicine and the Cardiovascular Research Foundation, 2021.

Tendolkar, et al., Review of Advances in Management of Pulmonary Hypertension, Journal of Marine Medical Society, 21(1):9 (Jan. 2019).

Trofimov, et al., Denervation of Pulmonary Arteries in Patients With Mitral Valve Defects Complicated by Atrial Fibrillation and Pulmonary Hypertension, Современные технологии в медицине, 11 (4 (eng)):95-103 (2019).

Yaylali, et al., Will Pulmonary Artery Denervation Really Have a Place in the Armamentarium of the Pulmonary Hypertension Specialist?, J. Am. Coll. Cardiol. Intv., 12(8):799-800 (Apr. 2019).

Zhang, et al., Pulmonary artery denervation improves hemodynamics and cardiac function in pulmonary hypertension secondary to heart failure, Pulmonary Circulation, 9(2):1-12 (Jul. 2019).

Zhang, et al., Pulmonary Artery Denervation Significantly Increases 6-Min Walk Distance for Patients With Combined Pre- and Post-Capillary Pulmonary Hypertension Associated With Left Heart Failure: The PADN-5 Study, Jacc. Cardiovascular Interventions, 12(3):274-284 (Feb. 2019).

Ernst, et al., Anatomy of the Pericardial Space and Mediastinum: Relevance to Epicardial Mapping and Ablation, Cardiac Electrophysiology Clinics, 2(1):1-8 (Mar. 2010).

International Search Report & Written Opinion dated Jan. 2, 2023 in Int'l PCT Patent Appl. Serial No. PCT/IB2022/055854.

\* cited by examiner

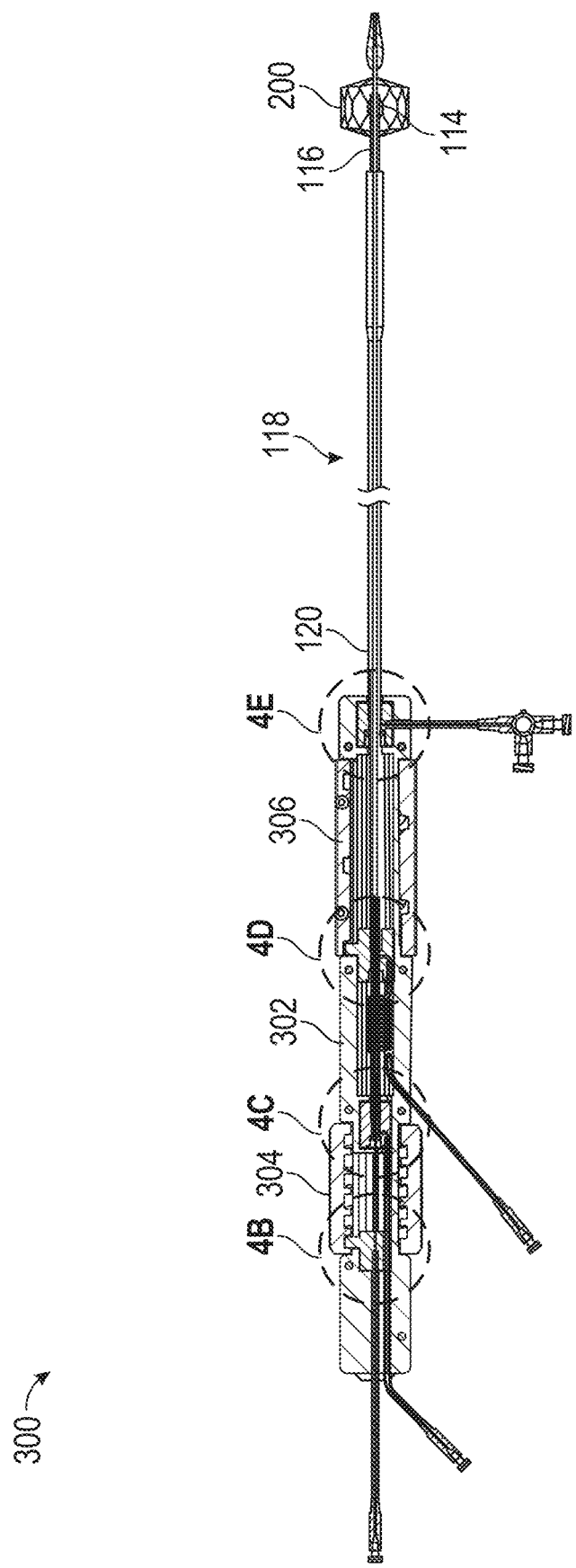

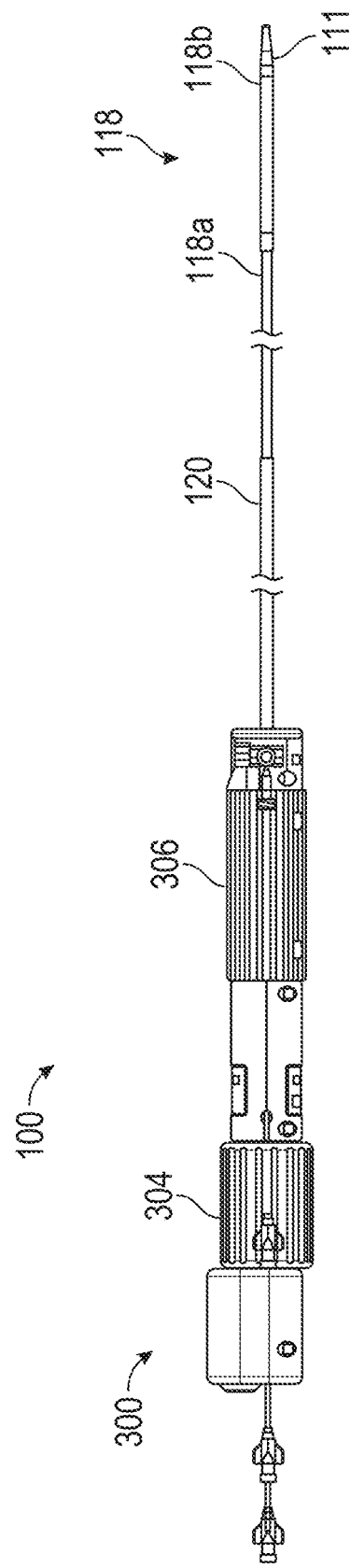
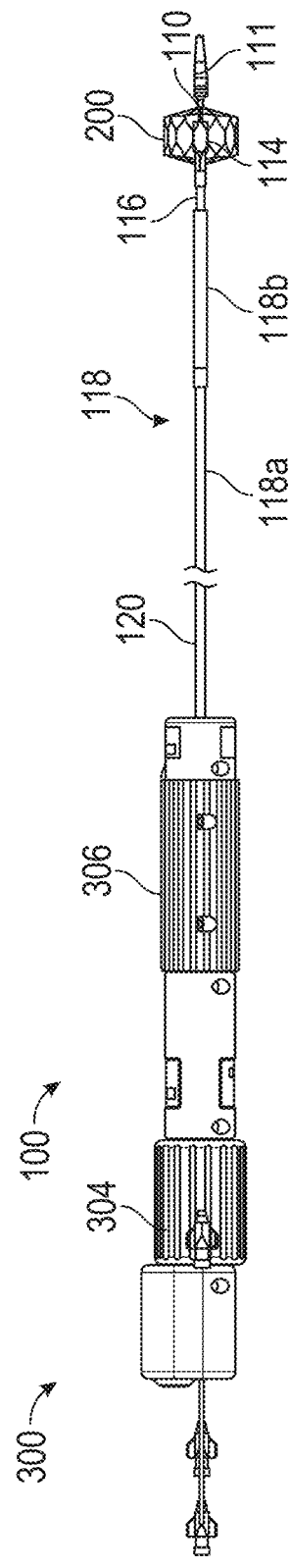
FIG. 5A
FIG. 5B

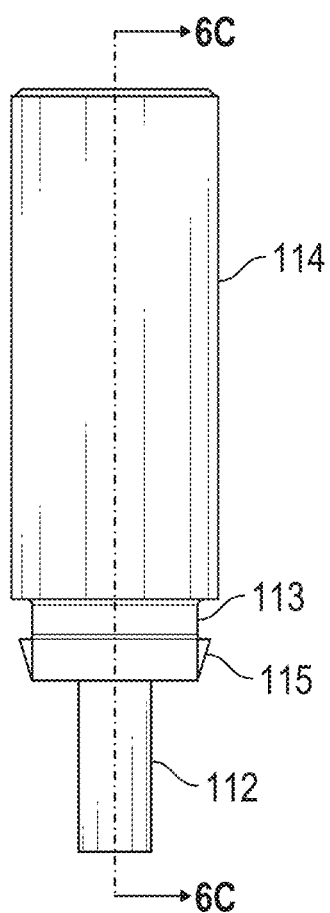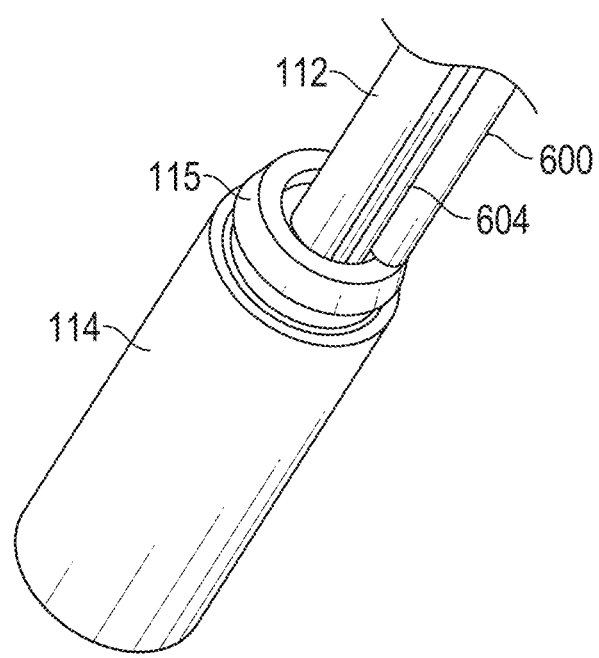
FIG. 6A
FIG. 6B

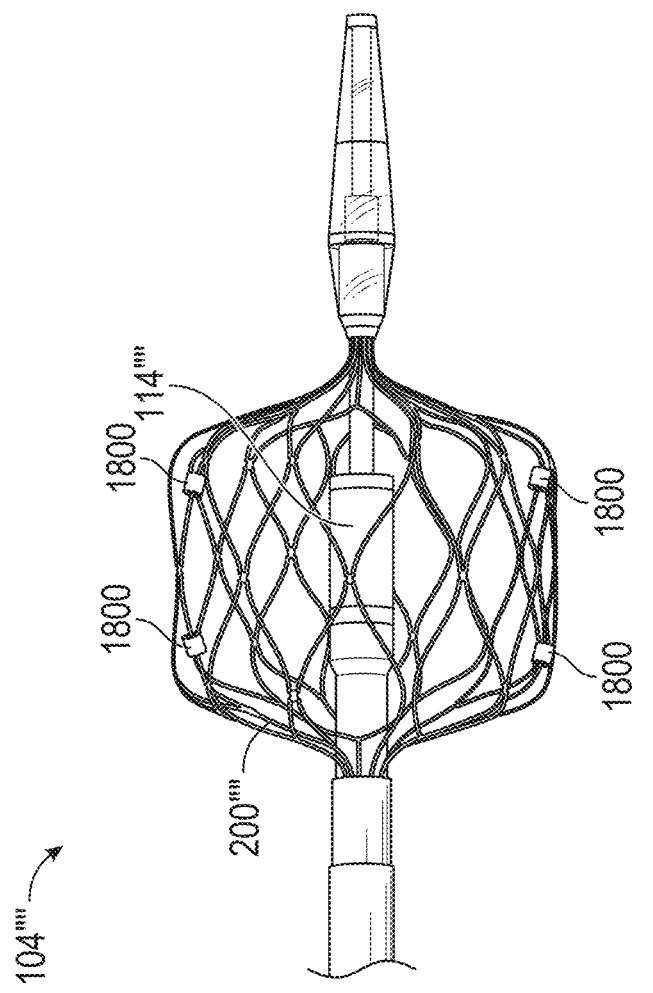

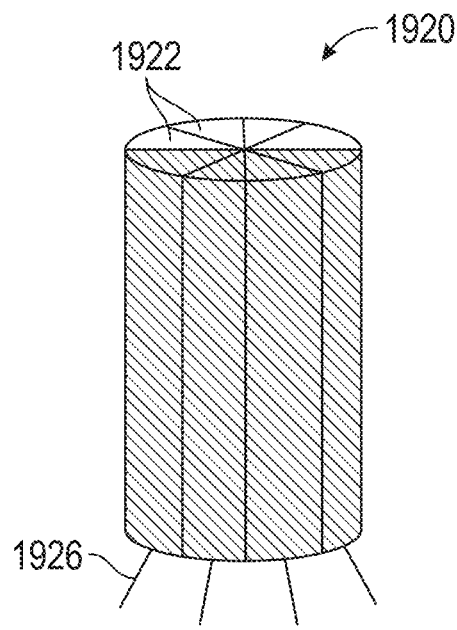
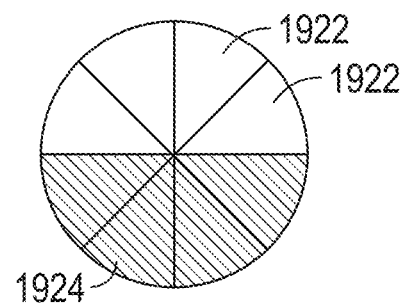
FIG. 19C
FIG. 19D
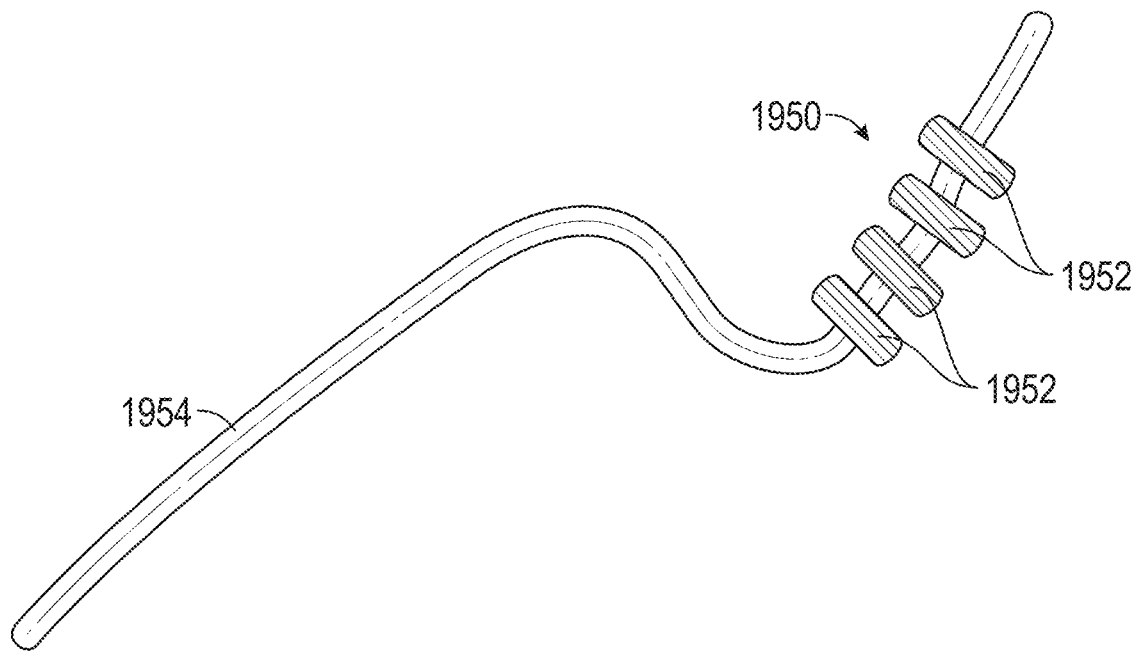
FIG. 19E

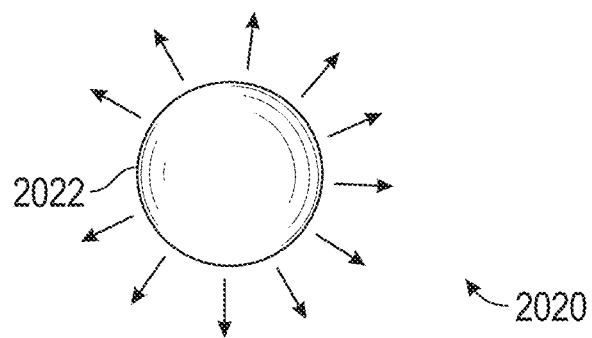
FIG. 20A
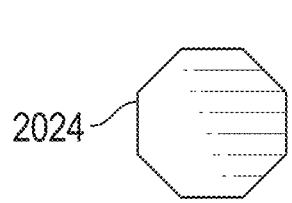 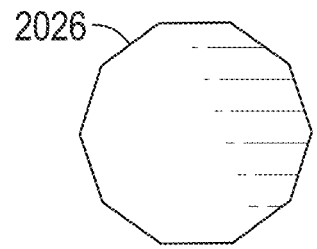 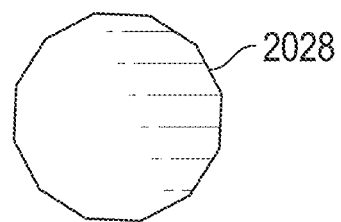
FIG. 20B　　　FIG. 20C　　　FIG. 20D

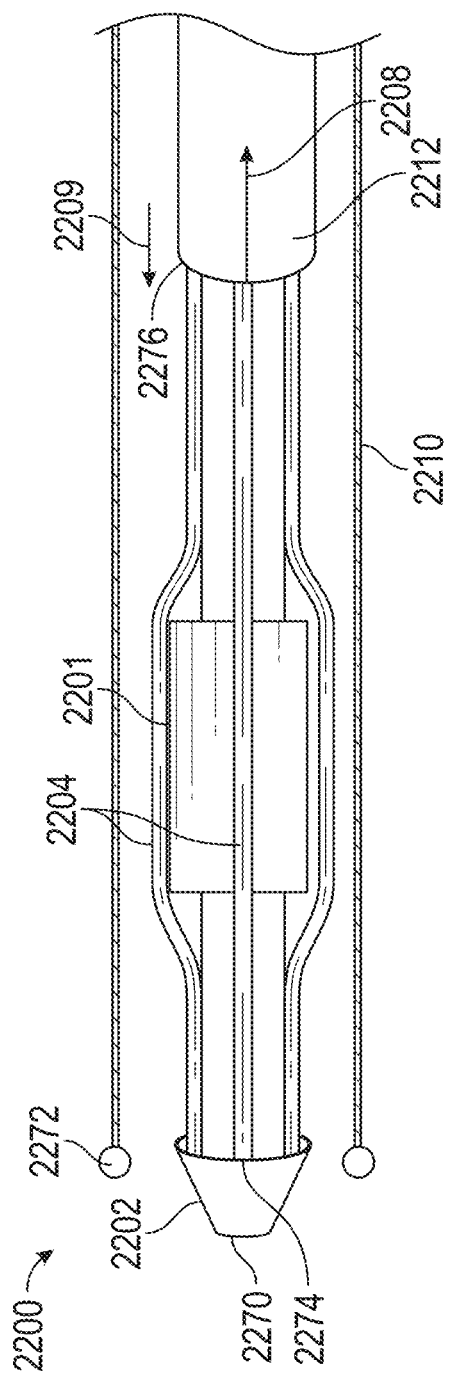
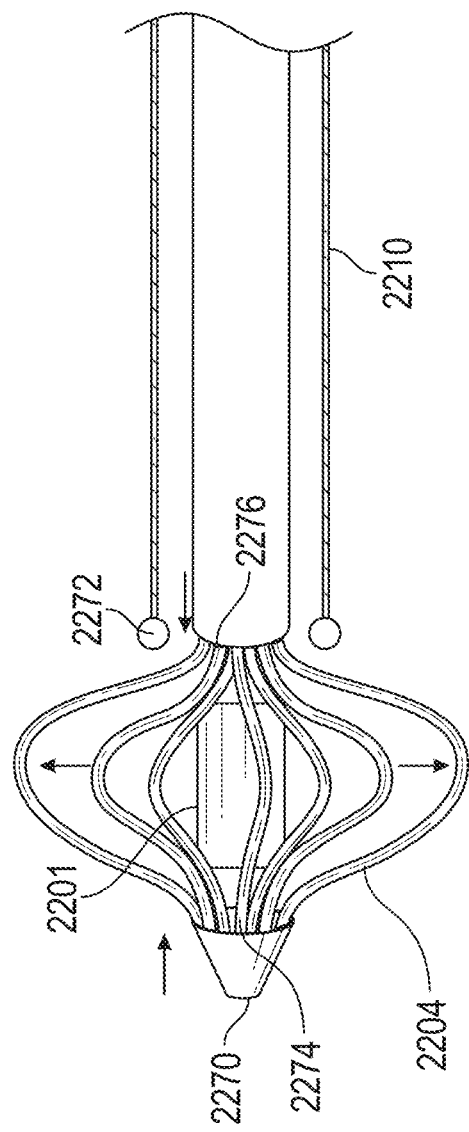
FIG. 22A
FIG. 22B

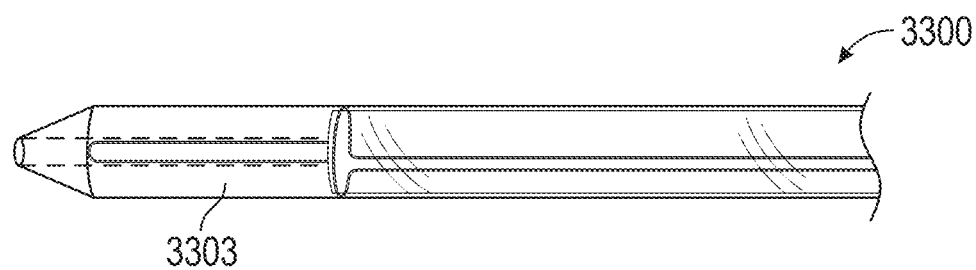
FIG. 33A
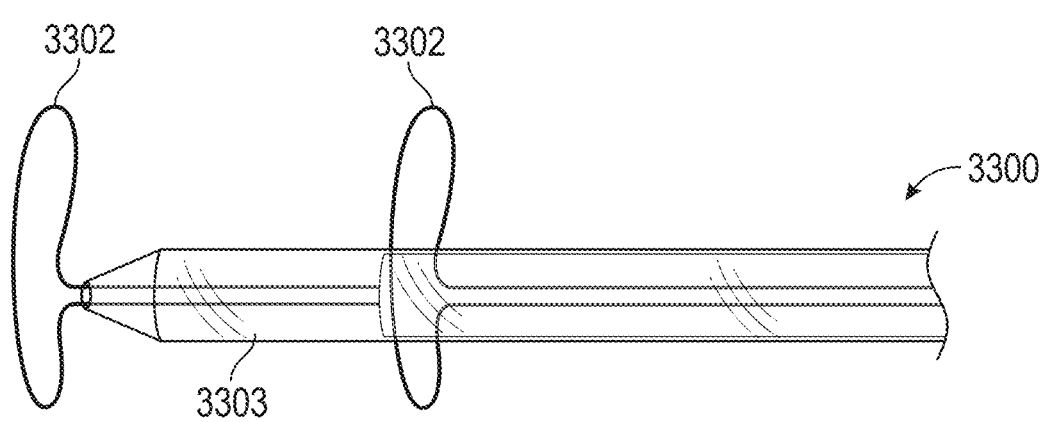
FIG. 33B
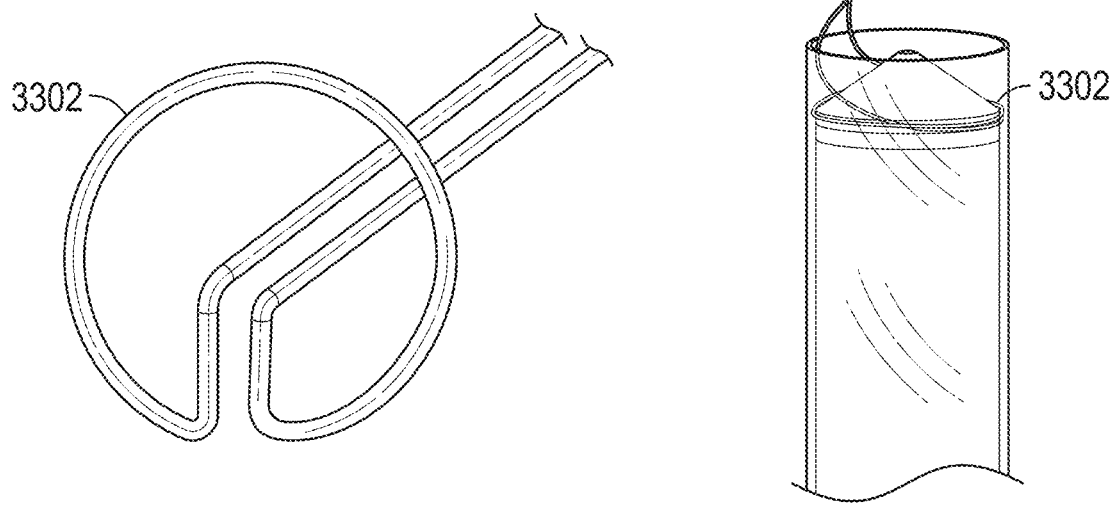
FIG. 33C
FIG. 33D

SYSTEMS AND METHODS FOR MONITORING ENERGY APPLICATION TO DENERVATE A PULMONARY ARTERY

CROSS-REFERENCE TO RELATED APPLICATION

This application is a continuation application of International PCT Patent Appl. No. PCT/IB2022/055854, filed Jun. 23, 2022, which claims priority to EP Patent Appl. No. 21305873.8, filed Jun. 24, 2021, the entire contents of each of which are incorporated herein by reference.

FIELD OF USE

The present disclosure is directed generally to medical devices, systems, and methods for applying energy to reduce neural activity in a blood vessel such as the pulmonary artery to treat pulmonary hypertension and/or other pulmonary vascular disorders.

BACKGROUND

Pulmonary hypertension is a disease phenomenon of multifactorial etiology with high morbidity and mortality. The disease causes increased work for the right side of the heart and eventually hypertrophy and dysfunction of not only the right side of the heart, but often the left side as well. The prognosis of pulmonary hypertension historically has been poor, with median survival historically being less than 3 years. Currently, with the advent of new pharmacologic therapies, survival has improved to 50 to 60% at 5 years. However, many patients continue to progress to worsening stages of pulmonary hypertension, and despite improvements in therapy, prognosis for the condition remains grave.

In view of the foregoing drawbacks of previously known systems and methods, there exists a need for improved systems and methods for treating pulmonary hypertension, particularly minimally invasive treatments that would reduce or negate the need for pharmaceutical remedies, and/or would be permanent or at least long-lasting.

Treatment of pulmonary hypertension via intravascular denervation of the pulmonary artery was first described in U.S. Pat. No. 9,005,100 to Gnanashanmugam, the entire contents of which are incorporated herein by reference. It would be desirable to provide further systems for denervating a blood vessel such as the pulmonary artery, as well as systems for verifying that the denervation has been completed.

SUMMARY

The present disclosure overcomes the drawbacks of previously-known systems and methods for reducing pulmonary hypertension by providing systems and methods for interrupting the nerves (e.g., sympathetic nerves) around and/or innervating the left, right, and/or main pulmonary arteries. Neuromodulation may be accomplished via ablation, denervation, which may or may not be reversible, stimulation, etc. For example, systems disclosed herein are configured to navigate a catheter from a remote insertion point, through the heart, and into the pulmonary branch arteries and trunk. The catheter may include an anchor that, when deployed, will anchor and centralize a transducer within the vessel wall at a target ablation site. Once the nerves located at the ablation site have been ablated, the anchor may be collapsed, and the transducer may be repositioned at another ablation site within the vessel. This deploy, ablate, collapse, and move method may be repeated until both pulmonary artery branches and the pulmonary trunk have been ablated.

In accordance with one aspect of the present disclosure, a system for reducing neural activity of nerves around a blood vessel of a patient is provided. The system may include a handle, an inner catheter, a transducer assembly, an outer catheter, an expandable anchor, and a sheath. For example, the inner catheter may include a guidewire lumen extending through at least a portion of a length of the inner catheter, and a proximal region of the inner catheter operatively coupled to the handle. The transducer assembly may include a transducer shaft having an ultrasound transducer coupled thereto. The ultrasound transducer may be actuated to emit ultrasonic energy within the blood vessel to reduce neural activity of nerves around the blood vessel. The transducer shaft may include a lumen sized and shaped to slidably receive the inner catheter therein, and a proximal region operatively coupled to the handle. The outer catheter may include a lumen sized and shaped to receive the transducer shaft therein, and a proximal region operatively coupled to the handle. The expandable anchor may include a distal end coupled to the inner catheter and a proximal end coupled to the outer catheter such that relative movement between the inner catheter and the outer catheter causes the expandable anchor to transition between a collapsed delivery state and an expanded deployed state. Moreover, the expandable anchor may centralize the ultrasound transducer within the blood vessel of the patient in the expanded deployed state. The sheath may include a lumen sized and shaped to slidably receive the outer catheter and the expandable anchor in the collapsed delivery state therein. A distal region of the sheath may have a stiffness sufficient to facilitate transitioning of the expandable anchor from the expanded deployed state to the collapsed delivery state upon movement of the distal region of the sheath relative to the expandable anchor without buckling the distal region of the sheath, and a proximal region of the sheath operatively coupled to the handle. The blood vessel may be a pulmonary artery and the ultrasound transducer may be actuated to emit ultrasonic energy within the pulmonary artery to reduce neural activity of nerves around the pulmonary artery to treat pulmonary hypertension.

The system further may include a separation sleeve having a lumen sized and shaped to slidably receive the sheath therein, and a proximal region of the separation sleeve fixedly coupled to the handle. In addition, the system may include an introducer having a lumen sized and shaped to slidably receive the sheath and the separation sleeve therein. For example, the introducer may be fixed relative to the patient and actuated to prevent relative movement between the separation sleeve and the introducer, such that the sheath is movable relative to the separation sleeve without relative movement between the transducer assembly and the patient. Moreover, the introducer may include a valve disposed within the lumen of the introducer, such that the introducer may be actuated to prevent relative movement between the separation sleeve and the introducer by actuating the valve against the separation sleeve when the separation sleeve is disposed within the lumen of the introducer.

A distal end of the inner catheter may include an atraumatic tip. For example, the atraumatic tip may include a tapered profile, such that a cross-sectional area of the atraumatic tip decreases from a proximal end of the atraumatic tip toward a distal end of the atraumatic tip. In a delivery configuration, a distal end of the sheath abuts the atraumatic tip. Moreover, the distal end of the expandable anchor may be coupled to the inner catheter via a ring slidably disposed on the inner catheter, such that the distal end of the expandable anchor is slidably coupled to the inner catheter. The outer catheter may be fixedly coupled to the handle, and the inner catheter may be actuated to move relative to the outer catheter to cause the expandable anchor to transition between the collapsed delivery state and the expanded deployed state. Alternatively, the inner catheter may be fixedly coupled to the handle, and the outer catheter may be actuated to move relative to the inner catheter to cause the expandable anchor to transition between the collapsed delivery state and the expanded deployed state.

The expandable anchor may include a plurality of struts, e.g., a plurality of diamond-shaped struts. The expandable anchor may be formed of a shape-memory material. Moreover, the expandable anchor may have a radial force in the expanded deployed state that is greater than a stiffness force of the inner catheter, the transducer shaft, the outer catheter, and the distal region of the sheath. In addition, the stiffness of the distal region of the sheath may be greater than a stiffness of the proximal region of the sheath. An outer diameter of the distal region of the sheath may be larger than an outer diameter of the proximal region of the sheath. The transducer shaft and the outer catheter may be sealed to create a fluidically sealed cavity therebetween, such that at least one cable may be disposed in the fluidically sealed cavity to provide electrical energy to the ultrasound transducer for emitting the ultrasonic energy.

The system further may include a generator operatively coupled to the ultrasound transducer. The generator may be actuated to provide electrical energy to the ultrasound transducer to cause the ultrasound transducer to emit ultrasonic energy. In addition, the system may include a sensor that may measure temperature of the ultrasound transducer, and the generator may include a control loop programmed to adapt the electric energy provided to the ultrasound transducer if the temperature of the ultrasound transducer exceeds a predetermined threshold. Additionally, the transducer may convert acoustic energy reflected from an adjacent anatomical airway structure to electrical energy, and the generator may include a control loop programmed to stop emission of ultrasonic energy if the electrical energy exceeds a predetermined threshold, wherein the electrical energy is indicative of a level of acoustic energy reflected from the adjacent anatomical airway structure.

The system further may include one or more pacing electrodes disposed on the expandable anchor. The one or more pacing electrodes may be actuated to pace the blood vessel and induce a physiological response from the patient if a phrenic nerve is located around the blood vessel. In addition, the system may include a distension mechanism that may apply a force to an inner wall of the blood vessel sufficient to distend the blood vessel and stimulate baroreceptors within the blood vessel. The distension mechanism may include an expandable member that may be expanded from a collapsed state to an expanded state where the expandable member applies the force to the inner wall of the blood vessel. Alternatively, the distension mechanism may include a torqueing mechanism that may be actuated to bend an elongated shaft of the system within the blood vessel to apply the force to the inner wall of the blood vessel.

Moreover, the system further may include a controller operatively coupled to one or more sensors that may measure pressure within the blood vessel. The controller may be programmed to: receive first pressure information within the blood vessel from the one or more sensors at a first time; receive second pressure information within the blood vessel from the one or more sensors at a second time while the expandable member applies a first force to the inner wall to distend the blood vessel; receive third pressure information within the blood vessel from the one or more sensors at a third time after ultrasonic energy is emitted within the blood vessel via the ultrasound transducer to reduce neural activity of nerves around the blood vessel and while the expandable member applies a second force to the inner wall to distend the blood vessel; and compare the second pressure information to the third pressure information to determine whether the ultrasonic energy has reduced neural activity of the nerves around the blood vessel.

For example, the second pressure information may be indicative of a first pressure gradient between pressure within the blood vessel while the first force is applied to the inner wall to distend the blood vessel and pre-distension pressure within the blood vessel associated with the first pressure information, and the third pressure information may be indicative of a second pressure gradient between pressure within the blood vessel while the second force is applied to the inner wall to distend the blood vessel and pre-distension pressure within the blood vessel associated with the first pressure information. Accordingly, the ultrasonic energy may have reduced neural activity of the nerves around the blood vessel if the comparison of the second and third pressure information indicates that the second pressure gradient is less than the first pressure gradient by more than a predetermined threshold. The system further may include one or more sensors that may measure pressure within the blood vessel.

The system further may include a transducer catheter having a lumen sized and shaped to receive the transducer shaft therein and a proximal region operatively coupled to the handle, such that the transducer catheter slidably disposed within the outer catheter. In this configuration, the transducer shaft and the transducer catheter are sealed to create a fluidically sealed cavity therebetween, such that at least one cable may be disposed in the fluidically sealed cavity to provide electrical energy to the ultrasound transducer for emitting ultrasonic energy.

The handle may be actuated to cause translational movement of the ultrasound transducer relative to the inner catheter and the outer catheter via the transducer shaft and the transducer catheter. At least one of the inner catheter, the outer catheter, and the sheath may include a guidewire port sized and shaped to receive the guidewire therethrough. The system further may include one or more intravascular ultrasound (IVUS) transducers disposed on at least one of the inner catheter distal to the ultrasound transducer, the outer catheter between the ultrasound transducer and the proximal end of the expandable anchor, or the outer catheter proximal to the proximal end of the expandable anchor. The one or more IVUS transducers may generate data for detecting anatomical structures adjacent to the blood vessel within a field of view of the one or more IVUS transducers. The one or more IVUS transducers may include a shield for masking at least a portion of the ultrasonic energy emitted from the one or more IVUS transducers.

In addition, the system may include a torque shaft having a lumen sized and shaped to receive the inner catheter therein and a proximal region operatively coupled to the handle. The torque shaft may be coupled to the ultrasound transducer and may be actuated to cause rotation of the ultrasound transducer relative to the inner catheter. The ultrasound transducer may include a plurality of transducer segments, and each transducer segment of the plurality of transducer segments may be independently actuatable to selectively emit ultrasonic energy.

In accordance with another aspect of the present disclosure, a method for reducing neural activity of nerves around a blood vessel of a patient is provided. The method may include selecting a catheter system include a handle, an inner catheter having a guidewire lumen, a transducer assembly slidably disposed over the inner catheter, an outer catheter disposed over a transducer shaft of the transducer assembly, an expandable anchor having a distal end coupled to the inner catheter and a proximal end coupled to the outer catheter, and a sheath slidably disposed over the outer catheter. The method further may include advancing a distal end of a guidewire to a target location within the blood vessel; advancing the catheter system over a proximal end of the guidewire via the guidewire lumen until an ultrasound transducer of the transducer assembly is in the target location within the blood vessel, the expandable anchor disposed within the sheath in a collapsed delivery state; retracting the sheath to expose the expandable anchor within the blood vessel; moving the inner catheter and the outer catheter relative to each other to cause the expandable anchor to transition from the collapsed delivery state to an expanded deployed state, the expandable anchor centralizing the ultrasound transducer within the blood vessel in the expanded deployed state; actuating the ultrasound transducer to emit ultrasonic energy within the blood vessel to reduce neural activity of nerves around the blood vessel; moving the inner catheter and the outer catheter relative to each other to cause the expandable anchor to transition from the expanded deployed state to the collapsed delivery state; advancing the sheath over the expandable anchor in the collapsed delivery state, a distal region of the sheath having a stiffness sufficient to facilitate transitioning of the expandable anchor from the expanded deployed state to the collapsed delivery state upon movement of the distal region of the sheath relative to the expandable anchor without buckling the distal region of the sheath; and removing the catheter system from the patient.

Advancing the catheter system over the proximal end of the guidewire via the guidewire lumen until the ultrasound transducer is in the target location within the blood vessel may include advancing the catheter system over the proximal end of the guidewire via the guidewire lumen until the ultrasound transducer is in the target location within a pulmonary artery. The method further may include inserting an introducer in a vasculature of the patient such that the introducer is fixed relative to the patient, such that advancing the catheter system over the proximal end of the guidewire includes advancing the catheter system over the proximal end of the guidewire and through the introducer.

In addition, the method may include actuating a valve disposed within a lumen of the introducer against a separation sleeve of the catheter system to prevent relative movement between the separation sleeve and the introducer such that the sheath is movable relative to the separation sleeve without relative movement between the transducer assembly and the patient. Accordingly, the separation sleeve may be slidably disposed over at least a portion of the sheath and fixedly coupled to the handle. The method further may include moving the ultrasound transducer translationally relative to the expandable anchor in the expanded deployed state within the blood vessel.

In addition, the method may include, prior to removing the catheter system from the patient, advancing the catheter system until the ultrasound transducer is in a second target location within another portion of the blood vessel; retracting the sheath to expose the expandable anchor within the another portion of the blood vessel; moving the inner catheter and the outer catheter relative to each other to cause the expandable anchor to transition from the collapsed delivery state to the expanded deployed state within the another portion of the blood vessel; and actuating the ultrasound transducer to emit ultrasonic energy within the another portion of the blood vessel to reduce neural activity of nerves around the another portion of the blood vessel. Actuating the ultrasound transducer to emit ultrasonic energy within the blood vessel may include actuating the ultrasound transducer in accordance with a predetermined actuation regime. The predetermined actuation regime may include predetermined periods of non-ablation between predetermined periods of ablation.

Moreover, the method may include, prior to actuating the ultrasound transducer to emit ultrasonic energy within the blood vessel, pacing the blood vessel via one or more pacing electrodes disposed on the expandable anchor in the expanded deployed state to induce an observable physiological response from the patient if a phrenic nerve is located around the blood vessel; and not actuating the ultrasound transducer to emit ultrasonic energy at the target location within the blood vessel if the physiological response is observed to avoid damaging the phrenic nerve. Additionally, or alternatively, the method may include pacing the blood vessel via one or more pacing electrodes disposed on the expandable anchor in the expanded deployed state to induce an observable physiological response from the patient if a phrenic nerve is located around the blood vessel while ultrasonic energy is emitted within the blood vessel; and stopping emission of ultrasonic energy within the blood vessel if a change in the physiological response observed over time exceeds a predetermined threshold to avoid damaging the phrenic nerve.

In accordance with another aspect of the present invention, another method for reducing neural activity of nerves around a blood vessel of a patient is provided. The method may include measuring first pressure information within the blood vessel; applying a first force to an inner wall of the blood vessel to distend the blood vessel; measuring second pressure information within the blood vessel while the first force is applied to the inner wall to distend the blood vessel; emitting energy via an ablation device positioned within the blood vessel to ablate nerves around the blood vessel; applying a second force to the inner wall of the blood vessel to distend the blood vessel; measuring third pressure information within the blood vessel while the second force is applied to the inner wall to distend the blood vessel; and comparing the second pressure information to the third pressure information to determine whether the emitted energy has reduced neural activity of the nerves around the blood vessel.

The second pressure information may be indicative of a first pressure gradient between pressure within the blood vessel while the first force is applied to the inner wall to distend the blood vessel and pre-distension pressure within the blood vessel associated with the first pressure information, and the third pressure information may be indicative of a second pressure gradient between pressure within the blood vessel while the second force is applied to the inner wall to distend the blood vessel and pre-distension pressure within the blood vessel associated with the first pressure information. The emitted energy may have reduced neural activity of the nerves around the blood vessel if the comparison of the second and third pressure information indicates that the second pressure gradient is less than the first pressure gradient by more than a predetermined threshold.

Additionally or alternatively, the emitted energy may have reduced neural activity of the nerves around the blood vessel if the second pressure gradient is zero.

Applying the first and second force to the inner wall of the blood vessel to distend the blood vessel may include applying a force sufficient to stimulate baroreceptors within the blood vessel. Moreover, applying at least one of the first or second force to the inner wall of the blood vessel to distend the blood vessel may include expanding an expandable member from a collapsed state to an expanded state, the expandable member disposed on a catheter sized and shaped to be positioned within the blood vessel. In the expanded state, the expandable device may not fully occlude blood through the blood vessel. The ablation device may be disposed on the same catheter as the expandable member. Alternatively, the ablation device may be disposed on a second catheter sized and shaped to be positioned within the vessel, such that the second catheter is different from the catheter. Alternatively, applying at least one of the first or second force to the inner wall of the blood vessel to distend the blood vessel may include applying a torque to a catheter shaft to bend the catheter shaft within the blood vessel to apply the force.

If the emitted energy has not reduced neural activity of the nerves around the blood vessel based on the comparison of the second and third pressure information, the method further include: emitting energy via the ablation device positioned within the blood vessel to ablate nerves around the blood vessel; applying a third force to the inner wall of the blood vessel to distend the blood vessel; measuring fourth pressure information within the blood vessel while the third force is applied to the inner wall to distend the blood vessel; and comparing the fourth pressure information to at least one of the second or third pressure information to determine whether the emitted energy has reduced neural activity of the nerves around the blood vessel. Moreover, emitting energy via the ablation device positioned within the blood vessel to ablate nerves around the blood vessel may include emitting at least one of focused ultrasound, unfocused ultrasound, radio frequency, microwave, cryo energy, laser, or pulsed field electroporation. The method further may include deploying an expandable anchor within the vessel to centralize the ablation device within the vessel.

In accordance with another aspect of the present disclosure, another system for reducing neural activity of nerves around a blood vessel of a patient is provided. The system may include a catheter assembly, a distension mechanism, one or more sensors that may measure pressure within the blood vessel, and a controller operatively coupled to the one or more sensors. The catheter assembly may have a proximal region operatively coupled to a handle and a distal region sized and shaped to be positioned within the blood vessel, and the distal region of the catheter assembly may include an ablation device that may be actuated to emit energy within the blood vessel to reduce neural activity of nerves around the blood vessel. The distension mechanism may be actuated to apply a force to an inner wall of the blood vessel sufficient to distend the blood vessel and stimulate baroreceptors within the blood vessel.

The controller may be programmed to: receive first pressure information within the blood vessel from the one or more sensors at a first time; receive second pressure information within the blood vessel from the one or more sensors at a second time while the distension mechanism applies a first force to the inner wall to distend the blood vessel; receive third pressure information within the blood vessel from the one or more sensors at a third time after ultrasonic energy is emitted within the blood vessel via the ultrasound transducer to reduce neural activity of nerves around the blood vessel and while the distension mechanism applies a second force to the inner wall to distend the blood vessel; and compare the second pressure information to the third pressure information to determine whether the ultrasonic energy has reduced neural activity of the nerves around the blood vessel.

The distension mechanism may include an expandable member that may be expanded from a collapsed state to an expanded state to apply the force to the inner wall of the blood vessel. Alternatively, the distension mechanism may include a torqueing mechanism configured to bend a shaft of the catheter assembly within the blood vessel to apply the force to the inner wall of the blood vessel. The system further may include an expandable anchor that may transition between a collapsed delivery state and an expanded deployed state where the expandable anchor centralizes the ablation device within the blood vessel. Moreover, the ablation device may emit at least one of focused ultrasound, unfocused ultrasound, radio frequency, microwave, cryo energy, laser, or pulsed field electroporation.

In accordance with another aspect of the present disclosure, a system for reducing neural activity of nerves around a pulmonary artery of a patient is provided. The system may include a handle, an elongated shaft, an ultrasound transducer, and an expandable anchor. The elongated shaft may have a proximal region operatively coupled to the handle, and a distal region. The ultrasound transducer may be disposed on the distal region of the elongated shaft, and may be actuated to emit ultrasonic energy within the pulmonary artery to reduce neural activity of nerves around the pulmonary artery. The expandable anchor may be disposed on the distal region of the elongated shaft, and may transition between a collapsed delivery state and an expanded deployed state where the expandable anchor centralizes the ultrasound transducer within the pulmonary artery of the patient.

The expandable anchor may include a plurality of struts having rounded edges configured to prevent damage to the pulmonary artery. The system further may include a sheath having a lumen sized and shaped to slidably receive the elongated shaft and the expandable anchor in the collapsed delivery state therein. A distal region of the sheath may have a stiffness sufficient to facilitate transitioning of the expandable anchor from the expanded deployed state to the collapsed delivery state upon movement of the distal region of the sheath relative to the expandable anchor without buckling the distal region of the sheath, and a proximal region of the sheath operatively coupled to the handle. The ultrasound transducer may emit the ultrasonic energy within a main branch of the pulmonary artery, a right branch of the pulmonary artery, or a left branch of the pulmonary artery, or any combination thereof.

BRIEF DESCRIPTION OF THE DRAWINGS

FIG. 5A illustrates the catheter system of FIG. 1A in a delivery configuration.

FIG. 5B illustrates the catheter system of FIG. 1A in a deployed configuration.

FIGS. 6A to 6D are various views of an exemplary transducer assembly constructed in accordance with the principles of the present disclosure.

FIG. 18 illustrates an alternative exemplary catheter system having pacing electrodes in accordance with the principles of the present disclosure.

FIG. 19C illustrates another exemplary transducer constructed in accordance with the principles of the present disclosure.

FIG. 19D illustrates an exemplary transducer connection implementation.

FIG. 19E illustrates another exemplary transducer constructed in accordance with the principles of the present disclosure.

FIGS. 20A to 20D illustrate various outer surface shapes of exemplary transducers.

FIG. 22A illustrates an exemplary anchor in a collapsed delivery state constructed in accordance with the principles of the present disclosure.

FIG. 22B illustrates the anchor of FIG. 22A in a deployed state.

FIG. 31B illustrates the anchor of FIG. 31A in a deployed state.

FIG. 33A illustrates an exemplary anchor in a collapsed delivery state constructed in accordance with the principles of the present disclosure.

FIG. 33B illustrates the anchor of FIG. 33A in a deployed state.

FIGS. 33C and 33D illustrate various views of an exemplary loop wire.

DETAILED DESCRIPTION

Figure 1A:
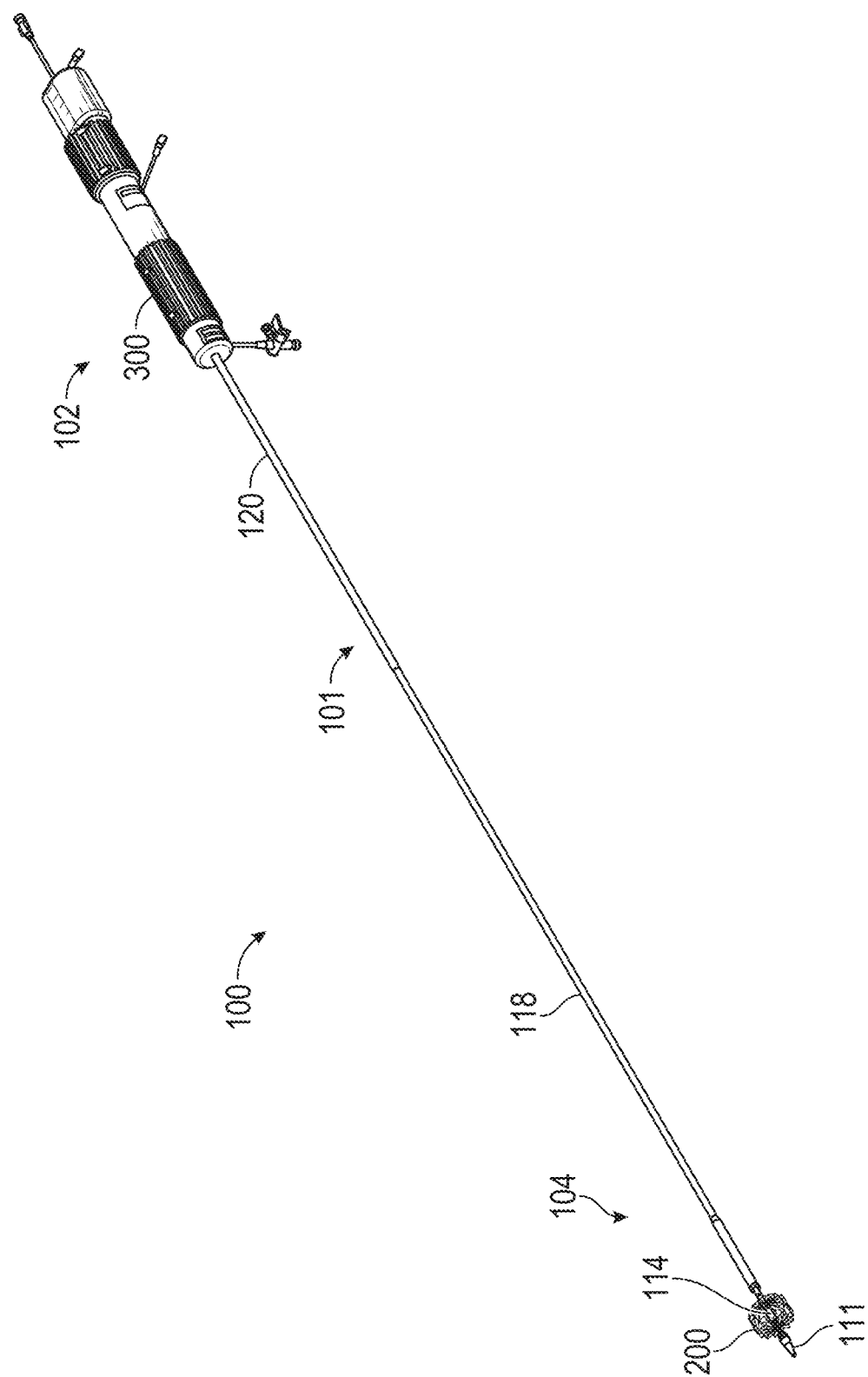
FIG. 1A is a perspective view of an exemplary catheter system for treating tissue constructed in accordance with the principles of the present disclosure.

The interplay of the vasoconstrictive/vasodilator axis of the pulmonary circulation is one of the key determinants of pulmonary hypertension disease progression and severity. The sympathetic nervous system mediates pulmonary vasoconstriction. This may be specifically accomplished by the thoracic sympathetic chain and branches thereof. The sympathetic nervous system may be important in the mediation of the hypoxia mediated vasoconstrictive response of the pulmonary arterial vasculature. Modulating or reducing the sympathetic nervous system activity within the pulmonary vasculature is a unique approach for the treatment of pulmonary hypertension. Reducing, modulating, an/or negating sympathetic tone to the pulmonary arteries reduces sympathetic mediated vasoconstriction, thereby allowing for increased pulmonary vascular diameter and pulmonary vascular dilatation. The end effect of reducing sympathetic tone is a reduction in pulmonary pressure and pulmonary hypertension, a possible goal of therapy.

Although this Detailed Description focuses on treatment of sympathetic nerves, nerve fibers and/or neurons, in any given embodiment, a method, device or system described herein may also or alternatively treat parasympathetic nerves, nerve fibers, and/or neurons. Therefore, descriptions herein of treating sympathetic nervous tissue should not be interpreted as limiting.

Pulmonary Neurovascular Anatomy

The sympathetic innervation of the lung and the heart arises from the thoracolumbar spinal column, ultimately reaching the heart and lung and innervating its vasculature. The sympathetic nervous system is part of the autonomic nervous system, comprising nerve fibers that leave the spinal cord in the thoracic and lumbar regions and supply viscera and blood vessels by way of a chain of sympathetic ganglia running on each side of the spinal column which communicate with the central nervous system via a branch to a corresponding spinal nerve. The sympathetic nerves arising from primarily the thoracic spine (e.g., levels T1-T10 with some potential contribution from the cervical spine) innervate the heart and the lungs after branching out from the thoracic sympathetic chain. The sympathetic nerves converge upon the thoracic sympathetic chain and ganglion, after which arise the post ganglionic sympathetic nerves which then innervate the heart and the lungs. These nerves often converge upon various plexi or plexuses which are areas of convergence often of both sympathetic and parasympathetic nerve fibers. These plexuses then further give rise to nerve branches or continuations, which then branch and ramify onto structures within the heart and lungs or in association with the outer walls of the pulmonary arteries or arterioles for instance. Some of the key plexuses and their anatomic relationship to the heart, lung, and pulmonary vasculature are described herein.

The great plexuses of the sympathetic are aggregations of nerves and ganglia, situated in the thoracic, abdominal, and pelvic cavities, and named the cardiac, celiac, and hypogastric plexuses. They include not only sympathetic fibers derived from the ganglia, but also fibers from the medulla spinalis, which are conveyed through the white rami communicantes. From the plexuses, branches are given to the thoracic, abdominal, and pelvic viscera.

The cardiac plexus is situated at the base of the heart, and is divided into a superficial part, which lies in the concavity of the aortic arch, and a deep part, which is between the aortic arch and the trachea. The superficial and deep parts are closely connected.

The superficial part of the cardiac plexus lies beneath the arch of the aorta, in front of the right pulmonary artery. The superficial part of the cardiac plexus is formed by the superior cardiac branch of the left sympathetic and the lower superior cervical cardiac branch of the left vagus. A small ganglion, the cardiac ganglion of Wrisberg, is occasionally found connected with these nerves at their point of junction. This ganglion, when present, is situated immediately beneath the arch of the aorta, on the right side of the ligamentum arteriosum. The superficial part of the cardiac plexus gives branches (a) to the deep part of the plexus; (b) to the anterior coronary plexus; and (c) to the left anterior pulmonary plexus.

The deep part of the cardiac plexus is situated in front of the bifurcation of the trachea, above the point of division of the pulmonary artery, and behind the aortic arch. The deep part of the cardiac plexus is formed by the cardiac nerves derived from the cervical ganglia of the sympathetic and the cardiac branches of the vagus and recurrent nerves. The only cardiac nerves which do not enter into the formation of the deep part of the cardiac plexus are the superior cardiac nerve of the left sympathetic and the lower of the two superior cervical cardiac branches from the left vagus, which pass to the superficial part of the plexus.

The branches from the right half of the deep part of the cardiac plexus pass, some in front of and others behind, the right pulmonary artery; the branches in front of the pulmonary artery, which are more numerous than the branches behind, transmit a few filaments to the anterior pulmonary plexus, and then continue onward to form part of the anterior coronary plexus; those behind the pulmonary artery distribute a few filaments to the right atrium, and then continue onward to form part of the posterior coronary plexus.

The left half of the deep part of the plexus is connected with the superficial part of the cardiac plexus, and gives filaments to the left atrium, and to the anterior pulmonary plexus, and then continues to form the greater part of the posterior coronary plexus.

The Posterior Coronary Plexus (plexus coronarius posterior; left coronary plexus) is larger than the Anterior Coronary Plexus, and accompanies the left coronary artery. The Posterior Coronary Plexus is chiefly formed by filaments prolonged from the left half of the deep part of the cardiac plexus, and by a few from the right half. The Posterior Coronary Plexus gives branches to the left atrium and ventricle.

The Anterior Coronary Plexus (plexus coronarius anterior; right coronary plexus) is formed partly from the superficial and partly from the deep parts of the cardiac plexus. The Anterior Coronary Plexus accompanies the right coronary artery. The Anterior Coronary Plexus gives branches to the right atrium and ventricle.

The pulmonary plexuses are the sites of convergence of autonomic fibers which supply the lung. The pulmonary plexuses are in continuity with the cardiac plexuses, which lie superiorly, and the oesophageal plexuses, which lie posterosuperiorly.

The pulmonary plexuses are sited anterior and posterior relative to each lung root. The pulmonary plexuses are in close proximity to the pulmonary arteries and, as they branch laterally, the pulmonary plexuses ramify their nerve fibers in association with the outer walls of diverging pulmonary arteries and arterioles.

The passage of fibers from the cardiac plexus is inferiorly, anterior to the trachea and posterior to the aortic arch. The pulmonary plexus also receives autonomic fibers directly from other sources. The pulmonary plexus receives parasympathetic fibers directly from the right vagus nerve, which descends posteroinferiorly on the trachea and divides posterior to the trachea to give pulmonary and oesophageal plexuses; pulmonary plexus passes anteriorly to root of the lung. The pulmonary plexus also receives parasympathetic fibers directly from the left vagus nerve, which descends anteriorly to arch of aorta, gives off recurrent laryngeal branch, and then fibers diverge anteriorly to supply the left pulmonary arterial plexus. The pulmonary plexus receives sympathetic fibers directly from rami of the superior four thoracic ganglia, which pass anteriorly around the posterior thoracic cage to merge on the lateral walls of the esophagus. The rami supply nerve fibers to the pulmonary plexus from the region dorsal to the tracheal bifurcation.

The recurrent cardiac nerve and sometimes the craniovagal cardiac nerves can carry the main innervation of the pulmonary bifurcation and adjacent parts of the main pulmonary artery and its right and left branches. The recurrent cardiac nerve is a moderately large nerve, arising from the right recurrent laryngeal nerve as it loops around the right subclavian artery. The recurrent cardiac nerve usually receives a contribution of varying size from the vagal, parasympathetic trunk, and another from the stellate ganglion. The nerve passes dorsally to the anterior vena cava, laterally to the brachiocephalic artery and arch of the aorta, to the pulmonary bifurcation, to where it divides into anterolateral and posterolateral branches. The anterolateral branch tends to be smaller. The branches then tend to fan out over the anterior and posterior aspects of the main pulmonary artery and communicate with plexi around the right and left pulmonary arteries and the pretracheal plexus. Some fibers continue to the heart and the coronary plexi. During its course, it communicates freely with the cranio-vagal cardiac nerves.

The right vagal cardiac nerves arise from the right vagus trunk caudal to the origin of the right recurrent laryngeal nerve. They fall into two groups, the cranial and caudal vagal cardiac nerves. These vary in size, number, and course. Including some of the smaller divisions, he right vagal cardiac nerves supply branches or twigs to the right pulmonary artery plexus, the antero and posterolateral branches of the right recurrent cardiac nerve at the pulmonary bifurcation, and to the plexus formed by the ventral branch of the vagus, anterior to the pulmonary root, and then terminate in the atrial wall. Small twigs or branches, variable in size and position and sometimes absent, are supplied to the pre-tracheal plexus and the plexus around the right and left pulmonary artery by the right stellate cardiac nerves, the venteromedial cervical cardiac nerve, the left recurrent laryngeal nerve, and the ventral branch of the left vagal trunk. Other twigs or branches are supplied from a diffuse plexiform network of fibers form the ventrolateral cardiac nerve and the left stellate cardiac nerve.

One of these nerves that is of interest is the recurrent cardiac nerve, especially the right recurrent cardiac nerve, as it can contain pre-ganglionic, afferent and sympathetic post-ganglionic fibers among others. The recurrent cardiac nerve is a branch of the right recurrent laryngeal nerve, the nerve of visceral arch. It is therefore of considerable interest that the main nerve supply to the pulmonary bifurcation sensory area, part of the visceral arch, is derived from the recurrent laryngeal nerve, the nerve of visceral arch. As the most cephalic part of the pulmonary artery is formed from the posterior and right lateral parts of the bulbus cordis, this vessel is predominantly supplied from the right visceral nerve.

More specifically, the pulmonary artery bifurcation and adjacent portions of the right and left pulmonary arteries receive a very rich innervation. On the right side, the most constant nerve trunk to the bifurcation is the right recurrent cardiac nerve. The fibers arise from the vagus or the recurrent laryngeal nerve as it loops around the subclavian artery immediately cuadad to its origin from the brachiocephalic trunk. The nerve proceeds medially and caudally passing dorsal to the superior vena cava and lateral to the origin of the brachiocephalic trunk. The fibers ramify at the bifurcation by dividing into antero-lateral and postero-lateral branches which communicate with the fibers from the pulmonary plexuses. During its course it communicates with one or more right vagal cardiac nerves, usually of very small size, and branches from the stellate ganglia or ansa subclavia. These latter branches are thought to contribute the efferent component. Minor variation in the mode of origin from the recurrent laryngeal nerve (RLN) were noted. In some cases, the nerve can arise as a separate trunk from the loop of the RLN and can be joined by a cardiosympathetic branch from the adjacent stellate ganglion. The recurrent cardiac nerve can rarely arise from the angle of origin of the RLN as well. In some cases, the major portion of the nerve can arise from the vagus as the vagal cardiac nerve, also receiving a small filament from the RLN.

The contribution to the innervation of the pulmonary artery from the left side is similar to that of the right, but also receives in some cases invariably a small, direct contribution from the vagus in the form of the ventro-medial-cervical cardiac nerve. This nerve arises from the vagus by a variable number of roots, usually two, and proceeds caudally passing over the aortic arch to ramify over the ligamentum arteriosum, pulmonary bifurcation and left pulmonary artery. The superior cranio vagal root usually receives a direct branch from the left stellate ganglion. The bifurcation and left pulmonary artery receive a small inconstant branch from the RLN as it passes under the aortic arch. In some cases, the descending branches arise from the ascending portion of the RLN to terminate around the bifurcation.

The musculature of the pulmonary artery receives a right sided innervation of predominantly vasoconstrictor adrenergic sympathetic fibers, but little to no motor innervation from the parasympathetics or vagus nerve. The fibers synapse mainly in the stellate, but also in the upper thoracic and sympathetic ganglia. A large concentration of nerve endings are found at the bifurcation of the pulmonary artery, as well as in parts of the adjacent pulmonary artery and its right and left main branches.

Beyond the main pulmonary artery, right main and left main pulmonary arteries, the innervation of the further branches of the lung follows the arterial anatomy, with the nerves coursing along the arteries, typically following a peri-adventitial location or coursing along the adventitia. A rich innervation exists in pulmonary arteries further distal and to pulmonary arterioles as small as 30 microns in diameter or smaller. This innervation includes both parasympathetic and sympathetic innervation, with the lungs considered to have a rich sympathetic nerve supply.

Thoracic sympathectomy is a surgical procedure that currently exists and is utilized in the treatment of a different disease process, namely hyperhidrosis syndrome (excessive sweating). Extensive research on this surgical procedure has shown it to be safe and efficacious. Physiological studies of patients undergoing thoracic sympathectomy have shown mild changes in pulmonary function and mild increases in airway resistance, small decreases in heart rate however preserved left ventricular function and ejection fractions, and also preserved exercise tolerance. Data from T2-T3 video assisted thoracoscopic sympathectomy patients have shown that sympathectomy results in severing the ipsilateral hypoxia mediated vasoconstrictive pathway to the pulmonary vasculature by demonstrating a drop in arterial oxygen saturation during contralateral selective lung ventilation both prior and subsequent to sympathectomy. This implies ipsilateral pulmonary vascular dilatation and reduction in pulmonary pressure. Although thoracic sympathectomy has been used for treating hyperhidrosis, it has not been described, prior to the provisional patent application from which this application claims priority, for treating pulmonary hypertension. More generally, decreasing activity of one or more sympathetic nerves or neurons to reduce pulmonary vascular resistance and/or to ameliorate pulmonary hypertension has not been described previously.

Treatment Devices

Figure 1B:
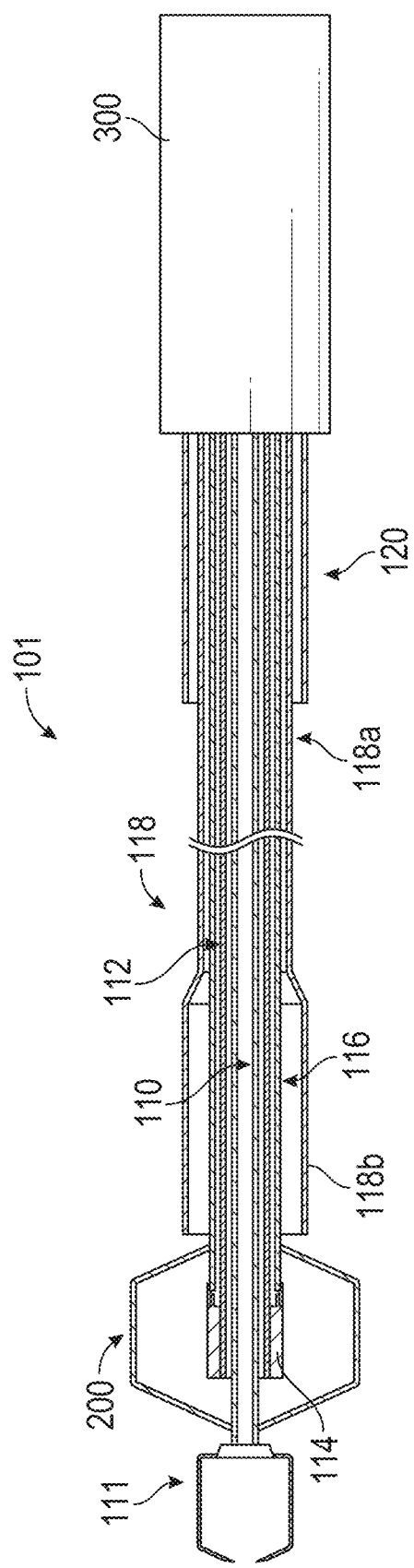
FIG. 1B is a schematic cross-sectional view of the catheter system of FIG. 1A.

Referring now to FIGS. 1A and 1B, an exemplary catheter system for reducing neural activity of nerves around a blood vessel, e.g., a pulmonary artery, of a patient is provided. For example, neural activity may be reduced by inactivating the nerves. Catheter system 100 may include proximal region 102, distal region 104, and elongated shaft 101 extending between proximal region 102 and distal region 104. Catheter system 100 further may include anchor 200 and transducer 114 disposed at distal region 104, and handle 300 disposed at proximal region 102. Handle 300 may be operatively coupled to anchor 200 and transducer 114, e.g., through elongated shaft 101, such that handle 300 may be actuated by a user to actuate anchor 200 and transducer 114. For example, handle 300 may be used to guide distal region 104 to a target location within a blood vessel, and then actuated to deploy anchor 200 within the blood vessel to thereby centralize transducer 114 within the blood vessel. Handle 300 further may be actuated to cause transducer 114 to emit energy to the blood vessel to reduce neural activity of nerves surrounding the blood vessel. Handle 300 also may be used to reposition distal region 104 to another portion of the blood vessel, e.g., from the right pulmonary artery to the left pulmonary artery and/or the main pulmonary artery, such that neural activity of the nerves surrounding the other portion of the blood vessel also may be reduced via transducer 114. Upon completion of the ablation therapy, catheter system 100 may be removed from the patient.

Referring now to FIG. 1B, elongated shaft 101 is described. As shown in FIG. 1B, elongated shaft 101 may include a plurality of catheters, e.g., inner catheter 110, transducer shaft 112, outer catheter 116, sheath 118, and separation sleeve 120. For example, inner catheter 110 may be the innermost catheter of elongated shaft 101, and may have a proximal region operatively coupled to handle 300, and a distal region having atraumatic tip 111. Inner catheter 110 may have a lumen extending therethrough, including through tip 111, such that the lumen is sized and shaped to receive a guidewire therethrough. For example, the guidewire lumen may be between 0.050" and 0.080" along the length of inner catheter 110, and may guide a, e.g., 0.035" guidewire or smaller. Accordingly, a proximal end of a guidewire may be fed through the lumen of tip 111, such that catheter system 100 may be advanced over the guidewire to position distal region 102 within the target location in the blood vessel, as described in further detail below. Inner catheter 110 may be actuatable via handle 300 to move inner catheter 110 translationally relative to handle 300.

Catheter system 100 may include a transducer assembly, which includes transducer shaft 112 having a proximal region operatively coupled to handle 300, and transducer 114 disposed at the distal region of transducer shaft 112. Transducer shaft 112 may have a cylindrical shape, and a lumen extending therethrough, such that the lumen is sized and shaped to slidably receive inner catheter 110 therein. Accordingly, inner catheter 110 may move relative to transducer shaft 112. Transducer 114 may be configured to effect neuromodulation, e.g., via ablation, denervation, which may or may not be reversible, stimulation, etc. For example, transducer 114 may convert electrical input into an acoustic beam that will be absorbed by the target tissue to induce heating of the nerves surrounding/innervating the blood vessel to thereby reduce neural activity of the nerves. For example, transducer 114 may be arcuate ultrasound transducer having a piezoelectric element for emitting ultrasonic energy, e.g., focused or unfocused ultrasound. Alternatively, the transducers described herein may be configured to emit radio frequency (RF) energy, microwave energy, cryo energy, thermal energy, electrical energy, infrared energy, laser energy, phototherapy, plasma energy, ionizing energy, mechanical energy, chemical energy, combinations thereof, and the like.

Outer catheter 116 may have a proximal region operatively coupled to handle 300, and a lumen extending therethrough, such that the lumen is sized and shaped to receive transducer shaft 112 therein. A distal region of outer catheter 116 may be coupled to transducer 114 and transducer shaft 112. For example, the distal region of outer catheter 116 may be sealed with the distal region of transducer shaft 112 to create a fluidically sealed cavity therebetween. Moreover, at least one cable may be disposed in the fluidically sealed cavity and electrically coupled to transducer 114 to provide electrical energy to transducer 114. Outer catheter 116 may be actuatable via handle 300 to move outer catheter 116 translationally relative to handle 300. Accordingly, outer catheter 116 may move relative to inner catheter 110.

As shown in FIG. 1B, a proximal end of anchor 200 may be coupled to outer catheter 116, and a distal end of anchor 200 may be coupled to inner catheter 110. Accordingly, relative movement between inner catheter 110 and outer catheter 116, e.g., via a push-pull mechanism, may cause anchor 200 to transition between a collapsed delivery state and an expanded deployed state. For example, moving inner catheter 110 distally relative to outer catheter 116 may cause anchor 200 to collapse toward the longitudinal axis of elongated shaft 101, and moving inner catheter 110 proximally relative to outer catheter 116 may cause anchor to expand outwardly from the longitudinal axis of elongated shaft 101. In the expanded deployed state, anchor 200 may contact the inner wall of the blood vessel to centralize transducer 114 within the blood vessel. Accordingly, in the expanded deployed state, anchor 200 may have a radial force that is greater than a stiffness force of inner catheter 110, transducer shaft 112, outer catheter 116, and distal region 118b of sheath 118. Anchor 200 may be configured to preserve blood flow through the vessel in the expanded deployed state.

Sheath 118 may have proximal region 118a operatively coupled to handle 300, distal region 118b, and a lumen extending therethrough, such that the lumen is sized and shaped to slidably receive outer catheter 116 and anchor 200 in its collapsed delivery state therein. Proximal region 118a may have a longer and thinner profile than distal region 118b, to reduce the forces of elongated shaft 101 against the patient's anatomy. Reducing this force reduces the amount of force required by anchor 200 to centralize transducer 114. However, this reduction of force of proximal region 118a must be balanced against the stiffness of distal region 118b of sheath 118 required to cover anchor 200. For example, distal region 118b should be stiff enough to slide over anchor 200 without compression nor buckling. This feature may be addressed though the appropriate material selection, the appropriate braid (wire profile & PPI), but also through the preconditioning of sheath 118 before its integration to catheter system 100.

Distal region 118b of sheath 118 may have a stiffness sufficient to facilitate transitioning of anchor 200 from the expanded deployed state to the collapsed delivery state upon movement of distal region 118b distally relative to anchor 200 without buckling distal region 118b. Accordingly, distal region 118b may have a stiffness that is greater than the stiffness of proximal region 118a of sheath 118. For example, as shown in FIG. 1B, distal region 118b may have an outer diameter that is larger than the outer diameter of proximal region 118a, e.g., distal region 118b may have a cross-sectional area that is larger than the cross-sectional area of proximal region 118a. Accordingly, proximal region 118a may have more flexibility to facilitate maneuvering of catheter system 100 through the patient's vasculature. In addition, sheath 118 may be moved distally relative to inner catheter 110 until anchor 200 is disposed within the lumen of sheath 118 in its collapsed delivery state, e.g., within distal region 118b, and the distal end of distal region 118b engages with a proximal end of tip 111, thereby forming a seal, such that catheter system 100 is in a delivery configuration. Accordingly, distal region 118b may have an outer diameter that is substantially equal to the outer diameter of the proximal end of tip 111, to provide a smooth and/or continuous outer surface in the delivery configuration.

Separation sleeve 120 may be fixedly coupled to handle 300, and may have a lumen extending therethrough, such that the lumen is sized and shaped to slidably receive at least proximal region 118a of sheath 118 therein. Accordingly, sheath 118 may move relative to separation sleeve 120, e.g., when sheath 118 is actuated via handle 300. Separation sleeve 120 may extend along at least a portion of the proximal region of elongated shaft 101. Preferably, separation sleeve 120 does not extend along the entire length of elongate shaft 101 so as to provide a smaller footprint and more flexibility of catheter system 100.

Separation sleeve 120 may be configured to permit handle 300 to be fixed relative to the patient. For example, catheter system 100 further may include an introducer, which may be inserted into the patient at an entry site and fixed relative to the patient. The introducer may have a lumen extending therethrough, such that the lumen is sized and shaped to slidably receive elongated shaft 101 therethrough, e.g., in the delivery configuration. For example, tip 111 may be advanced over the guidewire, through the lumen of the introducer, such that elongated shaft 101 is delivered through the patient's vasculature via the introducer. During unsheathing and resheathing of anchor 200 and transducer 114 via proximal and distal translational movement of sheath 118 relative to anchor 200 and transducer 114, it may be desirable to fix the position of handle 300 relative to the patient, such that inadvertent movement of transducer 114 and/or anchor 200 may be avoided as sheath 118 is moved relative to handle 300. Accordingly, separation sleeve 120 may be fixedly coupled to the introducer, which is fixedly coupled to the patient. For example, the transducer may have a valve disposed within its lumen, such that upon actuation thereof, the valve is actuated against separation sleeve 120 when separation sleeve 120 is disposed within the lumen of the introducer. By fixing the position of separation sleeve 120, which is fixedly coupled to handle 300, relative to the introducer, which is fixedly coupled to the patient, handle 300, and accordingly transducer 114 and/or anchor 200, will also be fixed relative to the patient, and accordingly to the blood vessel, such that sheath 118 may be moved proximally and distally relative to transducer 114 and/or anchor 200 while transducer 114 and/or anchor 200 remain unmoved relative to the blood vessel.

Elongated shaft 101 may include additional lumens. For example, an optional lumen may be used to track catheter system 100 over a guidewire. In addition, an optional lumen may provide a passage for conductor wires, e.g., cable 600, between transducer 114 and a signal generating system. Additionally, an optional lumen may provide passage for a conductor wire between a sensor and a receiving station. Moreover, an optional lumen may be provided to deliver coolant to transducer 114 during sonication/ablation. For example, cold saline may be delivered through the lumen, e.g., via a pressure bag or a dedicated infusion pump, and through an outlet located close to the transducer to cool down the transducer and the surrounding blood that is heated by the Joule effect of the transducer.

Figure 2A:
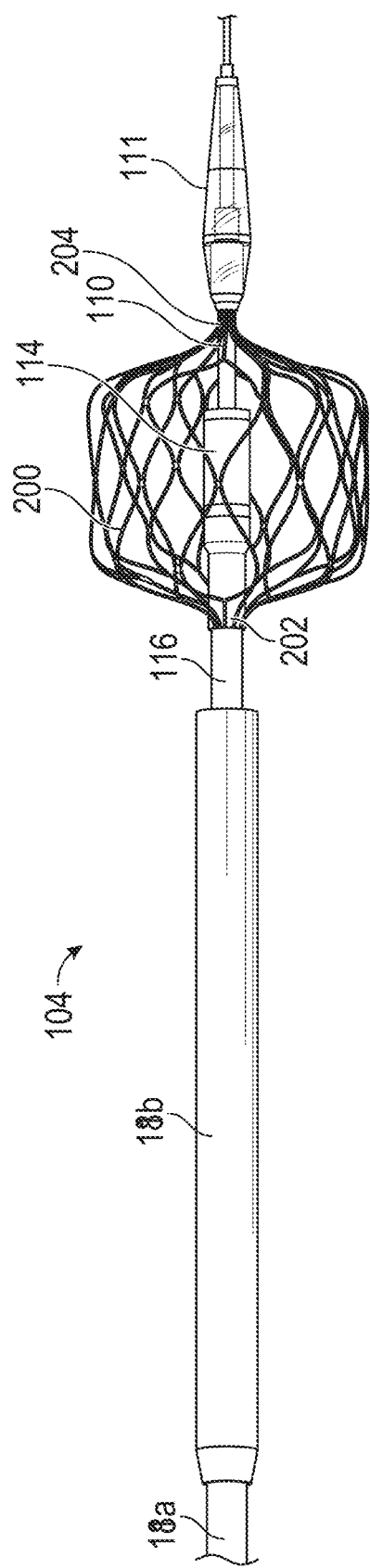
FIG. 2A illustrates the distal region of the catheter system of FIG. 1A.
Figure 2B:
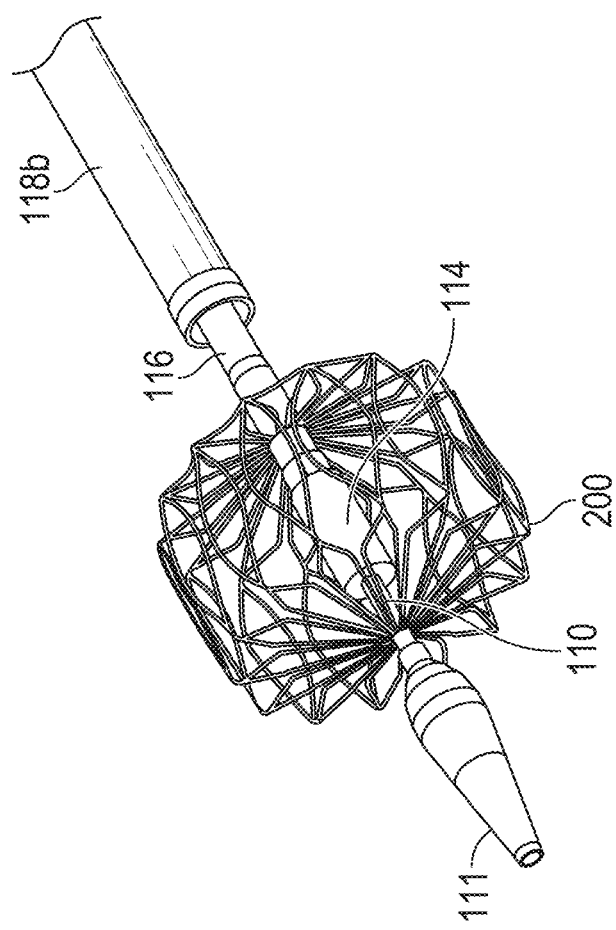
FIG. 2B illustrates an exemplary expandable anchor constructed in accordance with the principles of the present disclosure.
Figure 2C:
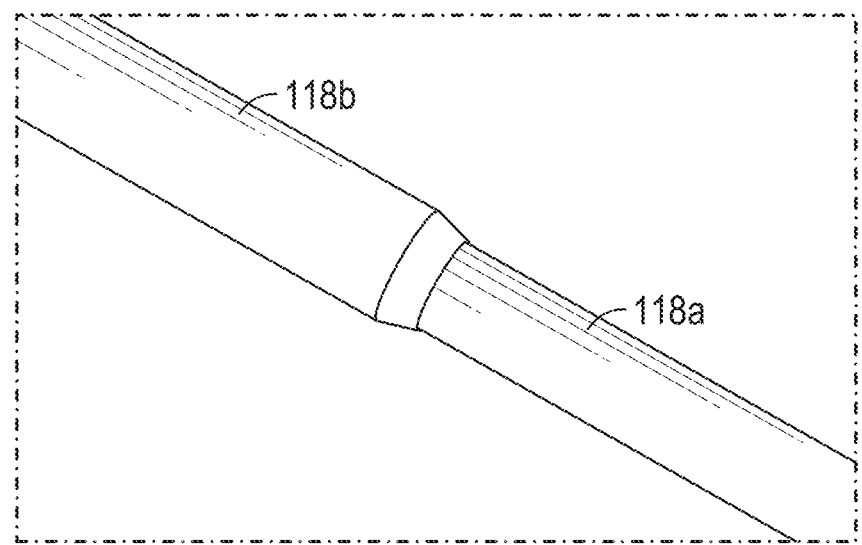
FIG. 2C illustrates an exemplary sheath constructed in accordance with the principles of the present disclosure.

Referring now to FIGS. 2A to 2C, distal region 104 of catheter system 100 is described. Distal region 104 is sized and shaped to be disposed within a blood vessel, e.g., the right, left, and/or main pulmonary arteries. As shown in FIGS. 2A and 2B, proximal end 202 of anchor 200 may be coupled to outer catheter 116 at an axial position proximal to transducer 114, and distal end 204 of anchor 200 may be coupled to inner catheter 110 at an axial position distal to transducer 114, such that transducer 114 is disposed within anchor 200. Anchor 200 may be formed of shape memory material, e.g., Nitinol, chromium cobalt, MP35N, 35NPT, Elgiloy, etc.). As shown in FIGS. 2A and 2B, anchor 200 may be formed of a plurality of struts extending from proximal end 202 to distal end 204 of anchor 200. The plurality of struts may be cut (e.g., laser cut) from a hypotube or sheet. For example, the plurality of struts may include a plurality of connections forming diamond-shaped struts, which form a cage in the expanded deployed state, and prevent grouping of the struts while pushing against the vessel wall. Accordingly, in the expanded deployed state, anchor 200 may centralize transducer 114 within the blood vessel while not occluding the blood vessel, thereby preserving blood flow through the blood vessel.

Anchor 200 is configured to centralize transducer 114 in both a straight or curved blood vessel, which may help ensure that tissue all around the vessel is treated. In a curved vessel, the radial force exerted by anchor 200 on the inner wall of the vessel must be greater than the force inherent from the stiffness of elongated shaft 101 to centralize transducer 114 within the curved vessel. The radial force of anchor 200 is derived from the material composition of anchor 200, e.g., Nitinol, and from the longitudinal compression of anchor 200. Anchor 200 may have a rectangular profile to avoid the plurality of struts slipping over the inner wall of the blood vessel.

As described above, relative movement between inner catheter 110 and outer catheter 116 may cause anchor 200 to transition between a collapsed delivery state and an expanded deployed state. Preferably, outer catheter 116 is fixed relative to handle 300, and inner catheter 110 may be actuated via handle 300 to move proximally and distally relative to outer catheter 116 to expand and collapse anchor 200, as described in further detail below with regard to FIGS. 4B and 4C. Alternatively, inner catheter 110 is fixed relative to handle 300, and outer catheter 116 may be actuated via handle 300 to move proximally and distally relative to outer catheter 116 to expand and collapse anchor 200. In this configuration, outer catheter 116 may be retracted proximally relative to sheath 118 and inner catheter 110 to thereby pull and collapse anchor 200 into sheath 118, e.g., by pulling the proximal end of anchor 200 into sheath 118. In another alternative embodiment, both inner catheter 110 and outer catheter 116 may be actuated via handle 300, e.g., via a single actuator operatively coupled to both inner catheter 110 and outer catheter 116, such that actuation of the single actuator causes inner catheter 110 and outer catheter 116 to move toward and away from each other in equal and opposite directions.

In yet another alternative embodiment, anchor 200 may be formed of a self-expanding material, such that anchor 200 is biased toward the expanded deployed state. Moreover, the distal end of anchor 200 may be coupled to inner catheter 110 via a ring slidably disposed on inner catheter 110, such that the distal end of anchor 200 is slidably coupled to inner catheter 110. Accordingly, upon retraction of sheath 118 to expose anchor 200 within the blood vessel, anchor 200 may self-expand as the ring slides across inner catheter 110 to permit the distal end of anchor 200 to move proximally toward the proximal end of anchor 200. In this configuration, resheathing of anchor 200 via sheath 118 requires less forces because the distal end of anchor 200 is not fixed to inner catheter 110 and sheath 118 does not have to pull the tip/inner material to resheath anchor 200. Additionally, it would allow the use of more flexible material and reduce the forces over the patient anatomy and guide catheter system 100 more easily in small anatomies.

Alternatively, anchor 200 may be formed of a self-expanding material, such that anchor 200 is biased toward the collapsed delivery state. In this configuration, more longitudinal force would be required to move inner catheter 110 and outer catheter 116 toward each other to expand anchor 200; however, distal region 118b would require less stiffness, and therefore may be more flexible as distal region 118b would not need as much stiffness to collapse and cover anchor 200. Moreover, anchor 200 would have less to compete against the stiffness of the elongated shaft 101 to induce centralization of transducer 114. Moreover, the reduction of the profile of the catheter assembly in the section proximal to transducer 114 may prevent or otherwise limit heart straining, and also may limit valve regurgitation while transducer 114 is located in the pulmonary artery, which would be beneficial for a pulmonary hypertension patient as they may only accommodate limited time of heart straining during catheter delivery.

In the expanded deployed state, anchor 200 may have a cross-sectional area that corresponds with the cross-sectional area of the blood vessel, such that anchor 200 applies sufficient force to the inner wall of the blood vessel to secure and centralize transducer 114 within the blood vessel. Preferably, anchor 200 does not distend the blood vessel in the expanded deployed state. Accordingly, relative movement between inner catheter 110 and outer catheter 116 may be selectively actuated via handle 300 to expand anchor 200 to a predetermined size that corresponds with the target vessel.

As further shown in FIGS. 2A and 2B, atraumatic tip 111 may have a tapered profile. For example, the cross-sectional area of tip 111 may decrease from the proximal end of tip 111 toward the distal end of tip 111. The taper profile is gradual to guide distal region 118b of sheath 118 during resheathing of anchor 200 in both a straight line and curved configuration, e.g., in a curved portion of the pulmonary artery. Moreover, the taper ensures there is no gap between tip 111 and distal region 118b in the resheathed delivery configuration to prevent pinching of tissue during resheathing and navigation through the patient's vasculature. Tip 111 may be made of a soft material with a thickness selected to prevent damaging the IVC or SVC, right atrium, right ventricle, valves and pulmonary artery during catheter navigation.

As shown in FIG. 2C, sheath 118 may be a flexible coil, e.g., lasercut stainless steel, to provide sufficient flexibility while limiting compressibility of sheath 118, e.g., to prevent buckling of distal region 118b as sheath 118 is advanced distally relative to anchor 200 to facilitate collapsing of anchor 200 into the lumen of sheath 118. This is beneficial as the femoral access in human constrains the catheter into a 'S' shape, and the smaller the anatomy is, the smaller the bend radii of the two slopes of the 'S' are, leading to maximization of the forces between the catheter and the RA (Right Atrium) or RV (Right Ventricle). These forces may lead to the heart straining which is not favorable for the treatment of a pulmonary hypertension patient. To limit these forces, the stiffness of the catheter may be reduced, which is driven by the stiffness of its stack of shafts. The stiffness of the shaft depends on several properties, such as the raw material or the wall thickness. Moreover, elongated shaft 101 further needs to support the forces of anchor 200 to either collapse or compress anchor 200. Thus, elongated shaft 101 must have limited compressibility, e.g., capped to 2 mm over the course of up to 2 meters of tubing. Accordingly, forming sheath 118, inner catheter 110, and/or outer catheter 116 of a flexible coil, e.g., lasercut stainless steel, may provide sufficient flexibility while limiting compressibility. Alternatively, elongated shaft 101 may be preconditioned in a fixture in a heated environment that forces that compression of elongated shaft 101 before integration in catheter system 100. Accordingly, elongated shaft 101 also may be preconditioned against its elongation.

Figure 3:
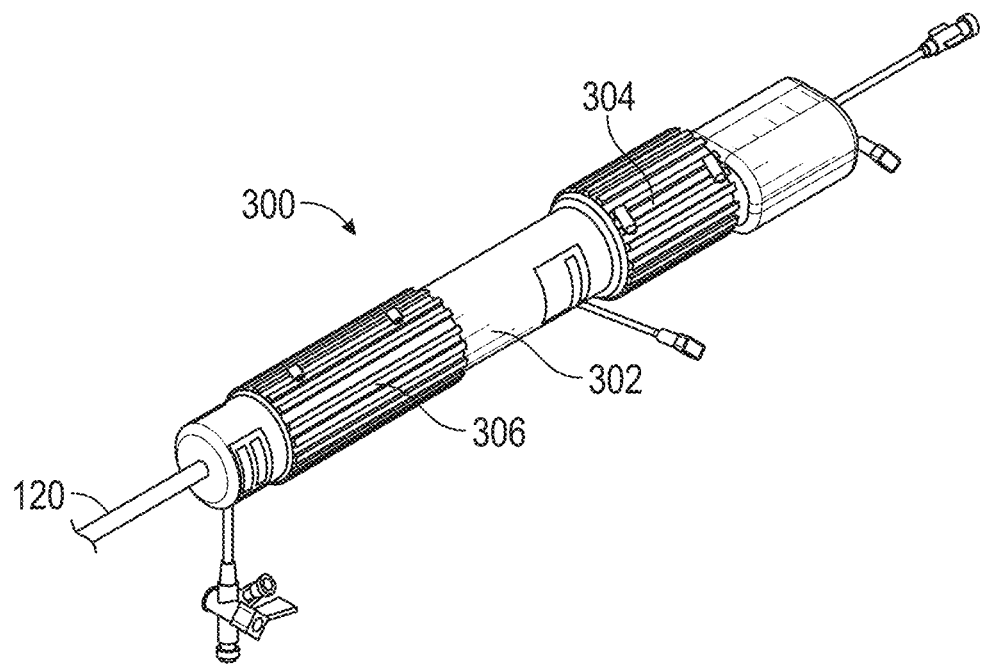
FIG. 3 is a perspective view of an exemplary handle of the catheter system of FIG. 1A constructed in accordance with the principles of the present disclosure.

Referring now to FIG. 3, handle 300 is described. Handle 300 may include frame 302 and one or more actuators, e.g., knob 304 and knob 306, and/or a thumb wheel or slider. Knob 304 may be operatively coupled to at least one of inner catheter 110 or outer catheter 116, and may be configured to be rotated to cause relative movement between inner catheter 110 and outer catheter 116, to thereby transition anchor 200 between the collapsed delivery state and the expanded deployed state. For example, rotating knob 304 in a first direction may cause inner catheter 110 and outer catheter to move toward each other, thereby causing anchor 200 to deploy to the expanded deployed state, and rotating knob 304 in a second direction opposite to the first direction may cause inner catheter 110 and outer catheter 116 to move away from each other, thereby causing anchor 200 to collapse to the collapsed delivery state. As the user actuates knob 304, the user may be able to feel when the struts of anchor 200 contact the vessel wall and may stop expanding anchor 200 at the appropriate deployed state.

Knob 304 may be operatively coupled to only inner catheter 110, such that rotation of knob 304 causes inner catheter 110 to move relative to outer catheter 116. Alternatively, handle 300 may include separate actuators operatively coupled to each of inner catheter 110 and outer catheter 116, such that inner catheter 110 and outer catheter 116 may be independently actuatable.

Knob 306 may be operatively coupled to sheath 118, and may be configured to be rotated to cause movement of sheath 118 relative to handle 300 and the other components of catheter system 100, e.g., anchor 200 and transducer 114, to thereby unsheathe anchor 200 and transducer 114 or resheath anchor 200 and transducer 114. For example, rotating knob 306 in a first direction may cause sheath to retract proximally relative to anchor 200 and transducer 114 to thereby expose anchor 200 and transducer 114, and rotating knob 306 in a second direction opposite to the first direction may cause sheath 118 to move distally relative to anchor 200 and transducer 114 to thereby cover anchor 200 and transducer 114. Knobs 304 and 306 may be selectively actuated together to facilitate collapsing of anchor 200 into the lumen of sheath 118. For example, knob 304 may be rotated to cause inner catheter 110 and outer catheter 116 to move away from each other, thereby causing anchor 200 to collapse to the collapsed delivery state, while knob 306 is simultaneously rotated to move sheath distally relative to anchor 200 to thereby push against anchor 200 and facilitate collapsing of anchor 200 into the lumen of sheath 118.

Figure 4C:
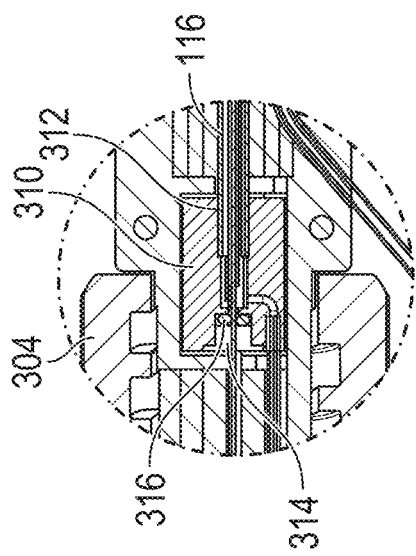
FIG. 4A is a cross-sectional view of the catheter system of FIG. 1A, and FIGS. 4B to 4E are close-up views of the handle of FIG. 4A.
Figure 4E:
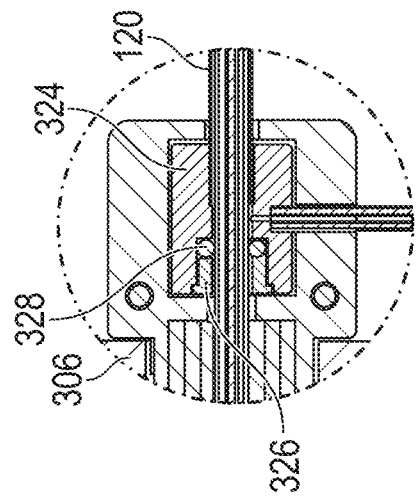
Figure 4B:
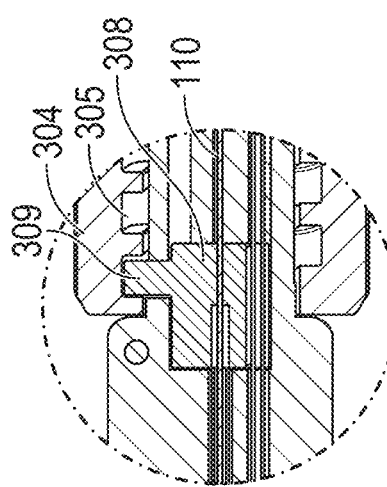
Figure 4D:
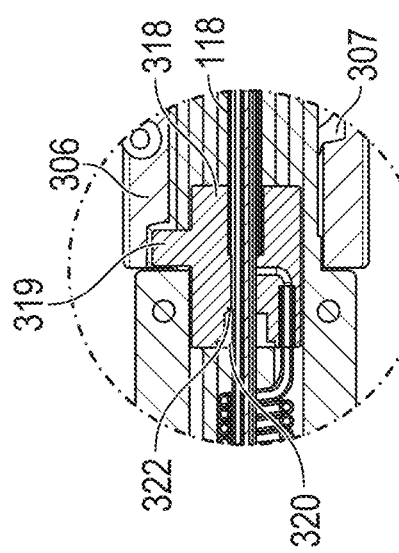

Referring now to FIGS. 4A to 4E, the internal components of handle 300 are provided. FIG. 4A is a cross-sectional view of catheter system 100, and particularly handle 300. FIG. 4B is a close up view of circle 4B of FIG. 4A, FIG. 4C is a close up view of circle 4C of FIG. 4A, FIG. 4D is a close up view of circle 4D of FIG. 4A, and FIG. 4E is a close up view of circle 4E of FIG. 4A. As shown in FIG. 4B, handle 300 may include inner catheter hub 308 operatively coupled to a proximal region of inner catheter 308. Inner catheter hub 308 may be operatively coupled to knob 304, e.g., via protrusion 309 of hub 308 and groove 305 of knob 304, such that as knob 304 is rotated, rotation of groove 305 causes protrusion 309 to move along groove 305, which causes translational movement of hub 318, and accordingly inner catheter 110.

As shown in FIG. 4C, handle 300 may include outer catheter hub 310 operatively coupled to a proximal region of outer catheter 116. Hub 310 may be configured to fixedly coupled outer catheter 116 to handle 300, and may include hub cap 314 and sealing ring 316, e.g., an O-ring, for permitting inner catheter 110 to pass therethrough while sealing the lumen of outer catheter 116.

As shown in FIG. 4D, handle 300 may include sheath hub 318 operatively coupled to a proximal region of sheath 118. Sheath hub 318 may be operatively coupled to knob 306, e.g., via protrusion 319 of hub 318 and groove 307 of knob 306, such that as knob 306 is rotated, rotation of groove 307 causes protrusion 319 to move along groove 307, which causes translational movement of hub 318, and accordingly sheath 118.

As shown in FIG. 4E, handle 300 may include separation sleeve hub 324 operatively coupled to a proximal region of separation sleeve 120. Hub 324 may be configured to fixedly coupled separation sleeve 120 to handle 300, and may include hub cap 326 and sealing ring 328, e.g., an O-ring, for permitting sheath 128 to pass therethrough while sealing the lumen of separation sleeve 120.

Referring now to FIGS. 5A and 5B, the deployment and delivery configurations of catheter system 100 are provided. FIG. 5A illustrates catheter system 100 in a delivery configuration. As shown in FIG. 5A, in the delivery configuration, sheath 118 is advanced distally such that the distal end of distal region 118b of sheath 118 engages with the proximal end of tip 111, and anchor 200 is disposed within the lumen of distal region 118b in its collapsed delivery state. Distal region 104 of catheter system 100 may be advanced to the target location within the blood vessel in the delivery configuration, e.g., through the introducer and over the guidewire.

When distal region 104 is in the target location within the blood vessel, anchor 200 may be ready to be deployed to centralize transducer 114 within the blood vessel, such that transducer 114 may emit energy to provide an ablation therapy. As described above, the introducer may be actuated to fix the position of handle 300 relative to the patient via separation sleeve 120 when transducer 114 is in the target location within the blood vessel. As shown in FIG. 5B, sheath 118 may be retracted proximally relative to anchor 200 and transducer 114, e.g., by rotating knob 306, while anchor 200 and transducer 114 remain stationary relative to the target location within the blood vessel, to thereby expose anchor 200 within the blood vessel. Upon exposure from sheath 118, anchor 200 may remain in a partially or fully collapsed delivery state. For example, anchor 200 may be biased toward the expanded deployed state to facilitate deployment of anchor 200 by the relative movement of inner catheter 110 and outer catheter 116. Accordingly, when anchor 200 is exposed from sheath 118, at least a portion of anchor 200 may begin to self-expand toward the expanded deployed state. Knob 304 may then be rotated to translationally move inner catheter 110 proximally relative to outer catheter 116, to thereby cause anchor 200, which is coupled to both inner catheter 110 and outer catheter 116, to deploy to the expanded deployed state, as shown in FIG. 5B.

With anchor 200 properly deployed within the blood vessel, transducer 114 will be centralized within the blood vessel, and may be actuated to emit energy to the blood vessel to reduce neural activity of the nerves surrounding the blood vessel. When the ablation therapy is complete in the target location within the blood vessel, to reposition transducer 114 to another target location within the blood vessel, e.g., from the left pulmonary artery to the right pulmonary artery and/or the main pulmonary artery, knob 304 may be rotated in the opposite direction to translationally move inner catheter 110 distally relative to outer catheter 116, to thereby cause anchor 200 to transition to the collapsed delivery state. In addition, knob 306 may be simultaneously rotated in the opposite direction to transitionally move sheath 118 distally relative to anchor 200, such that the distal end of distal region 118b of sheath 118 engages with anchor 200 and pushes against anchor 200 to facilitate collapsing of anchor 200 to its collapsed delivery state, until anchor 200 is disposed within the lumen of distal region 118b in the collapsed delivery state.

Alternatively, knob 306 may be rotated to transitionally move sheath 118 distally relative to anchor 200 after inner catheter 110 has been moved distally relative to outer catheter 116, such that anchor 200 is at least partially in its collapsed delivery state. Accordingly, as distal region 118b of sheath 118 moves over anchor 200, anchor 200 will be received within the lumen of distal region 118b in the collapsed delivery state. Sheath 118 may be moved until the distal end of distal region 118b engages with tip 111 in the delivery configuration. Distal region 104 of catheter system 100 may then be repositioned to position transducer 114 in the other target location within the blood vessel, such that anchor 200 may be redeployed and transducer 114 may provide additional ablation therapies. Once all of the ablation therapies are complete, catheter system 100 may be returned to the delivery configuration, and removed from the patient.

Figure 6C:
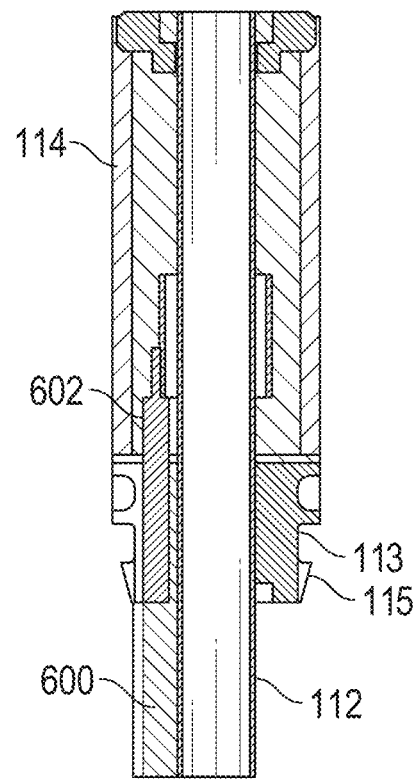

Referring now to FIGS. 6A to 6D, the connection mechanism of outer catheter 116 and the transducer assembly is provided. As shown in FIGS. 6A to 6C, transducer shaft 112 may be coupled to transducer 114. A distal region of transducer shaft 112, proximal to transducer 114, may include one or more barb portions, e.g., barb portion 115. Barb portion 115 may be spaced a predefined distance from the proximal end of transducer 114, thereby defining gap 113. As shown in FIG. 6B, gap 113 and barb portion may extend circumferentially around the distal region of catheter shaft 112. During assembly, outer catheter 116 (not shown) may then be fed over the proximal end of transducer shaft 112 until the distal end of outer catheter 116 passes over barb portion 115 and gap 113 and engages with the proximal end of transducer 114. A material, e.g., epoxy, may be added to fill in the cavity formed between gap 113 and the inner surface of outer catheter 116, such that outer catheter 116 and transducer shaft 112 are sealed to create a fluidically sealed cavity therebetween.

The outer diameter of outer catheter 116 may be substantially equal to the outer diameter of transducer 114, and the inner diameter of the lumen of outer catheter 116 may be larger than the outer diameter of transducer shaft 112, thereby providing a cavity between the inner surface of outer catheter 116 and the outer surface of transducer shaft 112. As described above, this cavity may be fluidically sealed. As shown in FIG. 6C, one or more cables, e.g., cable 600, may be positioned within the fluidically sealed cavity to provide power to transducer 114. For example, as shown in FIG. 6C, cable 600, which may be electrically insulated along almost its entire length, may include conductive portion 602 for electrically coupling with transducer 114.

To limit the heating of the coaxial cable during pulse generation, a larger conductor profile of cable 600 may be selected; however, having a cable with a greater profile would require a larger profile/thicker catheter. Accordingly, instead of a single cable, multiple smaller coaxial cables may be disposed along the length of elongated shaft 101, e.g., within the fluidically sealed cavity, to double the cross-sectional area of the conductor without adding significant thickness to elongated shaft 101.

Figure 6D:
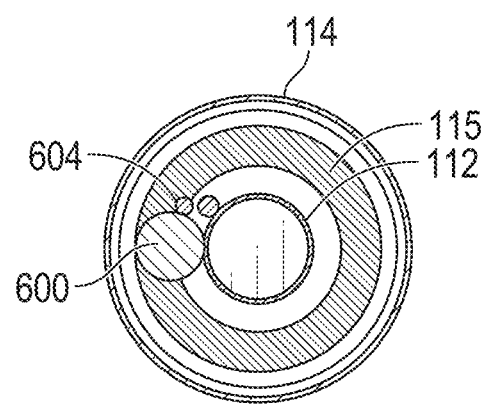

In addition, a pair of thermocouples, e.g., thermocouple 604 also may be positioned within the fluidically sealed cavity. FIG. 6D is a cross-sectional view of the transducer assembly where cable 600 and thermocouple 604 enters the proximal end of barb portion 115 of transducer shaft 112. For example, thermocouple 604 may be a type T thermocouple for monitoring the transducer temperature at the interface with the blood flow. Thermocouple 604 may be located on the inner surface of the copper tape. As the copper and the silver electrode are very good thermal conductors, the temperature measured at this location is representative of the temperature of the transducer's outer surface, without interfering with the acoustic beam, nor adding additional thickness to the transducer assembly build.

Moreover, one or more radiopaque markers may be located on the transducer assembly to allow the user to determine the positioning and/or orientation of transducer 114 within the patient. For example, one or more radiopaque markers may be disposed in two perpendicular planes to each the positioning. Accordingly, when the transducer is configured such that at least a portion of the transducer emits less or no energy, e.g., forming a dead zone, as described in further detail below, the radiopaque markers may assist the user in determining which direction the dead zone is directed, so as to avoid sensitive anatomical structures, e.g., the phrenic nerve, the recurrent-Laryngeal nerve, or the airways, during the ablation procedure, e.g., creating a lesion on the other areas around the pulmonary artery.

Figure 7:
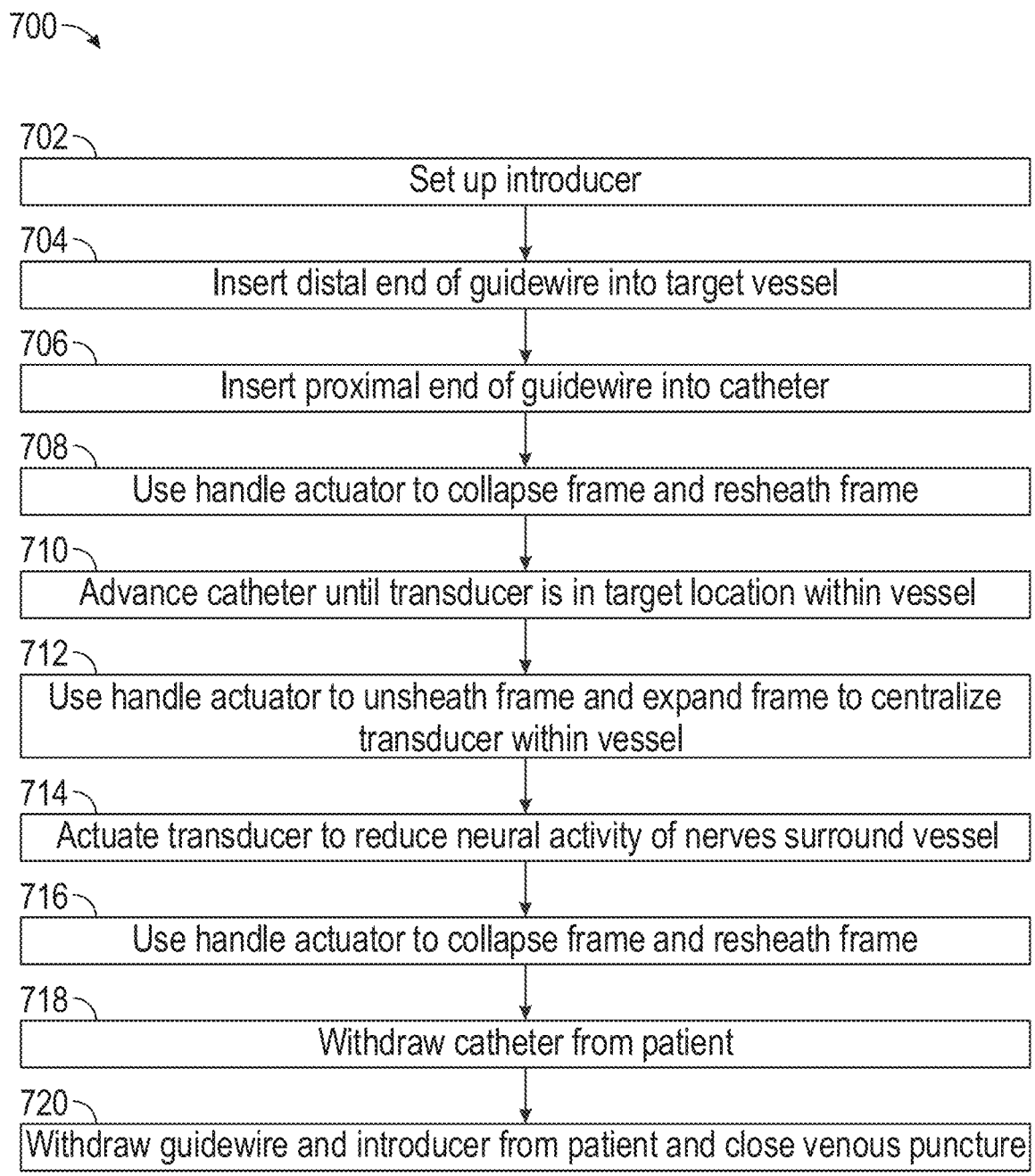
FIG. 7 is a flow chart of an exemplary method for treating tissue in accordance with the principles of the present disclosure.

Referring now to FIG. 7, method 700 for treating tissue using the catheter systems described herein is provided. At step 702, an introducer may be set up. For example, the introducer may be inserted through an entry site in the patient, e.g., a venous access point, and fixed relative to the patient. At step 704, the distal end of a guidewire may be inserted through the introducer and advanced into the target vessel, e.g., the pulmonary artery. For example, a Swan-Ganz catheter may first be inserted into the access point and floated to the target location within the target vessel. The guidewire may then be advanced through the Swan-Ganz catheter, and the Swan-Ganz catheter may be removed, leaving the guidewire in place from the access point to the target location. The guidewire may be steered, for example, under fluoroscopy from the access point to the target location.

At step 706, the proximal end of the guidewire, which is external to the patient, may be inserted into the catheter system, e.g., through the lumen of inner catheter 110 via tip 111. At step 708, handle 300 may be actuated to collapse anchor 200, e.g., an expandable frame, and to resheath anchor 200 within sheath 118. For example, as described above, knob 304 may be actuated to move inner catheter 110 distally relative to outer catheter 116 to cause anchor 200 to transition to the collapsed delivery state, then knob 306 may be actuated to move sheath 118 distally relative to anchor 200 until anchor 200 is disposed within distal region 118b of sheath 118, and the distal end of distal region 118b engages with tip 111. At step 710, distal region 104 of catheter system 100 may be advanced over the guidewire and through the introducer until transducer 111 is positioned within the target location within the target vessel. In some embodiments, catheter system 100 may include features of a Swan-Ganz catheter such as a floatable balloon, such that distal region 104 of catheter system 100 may be inserted into the access point and floated to the target location.

At step 712, handle 300 may be actuated to unsheathe anchor 200, and to deploy anchor 200 within the target vessel. For example, as described above, knob 306 may be actuated to move sheath 118 proximally relative to anchor 200 until anchor 200 is exposed from sheath 118, then knob 304 may be actuated to move inner catheter 110 proximally relative to outer catheter 116 to cause anchor 200 to transition to the expanded deployed state within the target vessel. At step 714, transducer 114 may be actuated to emit energy, e.g., ultrasonic energy, to the target vessel to reduce neural activity of nerves surrounding/innervating the target vessel. For example, transducer 114 may be actuated to emit energy in accordance with a predetermined ablation regime. The predetermined ablation regime may be selected to, e.g., to prevent overexposure and/or over ablation of the blood vessel. For example, the predetermined ablation regime may include predetermined periods of non-ablation where transducer 114 does not emit energy, or alternatively emits a reduces amount of energy, between predetermined periods of ablation where transducer 114 emits energy within the blood vessel. For example, the predetermined ablation regime may cause transducer 114 to emit energy for, e.g., ten seconds, then emit no energy for, e.g., five seconds before emitting energy for another ten seconds, and so on.

Transducer 114 may be operatively coupled to a generator for supply power to transducer 114, e.g., via conductive portion 602 and cable 600. The generator may be programmed with one or more control loops to ensure safe ablation by transducer 114. During sonication/ablation, the transducer dissipates in Joule effect the energy which was not converted into acoustic energy, thereby increasing the transducer temperature. Heating of the transducer surface may vary upon transducer builds, depending on their respective efficiency. Energy in a low efficient build will dissipate in Joule effect causing blood flow to be exposed to a higher temperature across the transducer. Blood flow across the transducer acts as a natural coolant for the transducer, e.g., as anchor 200 is non-occlusive, however, if blood is heated due to the transducer temperature above a given temperature threshold, fibrinogen in the blood may be denatured, leading to dangerous clots. The transducer temperature is a function of/proportional to the power applied to it, and thus, a control loop may be implemented by the generator to adapt the power delivery to a temperature target if a temperature threshold is exceeded. The control loop further may take into account temperature variations due to other factors such as the pulsatile flow of blood.

Figure 13:
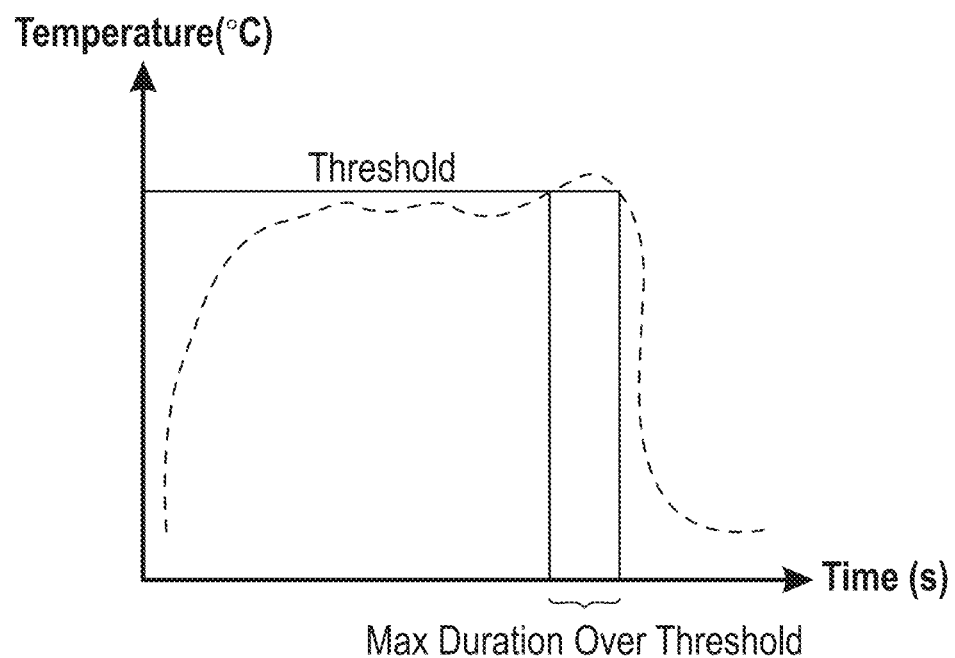
FIG. 13 is a graph illustrating a control loop of the catheter system.

As shown FIG. 13, the temperature monitoring allows the generator to stop the energy delivery if the temperature threshold is exceeded for a predetermined period of time, e.g., the max duration over threshold. For example, if transducer temperature, e.g., as measured via thermocouple 604 coupled to the generator, is below the temperature threshold, the generator may provide an amount of electrical power corresponding to the amount requested by the user/catheter system 100. Once the temperature threshold is exceeded, the control loop adapts the electrical power to prevent the transducer temperature from exceeding a target temperature. If the transducer temperature exceeds the safety threshold for more than, e.g., 2 seconds, the generator may cease power delivery to transducer 114. As an example, the temperature threshold may be defined between 50° C. and 56° C. and the acceptable time above the threshold may be defined between 0 and 4 seconds.

In addition, anatomical airway structures adjacent to transducer 114 may reflect acoustic energy back to transducer 114 during an ablation procedure. Transducer 114 may convert the reflected acoustic energy into electrical energy, which may be measured by the generator. Thus, the electrical energy measured by the generator would be higher than if an airway was not present. Accordingly, the generator may detect the presence of the airway structure based on the increased electrical energy converted by transducer 114, which is indicative of a level of acoustic energy reflected from an adjacent airway structure, and the control loop may be tuned to shut off sonication upon detection of a nearby airway structure.

As opposed to the nerves located in the adventitia of the pulmonary artery vessel, the transducer is exposed to the blood flow which is an excellent coolant. As a consequence, temperature slope when the pulse is stopped is greater in the transducer than in the tissue. To control the transducer temperature with a limited effect on the temperature build up at the lesion location, use of a duty cycle in the transducer electrical source is able to maximize the output power without proportionally increasing the off-time of the overall pulse duration.

Moreover, to increase the thermal energy dissipation of the transducer, a heatsink may be added at the proximal or the distal end of the transducer. For example, the heatsink may be a transducer end cap or a proximal support frame formed of stainless steel having a contact area with the blood that is between, e.g., 1 $cm^2$ and 3 $cm^2$. Alternatively, the proximal support frame may be connected to the anchor frame formed of nitinol or stainless steel to spread the transducer thermal energy to the entire surface of the anchor, which may represent between 5 $cm^2$ and 30 $cm^2$ of surface area in contact with the blood flow.

At step 718, upon completion of the ablation therapy, handle 300 may be actuated to resheath anchor 200 as described above, and catheter system 100 may be removed from the patient. At step 720, the guidewire and the introducer may be withdrawn from the patient, and the entry site, e.g., venous puncture, may be closed.

Figure 8:
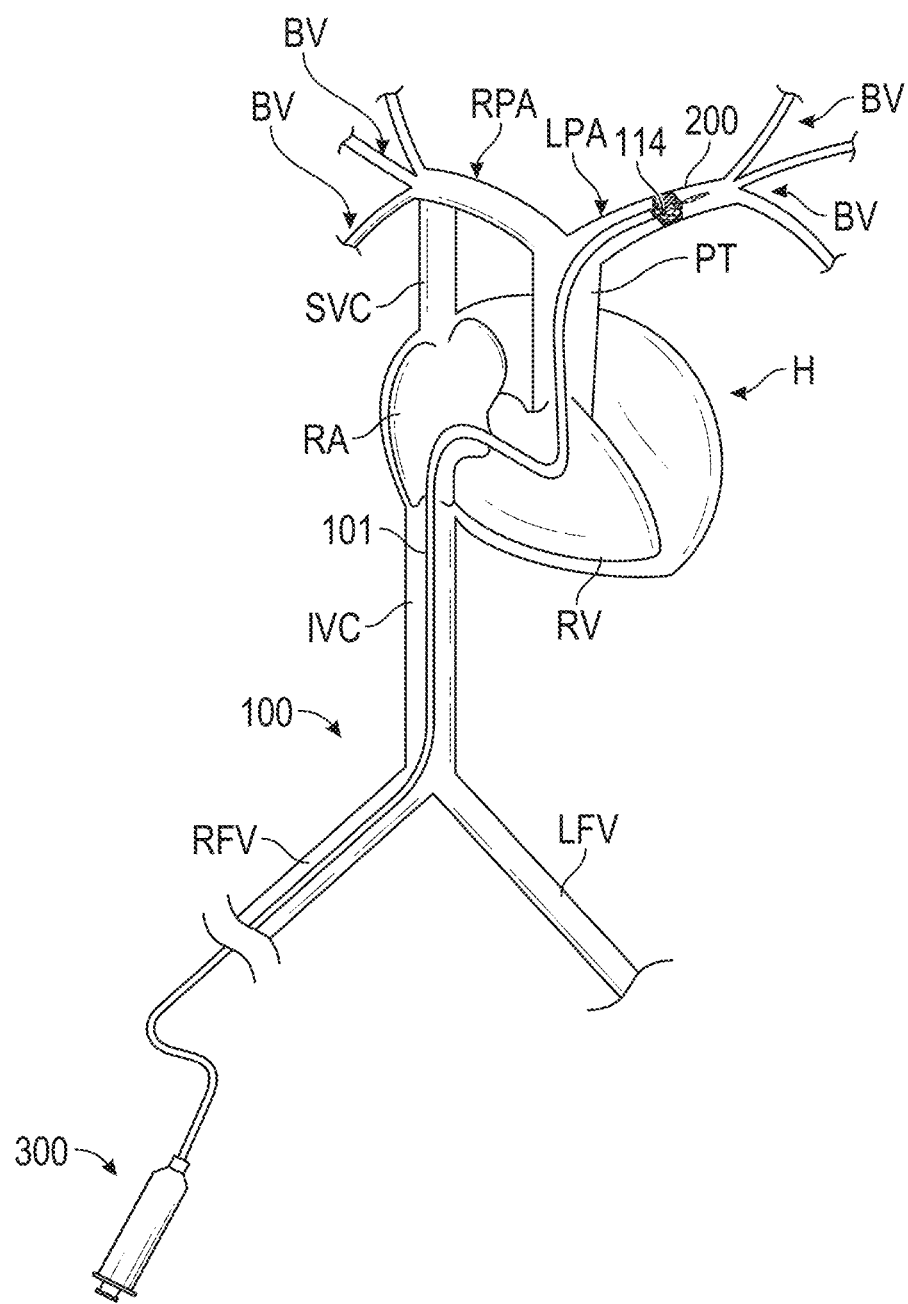
FIG. 8 is a schematic illustrating positioning of the catheter system of FIG. 1A within a patient in accordance with the principles of the present disclosure.

FIG. 8 schematically illustrates the general anatomy of the heart including pulmonary arteries and catheter system 100. The access pathway illustrated in FIG. 8 is one example of many possible access pathways for use with catheter system 100. As shown in FIG. 8, anchor 200 may be deployed within the left pulmonary artery LPA to secure and centralize transducer 114 within the LPA. Anchor 200 and transducer 114 are operatively coupled to handle 300, external to the patient, via elongated shaft 101 of catheter system 100.

Elongated shaft 101 is generally advanced through the vasculature and heart to a target location in the vasculature. As shown in FIG. 8, elongated shaft 101 may be advanced through an access point in a peripheral vessel, such as the right femoral vein RFV, into the inferior vena cava IVC, through the right atrium RA of the heart H, into the right ventricle RV, and then through the pulmonary trunk PT to the left pulmonary artery LPA. Other anatomical structures labeled in FIG. 8 include the right pulmonary artery RPA, branching vessels BV, superior vena cava SVC, and left femoral artery LFA. Alternatively, elongated shaft 101 may be advanced through an access point in the LFV, into the inferior vena cava IVC, through the right atrium RA of the heart H, into the right ventricle RV, and then through the pulmonary trunk PT to the left pulmonary artery LPA. Accordingly, elongated shaft 101 may have a length between about 100 cm and about 150 cm (e.g., about 100 cm, about 110 cm, about 120 cm, about 130 cm, about 140 cm, about 150 cm, and ranges between such values).

Alternatively, elongated shaft 101 may be advanced through an access point in a jugular vein, ulnar vein, etc., into the SVC, through the right atrium RA of the heart H, into the right ventricle RV, and then through the pulmonary trunk PT to the left pulmonary artery LPA. Accordingly, elongated shaft 101 may have a length between about 60 cm and about 120 cm (e.g., about 60 cm, about 75 cm, about 90 cm, about 105 cm, about 120 cm, and ranges between such values).

The target location may be any of a number of locations, for example, the pulmonary trunk PT, the left pulmonary artery LPA, the right pulmonary artery RPA, any of the branching vessels BV, the ostia of the left pulmonary artery LPA and/or right pulmonary artery RPA, and/or the like. Moreover, a different access method may be used, and a pulmonary vein or other pulmonary venous vasculature may be the target location. Additional access routes and potential targets are described in further detail herein.

Once at the target site, transducer 114 may be actuated to interrupt the nerves around the left, right, and/or main pulmonary arteries, e.g., neuromodulation. Neuromodulation may be accomplished (e.g., via ablation, denervation, which may or may not be reversible, stimulation, etc.), for example using acoustic energy (e.g., ultrasound), microwave energy, radiofrequency (RF) energy, thermal energy, electrical energy, infrared energy, laser energy, phototherapy, plasma energy, ionizing energy, mechanical energy, cryoablation, chemical energy, pulsed field electroporation, combinations thereof, and the like.

Pressure measurements within a blood vessel during distension of the blood vessel may be analyzed to confirm successful reduction of neural activity of nerves surrounding the target blood vessel, e.g., via the catheter systems described herein. Specifically, when a blood vessel having active nerves is distended, e.g., by applying a sufficient force to the inner wall of the blood vessel, baroreceptors within the blood vessel may be stimulated, thereby causing a corresponding increase in pressure within the blood vessel. However, data indicates that when the neural activity of the nerves surrounding the blood vessel has been reduced/inactivated, distension of the blood vessel either does not result in a corresponding increase in pressure within the blood vessel or results in a much smaller increase in pressure within the blood vessel. Accordingly, by comparing the pressure gradients within the blood vessel during distension of the blood vessel before and after an ablation procedure, successful reduction of neural activity of the nerves surrounding the blood vessel may be confirmed.

Figure 9:
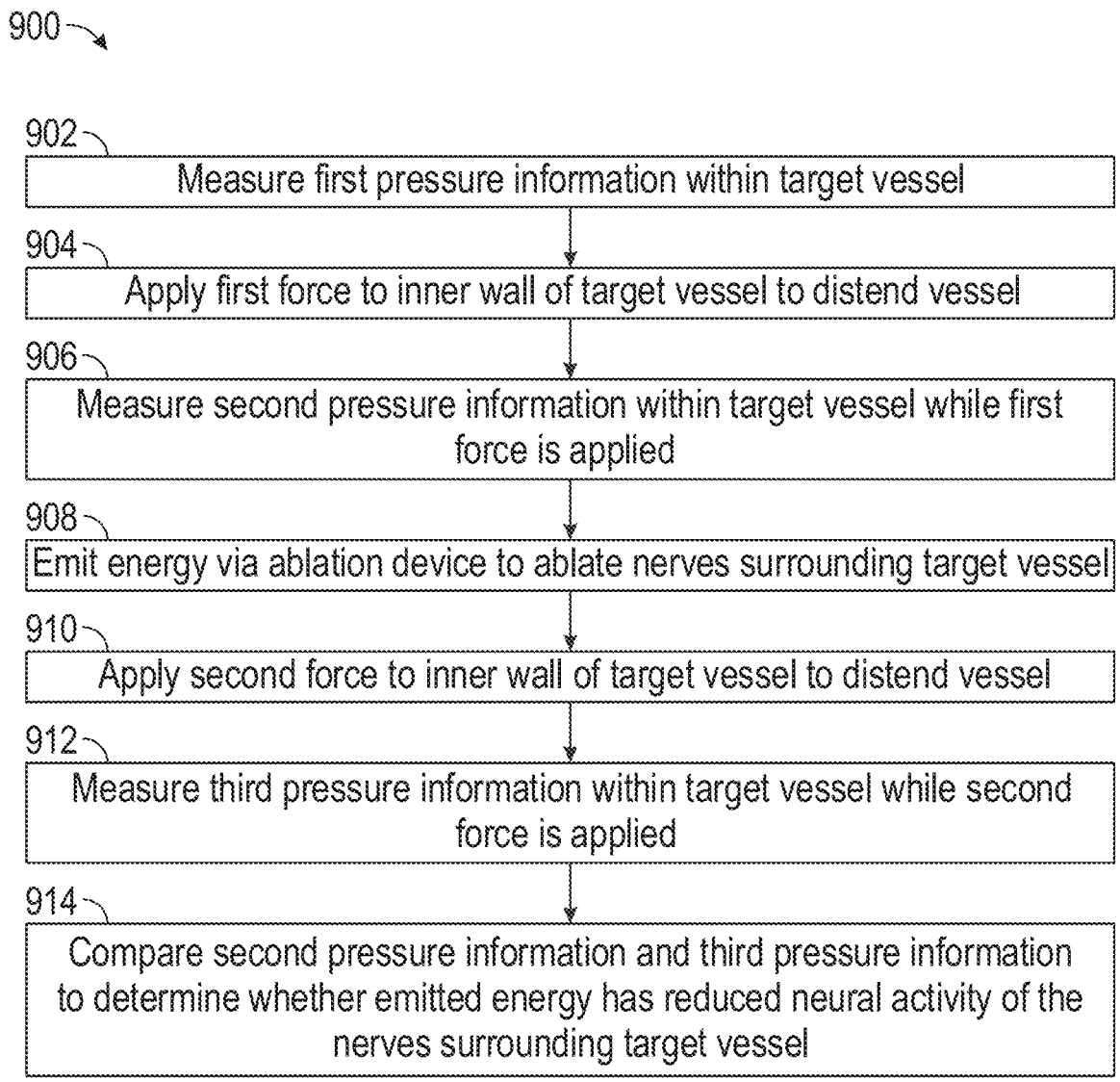
FIG. 9 is a flow chart of an exemplary method for confirming reduction of neural activity of nerves in accordance with the principles of the present disclosure.

Referring now to FIG. 9, method 900 for confirming reduction of neural activity of nerves is provided. At step 902, first pressure information may be measured within the target blood vessel, e.g., the pulmonary artery, at a first time. For example, pressure may be measure via one or more sensors or small transducers, e.g., FFR wires, integrated with catheter system 100, e.g., proximal and/or distal to transducer 114, or separate from catheter system 100. Additionally or alternatively, pressure may be measured via commercially available pressure transducers coupled to a lumen of elongated shaft 101, or pressure transducers inserted into a lumen of elongated shaft 101. The pressure sensors/transducers may be operatively coupled to a controller of catheter system 100 for recording and analyzing the pressure measurements. The first pressure information may be indicative of a pre-ablation baseline pressure within the blood vessel.

At step 904, a first force may be applied to the inner wall of the target blood vessel to distend the blood vessel, to thereby stimulate baroreceptors within the blood vessel wall at a second time. For example, the first force may be applied via a distension mechanism. The distension mechanism may be an expandable member, e.g., an expandable cage, that may be actuated to transition between a collapsed configuration and an expanded configuration wherein the expandable member applies a force to the inner wall of the blood vessel sufficient to distend the blood vessel. Preferably, the expandable member does not occlude the blood vessel in the expanded configuration. Alternatively, the expandable member may be a balloon configured to be inflated to distend the blood vessel. The expandable member may be disposed on a catheter separate from elongated shaft 101 of catheter system 100, or alternatively, the expandable member may be disposed on distal region 104 of catheter system 100, e.g., proximal and/or distal to transducer 114. In some embodiments, anchor 200 may be used as the distension mechanism, such that anchor 200 is expanded, e.g., via inner catheter 110 and outer catheter 116, to a diameter greater than the diameter of the inner wall of the blood vessel to thereby distend the blood vessel.

Alternatively, the distension mechanism may be a catheter shaft that may be actuated to form a bend to thereby apply a force to the inner wall of the blood vessel sufficient to distend the blood vessel. For example, the catheter shaft may be actuated by a pull-wire that, when pulled proximally via actuation at handle 300, causes the catheter shaft to bend and apply force to the inner wall of the blood vessel at the bend. The bendable catheter shaft may be separate from elongated shaft 101 of catheter system 100, or alternatively, the bendable catheter shaft may be integrated with elongated shaft 101, e.g., elongated shaft 101 may be configured to be actuated to form a bend to thereby apply a force to the inner wall of the blood vessel.

At step 906, second pressure information may be measured within the target blood vessel while the first force is being applied to the inner wall of the blood vessel. The second pressure information may be indicative of a first pressure gradient between pressure within the blood vessel while the first force is applied to the inner wall to distend the blood vessel and pre-distension pressure within the blood vessel associated with the first pressure information. The distension mechanism may then be actuated to cease application of force to the inner wall of the blood vessel.

At step 908, an ablation device, e.g., transducer 114, may be actuated to emit energy, e.g., ultrasonic energy, at a third time within the blood vessel to ablate nerves surrounding the blood vessel, for example, as described above with regard to method 700. For example, anchor 200 may be deployed prior to ablation to centralize transducer 114 within the blood vessel. During the emission of energy, when the ablation procedure is complete, or when the ablation procedure is otherwise presumed to be complete, at step 910, a second force may be applied to the inner wall of the target blood vessel, e.g., via a distension mechanism, to distend the blood vessel at a fourth time, to thereby stimulate baroreceptors within the blood vessel wall. In some embodiments, the distension force is continuously applied and pressure is continuously measured during emission of energy such that pressure gradients are monitored in real time to determine when the ablation procedure has sufficiently reduced neural activity, thereby causing energy emission to be ceased. Preferably, the same distension mechanism may be used to apply the first and second force to the inner wall of the vessel. Moreover, the same amount of force is preferably applied during the first and second vessel distensions.

At step 912, third pressure information may be measured within the target blood vessel while the second force is being applied to the inner wall of the blood vessel. The third pressure information may be indicative of a second pressure gradient between pressure within the blood vessel while the second force is applied to the inner wall to distend the blood vessel and pre-distension pressure within the blood vessel associated with the first pressure information. The distension mechanism may then be actuated to cease application of force to the inner wall of the blood vessel.

At step 914, the controller of catheter system 100 may compare the second pressure information to the third pressure information to determine whether the emitted energy has reduced neural activity of the nerves around the blood vessel. Additionally or alternatively, both the second and third pressure information may be displayed on a display for a user to manually compare the second and third pressure information to determine whether neural activity of the nerves around the blood vessel was successful reduced. Accordingly, a successful ablation therapy may be measured by a substantial reduction of neural activity or complete inactivation of the nerves as indicated by the comparison of the second and third pressure information. For example, it may be determined that the emitted energy has successfully reduced neural activity of the nerves around the blood vessel if the comparison of the second and third pressure information indicates that the second pressure gradient is less than the first pressure gradient by more than a predetermined threshold. Moreover, it may be determined that the emitted energy has successfully reduced neural activity of the nerves around the blood vessel if the second pressure gradient is zero, e.g., the post-ablation distension does not result in any increase in pressure within the blood vessel.

If the comparison of the second and third pressure information indicates that neural activity of the nerves has not been sufficiently reduced, e.g., the second pressure gradient is not less than the first pressure gradient by more than the predetermined threshold, the steps above may be repeated, e.g., steps 908-914. For example, transducer 114 may be redeployed if not already deployed, to emit additional energy within the target vessel. The target blood vessel may then be distended by applying a third force to the inner wall of the target vessel, and fourth pressure information may be measured within the target blood vessel while the third force is being applied to the inner wall of the blood vessel, such that the fourth pressure information may be indicative of a third pressure gradient between pressure within the blood vessel while the third force is applied to the inner wall to distend the blood vessel and pre-distension pressure within the blood vessel associated with the first pressure information. The fourth pressure information may then be compared to the third pressure information and/or the second pressure information to confirm with the neural activity of the nerves around the target blood vessel has been sufficiently reduced. The method steps above may be repeated until confirmation is received that the neural activity of the nerves around the target blood vessel has been sufficiently reduced.

Figure 10:
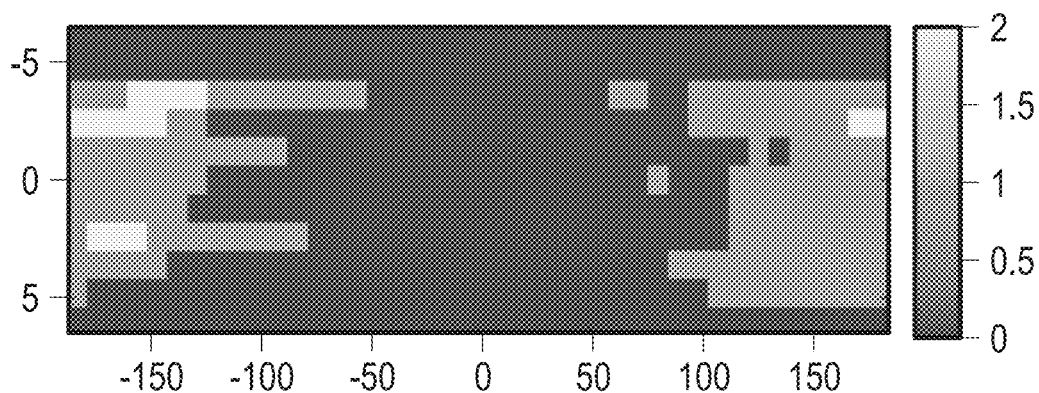
FIG. 10 is a distributivity plot diagram illustrating energy emission intensity.

To minimize the thickness of the outer diameter of the transducer, e.g., transducer 114, a conductive ring (e.g., copper) or tape may be used to extend the outer electrode connection and soldering from the inner diameter of the transducer assembly. To optimize the radiation of the piezoelectric element of transducer 114 and to reduce the mass loading effect due to the outer connection, the copper ring or tape may cover the full circumference of the outer electrode of transducer 114. Moreover, to control the directivity or the uniformity of the emitted energy, e.g., the acoustic beam, the inner diameter connection of the transducer assembly may be made of one or several connections spread over the inner electrode. Each solder spot over the inner electrode creates a mass loading and may change the radiation pattern of the transducer. For example, a wide or thick solder spot may narrow the directivity down to 50% at −6 dB from the maximum intensity, while thin solder spot(s) may lead to a 100% directivity at −6 dB from the maximum intensity, as shown in FIG. 10.

Additionally, transducer 114 may be covered with a very thin sleeve, e.g., to cover the piezoelectric surface which is not supposed to be a biocompatible material, to provide an electrical insulation for patient protection, and depending on the drive voltage amplitude and on the material dielectric strength, to define thickness of the transducer cover. The sleeve further may be thin enough to allow heat dissipation of the transducer in the blood flow during the sonication.

Figure 11:
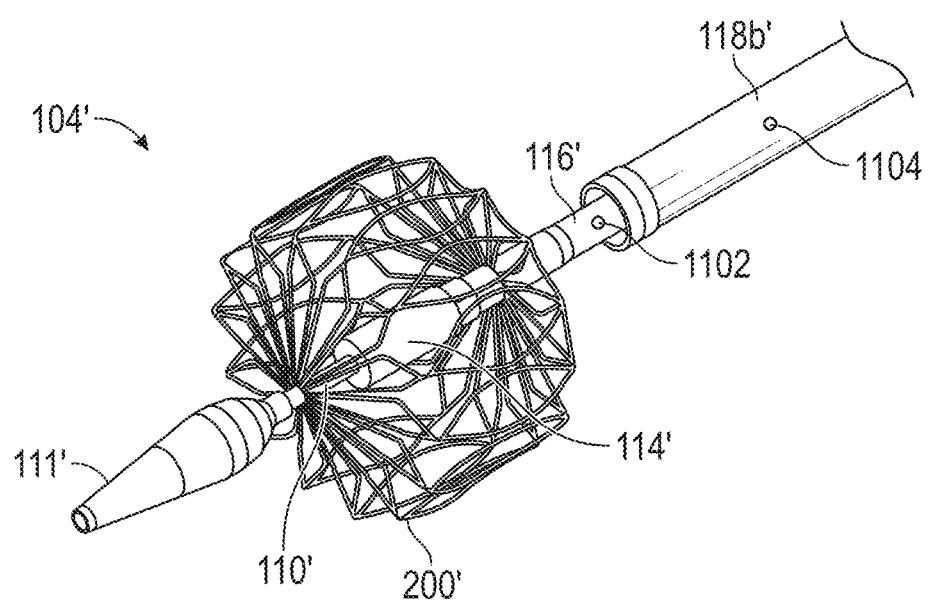
FIG. 11 illustrates the distal region of an alternative exemplary catheter system having guidewire ports constructed in accordance with the principles of the present disclosure.

Referring now to FIG. 11, an alternative distal region of the catheter system is provided. Distal region 104' may be constructed similar to distal region 104, with similar components having like-prime reference numerals. However, distal region 104' differs from distal region 104 in that distal region 104' may include a plurality of guidewire ports, e.g., guidewire port 1102 disposed on a distal region of outer catheter 116' and guidewire port 1104 disposed on a distal region of distal region 118*b*' of the sheath. In addition, inner catheter 110' may include a guidewire port (not shown), such that the proximal end of the guidewire may enter the lumen of inner catheter 110' via tip 111', and be fed through the guidewire port disposed on inner catheter 110', through guidewire port 1102, and through guidewire port 1104 such that the guidewire may extend along an exterior of the elongated shaft of the catheter system as distal region 104' is advanced over the guidewire to the target location within the blood vessel. Accordingly, inner catheter 110' does not need to have a guidewire lumen extending through its entire length, which would permit inner catheter 110' to have a smaller profile proximal to its guidewire port. Accordingly, the profile of all the components of the elongated shaft proximal to distal region 104' may be significantly reduced to reduce the stiffness of the elongated shaft, and therefore ease navigation and prevent heart straining during the procedure.

As described above, anchor 200 may be lasercut, e.g. from a metallic hypotube. In some embodiments, the anchor may undergo an extensive electropolishing treatment to render all of the edges of its plurality of struts round, thereby making the anchor safe to contact the patient anatomy during catheter delivery and/or during displacement from ablation site to ablation site. Accordingly, in this configuration, the catheter system would not require a sheath to be disposed over the anchor during delivery and displacement from ablation site to ablation site. Moreover, as the sheath would not be required, the separation sleeve also may not be required as the neither the transducer nor the anchor would need to be stabilized while a sheath is moved relative to the transducer and anchor. Thus, the profile of the elongated shaft of the catheter system would be significantly reduced, e.g., by the thickness of the sheath and the separation sleeve. In addition, the profile of the tip at the distal end of the inner catheter also may be reduced. As there may not be a need for a sheath or a separation sleeve, the corresponding hubs in the handle may be removed, thereby also reducing the profile of the handle.

Moreover, as the profile of the distal region of the catheter system dictates the size of the puncture required in the patient, e.g., at a venous access point, a distal region having a smaller profile would be more favorable to healing as well as reduce risk of infection, e.g., when the puncture is made in the groin area. To reduce the profile of the distal region, which is formed by the transducer, the anchor, and the sheath, the frame may be disposed distal to the transducer in both the collapsed delivery state and the expanded deployed state. For example, a proximal end of the anchor may be coupled to a distal end of the transducer shaft extending through the transducer and the tip of the inner catheter.

Figure 12:
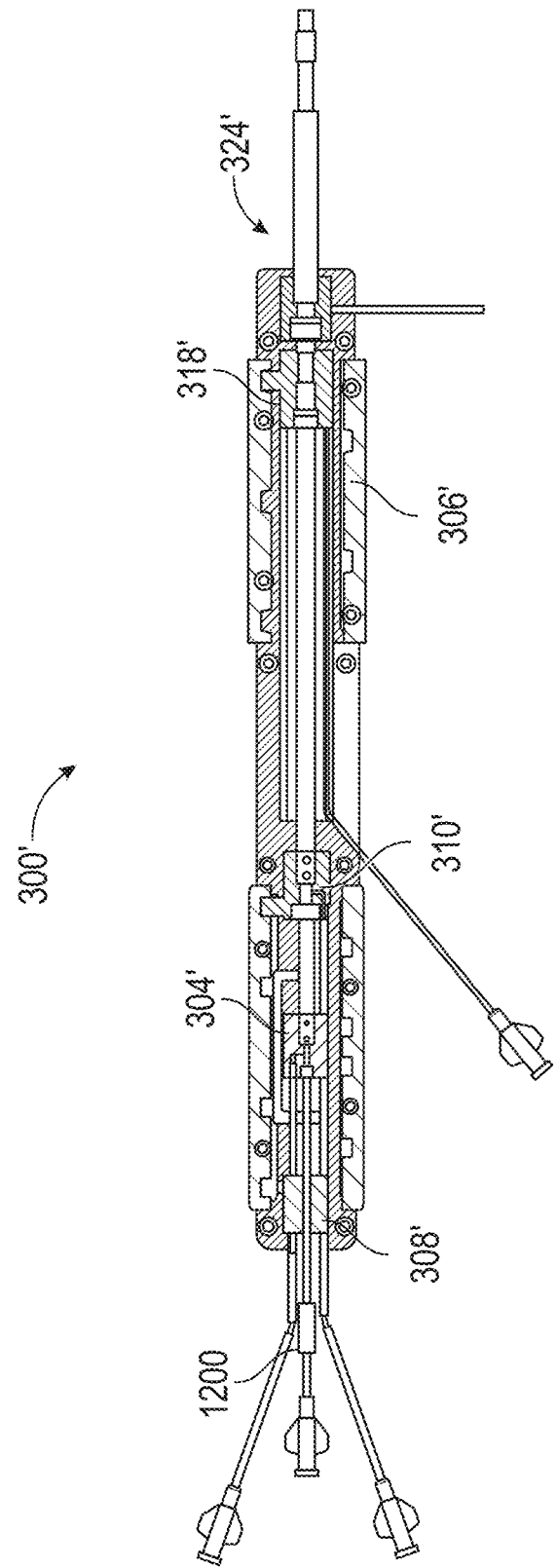
FIG. 12 is a cross-sectional view of an alternative exemplary handle constructed in accordance with the principles of the present disclosure.

Referring now to FIG. 12, and alternative exemplary handle is provided. Handle 300' may be constructed similar to handle 300, with similar components having like-prime reference numerals. Handle 300' differs from handle 300 in that handle 300' includes pusher 1200. Pusher 1200 is operatively coupled to the transducer at the distal region of the catheter system and is configured to be actuated to move the transducer transitionally relative to the frame. Accordingly, in this configuration, the transducer may be longitudinally moved relative to the outer catheter and the inner catheter. Thus, the transducer may be coupled to a transducer catheter that is slidably disposed within the outer catheter, such that the proximal end of the anchor remains coupled to the outer catheter. Moreover, the transducer catheter may have a lumen sized and shaped to slidably receive the transducer shaft therein, and may be sealed to the transducer shaft to form a fluidically sealed cavity between the transducer shaft and transducer catheter, instead of the outer catheter being sealed to the transducer shaft.

Thus, pusher 1200 may be operatively coupled to the transducer assembly, e.g., the transducer shaft, the transducer, and the transducer catheter, such that actuation of pusher 1200 causes translation movement of the transducer shaft, the transducer, and the transducer catheter relative to the anchor. Accordingly, the transducer assembly could move relative to the anchor to perform a plurality of ablations without collapsing and redeploying the anchor, as described in further detail below with regard to FIGS. 22A and 22B. As further shown in FIG. 12, both inner catheter hub 308', which is operatively coupled to the inner catheter, and outer catheter hub 310', which is operatively coupled to the outer catheter, may be operatively coupled to knob 304', such that actuation of knob 304' causes relative movement of the inner catheter and the outer catheter in equal and opposite directions.

Notably, the denervation around the pulmonary artery may intercept several adjacent anatomical structures, such as the aorta, the vena cava, the pulmonary veins, the phrenic nerve, the recurrent laryngeal nerve, the trachea, the bronchus, and the lungs. The aorta, vena cava, and pulmonary veins are protected by the blood that flows into these vessels, therefore, the heat generated by the absorption of the acoustic beam by the vessel wall is dissipated by the blood flow inside these vessels. However, this is not the case for non-target nerves, e.g., the phrenic and recurrent laryngeal nerves, which are not nearby a vascularized vessel, nor for the airways, e.g., trachea and bronchus, which are filled with air causing the reflection of most of the incident acoustic beam, thereby causing the target vessel to be up to twice exposed to the incident energy.

Figure 14:
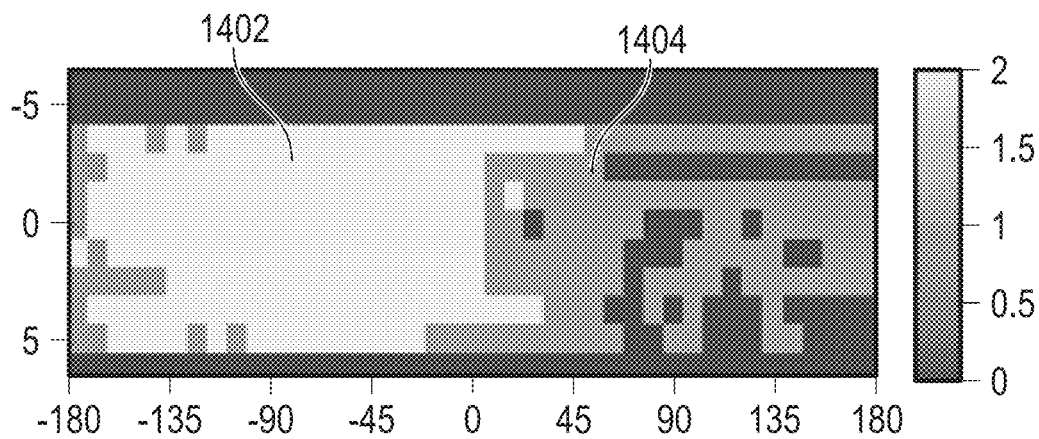
FIG. 14 is a distributivity plot diagram illustrating direct targeting of energy emission in accordance with the principles of the present disclosure.

To spare the non-targeted nerves from being damaged by the acoustic beam during sonication, the transducer may be designed as non-uniform, as described in further detail below with regard to FIGS. 19B to 19D. For example, the transducer may be configured such that 50% to 75% of the circumference of the transducer radiates a sufficient intensity to generate a lesion between, e.g., 15-33 W/cm$^2$, while the remaining 50% to 25% radiates half of this intensity. As shown in FIG. 14, the angles between −180° and +45° are radiating enough to create a lesion (zone 1402) with a direct targeting, while the angles between +45° and +180° are not sufficiently exposed to create a lesion unless they are reflected on the airways (zone 1404). The portion of the energy emitted at reduced intensity may be referred to herein as a "dead zone". The dead zone may be angled/directed toward the anatomical structure sought to be avoided during the ablation procedure.

This method requires the orientation of the transducer to be carefully taken into account during the procedure. Under fluoroscopy, a radiopaque marker band may be disposed on transducer 114 to enable the user to determine to location of the dead zone. The radiopaque marker may have an axially asymmetrical shape, such as a 'L' or a 'P', so the operator may readily discern the orientation of the transducer. For example, one or more radiopaque markers may be disposed in two perpendicular planes to each the positioning.

Figure 15:
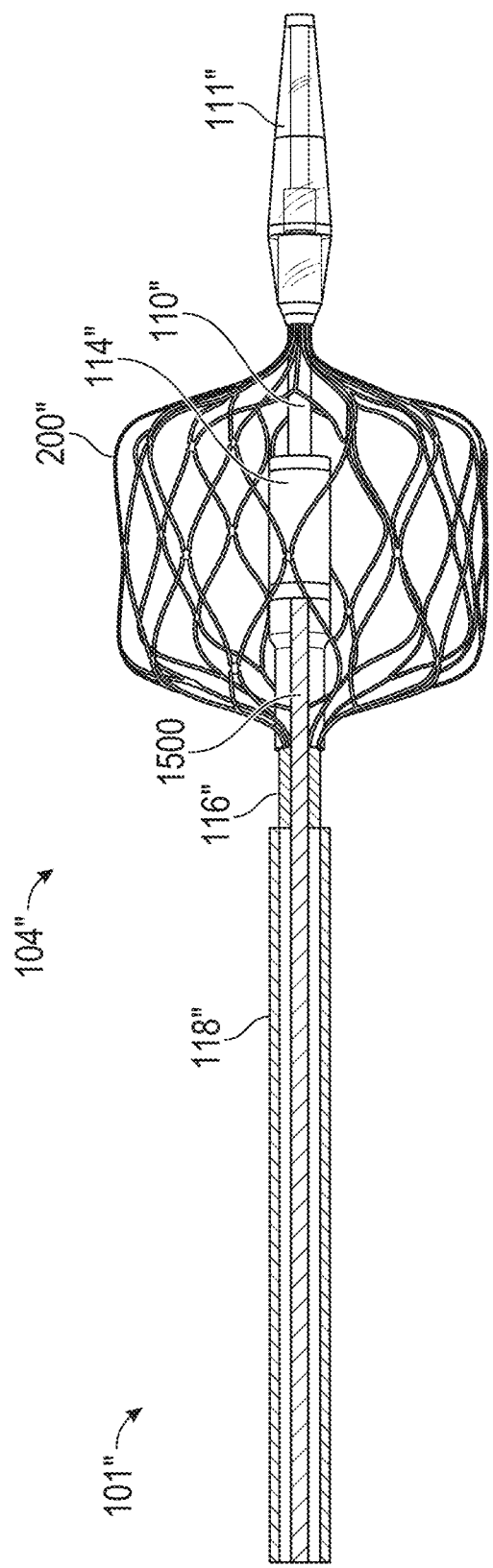
FIG. 15 illustrates an alternative exemplary catheter system having a rotatable torque shaft constructed in accordance with the principles of the present disclosure.

Referring now to FIG. 15, an alternative exemplary catheter system is provided. Elongated shaft 101" may be constructed similar to elongated shaft 101, with similar components having like-double prime reference numerals. However, elongated shaft 101" differs from elongated shaft 101 in that elongated shaft 101" may include torque shaft 1500. Torque shaft 1500 may be formed of, e.g., a multi-filar wire. A proximal region of torque shaft 1500 may be operatively coupled to the handle of the catheter system, and a distal region of torque shaft 1500 may be coupled to transducer 114", such that torque shaft 1500 may be actuated via the handle to rotate transducer 114". Accordingly, torque shaft 1500 may have a lumen sized and shaped to slidably receive inner catheter 110" therein, and may be disposed within outer catheter 116". As inner catheter 110" is fixed to tip 111", inner catheter 110" may remain stationary as torque shaft 1500 causes rotation of transducer 114". Preferably, rotation of transducer 114" is limited to 180° in both directions from a neutral configuration so as to avoid wrapping of the cables/electrical wires around torque shaft 1500.

Figure 16:
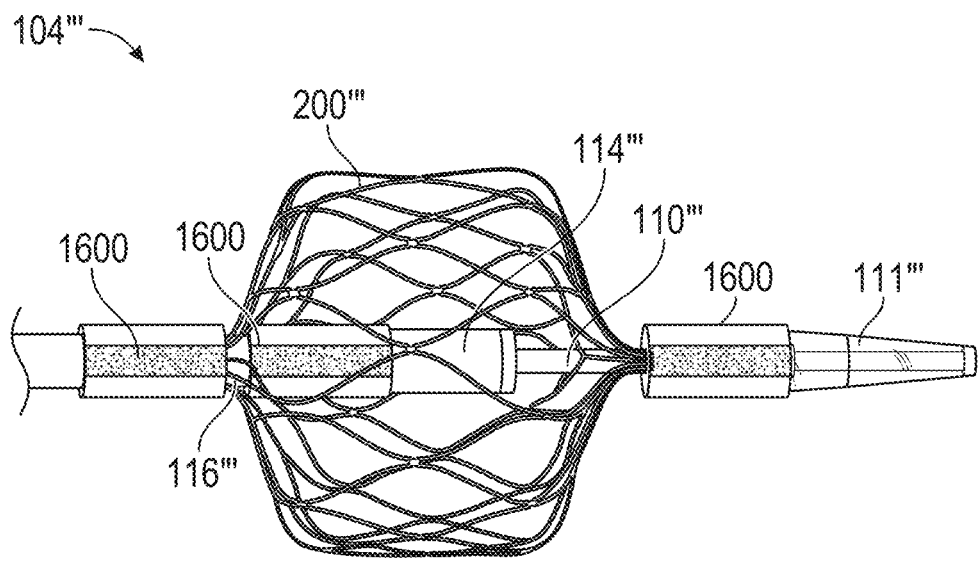
FIG. 16 illustrates an alternative exemplary catheter system having imaging transducers in accordance with the principles of the present disclosure.

Referring now to FIG. 16, another alternative exemplary catheter system is provided. Distal region 104''' of the catheter system may be constructed similar to distal region 104, with similar components having like-triple prime reference numerals. However, distal region 104''' differs from distal region 104 in that distal region 104''' may include one or more intravascular imaging transducers, e.g., intravascular ultrasound (IVUS) transducers. IVUS transducer 1600 is configured to provide intravascular imaging to permit a user to detect adjacent airways or other sensitive anatomical structures within a field of view of IVUS transducer 1600, e.g., trachea and bronchial airways, laryngeal and phrenic nerves, pericardium, aorta, etc. IVUS transducer 1600 may be a solid-state ultrasound imaging transducer or a rotation piezoelectric ultrasound imaging transducer.

IVUS transducer 1600 may generate data used to measure the distance between the pulmonary artery and an adjacent airway. The data may illustrate the airway as a lumen, but may further illustrate a reflected "blind spot" from the cartilage. Accordingly, transducer 114''' may be rotated, as described above with regard to FIG. 15, to align the dead zone of energy emission, as described above with regarding to FIG. 14, with the blind spot to avoid ablating the airway, or otherwise direct energy emission away from the airway. As shown in FIG. 16, a first IVUS transducer may be positioned on inner catheter 110''' between the distal end of anchor 200''' and tip 111''', a second IVUS transducer may be positioned on outer catheter 116''' between transducer 114''' and the proximal end of anchor 200''', and/or a third IVUS transducer may be positioned on outer catheter 116''' proximal to the proximal end of anchor 200'''. As will be understood by a person having ordinary skill in the art, more or less IVUS transducers may be integrated in distal region 104''' of the catheter system, and may be positioned on different locations along distal region 104''' than what is illustrated in FIG. 16.

Figures 17A, 17B:
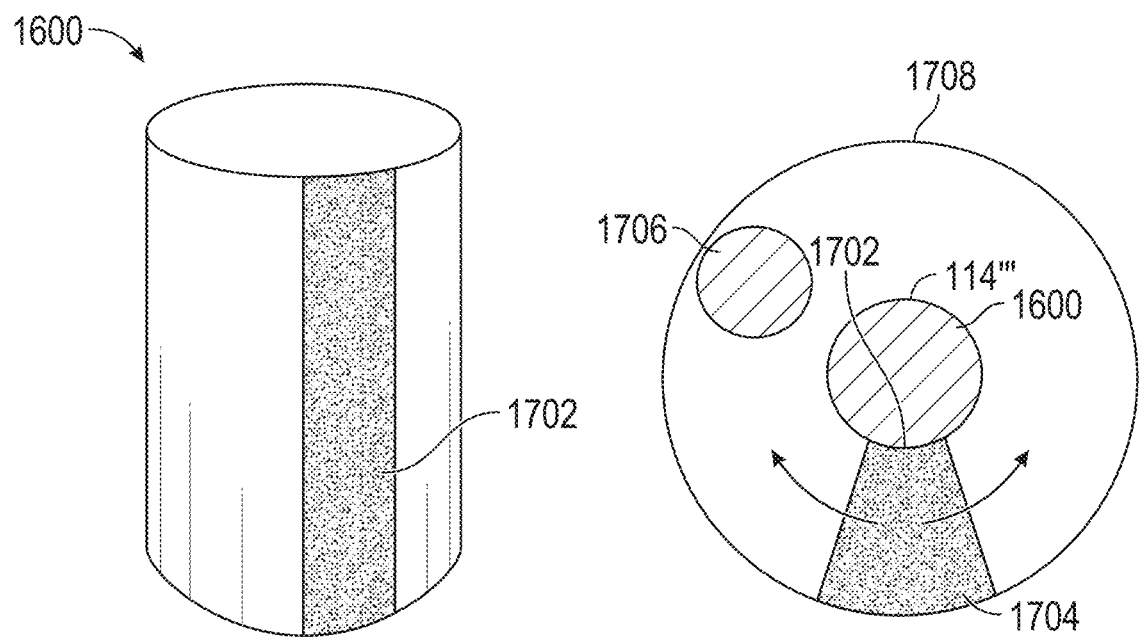
FIG. 17A illustrates an alternative exemplary imaging transducer having a shield constructed in accordance with the principles of the present disclosure.
FIG. 17B illustrates energy emission of the imaging transducer of FIG. 17A within a patient.

As adjacent sensitive anatomical structures may be imaged via IVUS transducers 1600 such that the dead zone of the transducer may be oriented to avoid the anatomical structure, it important for the user to know the direction that the dead zone of the transducer is currently pointing. As shown in FIG. 17A, shield 1702, e.g., a strip of metal or a portion of a cut metal hypotube, may be disposed on IVUS transducer 1600, to thereby mask a portion of the image generated via IVUS transducer 1600. Accordingly, shield 1702 may be oriented, e.g., as described above with regard to FIG. 15, to align shield 1702 with the dead zone of transducer 114'''.

As shown in FIG. 17B, IVUS transducer 1600 may provide imaging of airway 1706 within field of view 1708. Rotating IVUS transducer 1600 and transducer 114''' would rotate the blind spot on the image as well as the dead zone of transducer 114'''. Accordingly the blind spot and the dead zone may be aligned with airway 1706 to avoid ablation of airway 1706. In this configuration, both IVUS transducer 1600 and transducer 114''' are disposed on the torque shaft, as described above with regard to FIG. 15.

Referring now to FIG. 18, another alternative exemplary catheter system is provided. Distal region 104'''' of the catheter system may be constructed similar to distal region 104, with similar components having like-triple prime reference numerals. However, distal region 104'''' differs from distal region 104 in that distal region 104'''' includes one or more pacing electrodes 1800 disposed thereon. As shown in FIG. 18, pacing electrodes 1800 may be disposed on anchor 200'''', such that pacing electrodes 1800 may contact the inner wall of the blood vessel. Additionally or alternatively, pacing electrodes 1800 may be disposed on one or more expandable members proximal and/or distal to anchor 200''''. The phrenic nerve runs along the main pulmonary artery, and controls diaphragm movements, e.g., hiccups. Pacing electrodes 1800 may pace the blood vessel to detect the location of the phrenic nerve and/or prevent damage to the phrenic nerve by cutting off ablative energy by a control loop of the generator upon detection of the phrenic nerve. For example, pacing electrodes 1800 may pace the blood vessel prior to ablation to determine whether a phrenic nerve is present in the target ablation location within the blood vessel. This may be indicated by a physiological response from the patient, e.g., a hiccup-like reflex, if a phrenic nerve is located around the blood vessel being paced that corresponds with the pacing pulse of pacing electrodes 1800. The physiological response may be measured by a clinician, e.g., by feeling the patient's diaphragm during pacing. Accordingly, this portion of the blood vessel may be avoided (not ablated) to avoid damaging the phrenic nerve. Moreover, pacing electrodes 1800 may pace the blood vessel during ablation by transducer 114'''' to detect any abnormalities during the pacing indicative of damage to the phrenic nerve. For example, if a phrenic nerve is detected via pacing by pacing electrodes 1800, the clinician may feel the physiological response by the patient during the ablation procedure, such that a change in the frequency and/or intensity of the physiological response may be indicative of damage to the phrenic nerve. Accordingly, the user may stop ablation if such a change in physiological response due to pacing is detected during the ablation. As will be understood by a person have ordinary skill in the art, more or less than four pacing electrodes may be integrated with distal region 104'''', as shown in FIG. 18.

Figure 19A:
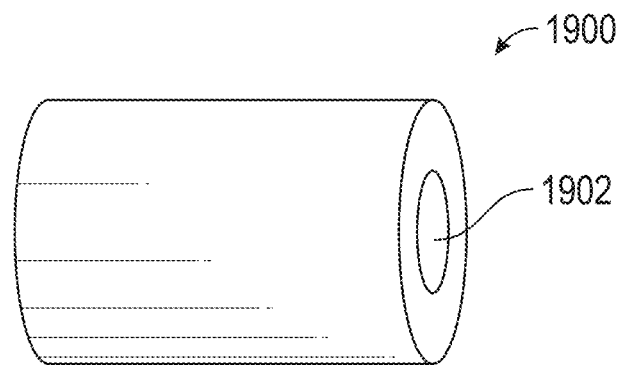
FIG. 19A illustrates an exemplary transducer constructed in accordance with the principles of the present disclosure.

FIG. 19A illustrates an example transducer 1900. Transducer 1900 may be positioned at or near a distal portion of a catheter system (e.g., catheter system 100). Transducer 1900 may be separate from any anchor (e.g., as described herein). Transducer 1900 may be coupled to a shaft (e.g., elongated shaft 101). Transducer 1900 may comprise hole 1902 extending therethrough, for example for coupling to a wire or tube of a catheter. Guidewires or sensor wires may extend through hole 1902. In some embodiments, transducer 1900 is an arcuate ultrasound transducer comprising a piezoelectric element.

The outer diameter of the transducers described here including, e.g., transducer 1900, may be between about 3 mm and about 10 mm (e.g., about 3 mm, about 4 mm, about 5 mm, about 6 mm, about 7 mm, about 8 mm, about 9 mm, about 10 mm, and ranges between such values). The transducer may have a length between about 5 mm and about 30 mm (e.g., about 5 mm, about 10 mm, about 15 mm, about 20 mm, about 25 mm, about 30 mm, and ranges between such values). A longer and/or thicker transducer can generally provide more power. A shorter and/or thinner transducer may be easier to navigate through vasculature. A thinner transducer may be used with a smaller incision, which can reduce scar size, infection site size, and/or healing time. A ratio between the diameter of the transducer and the length of the transducer may be between about 1/20 and about 2/1 (e.g., about 1/20, about 1/15, about 1/10, about 1/5, about 1/3, about 1/1, about 3/2, about 2/1, and ranges between such values).

Figure 19B:
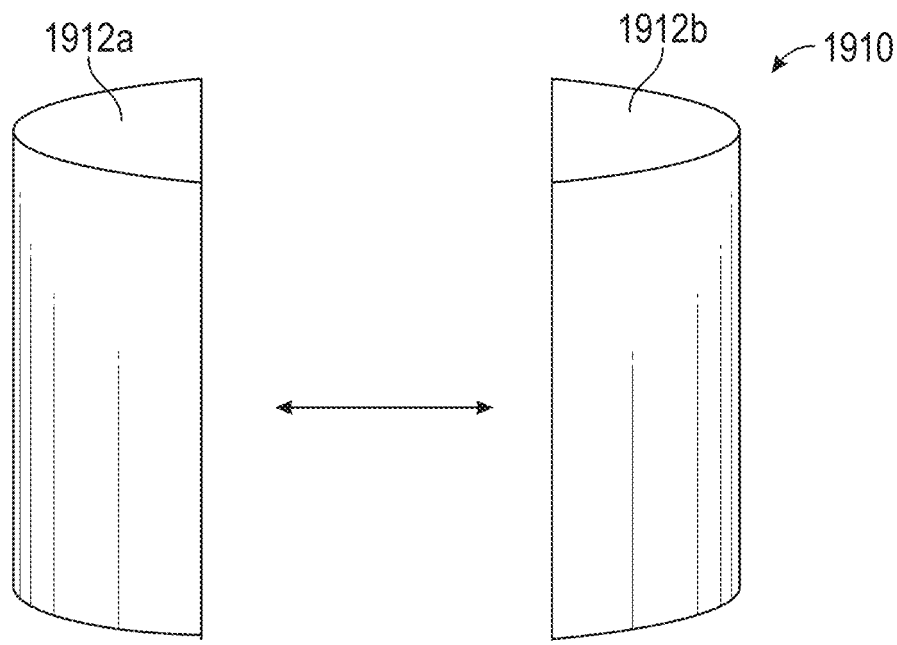
FIG. 19B illustrates another exemplary transducer constructed in accordance with the principles of the present disclosure.

FIG. 19B illustrates another example transducer 1910. Transducer 1910 may comprise a first hemicylinder 1912a and a second hemicylinder 1912b. First hemicylinder 1912a and second hemicylinder 1912b may be coupled to form a cylindrical shape. First hemicylinder 1912a may be activated for ablation while second hemicylinder 1912b is inactive. Partial activation can provide partial circumferential ablation, for example, to protect sensitive structures in the area around second hemicylinder 1912b. First hemicylinder 1912a may be activated for ablation and second hemicylinder 1912b may be activated for ablation. Coordinated activation can provide full circumferential ablation, for example, to treat tissue all around a vessel. Full circumferential ablation, as can be provided by the transducer assemblies provided herein, can reduce or eliminate rotation at an ablation site. In some embodiments, transducer 1910 is an arcuate ultrasound transducer comprising a piezoelectric element.

FIG. 19C illustrates another example transducer 1920. Transducer 1920 may comprise a plurality of angular or wedge-shaped arcuate regions 1922. Eight angular regions 1922 are depicted in FIG. 19C, but any numbers of regions may be used (e.g., two regions (e.g., as shown in FIG. 19B), three regions, four regions, five regions, six regions, seven regions, eight regions (e.g., as shown in FIG. 19C), nine regions, ten regions, eleven regions, twelve regions, and ranges between these values). Regions 1922 can all be the same, e.g., include the same material, shape, dimension, and/or the like. Alternatively, at least one of regions 1922 may be different than at least one other of regions 1922. For example, a difference may include a material, a shape, a dimension, and/or the like.

In another embodiment, the transducer may be divided asymmetrically into two independently actuatable regions, e.g., the circumference of the transducer may be divided into 10-90%, 15%-85% or 25-75%, etc. For example, when divided 10-90%, one region will consume 10% of the circumference of the transducer while the other region consumers 90% of the circumference of the transducer. Accordingly, the 90% region may be actuated to emit energy during the ablation procedure while the 10% region does not emit energy, thereby forming a "dead zone" of the transducer where energy is not emitted. As described above, the transducer may be rotated via to a torque shaft, such that the dead zone may be angled/directed toward sensitive anatomical structures nearby to avoid damaging the anatomical structures.

The angular regions 1922 may be activated through a plurality wires 1926, each connected to an ultrasound system and to one or more of regions 1922. In some embodiments, the user may decide which regions 1922 to activate during ablation. For example, the angular regions 1922 in FIG. 19C that are shaded are activated for ablation while the angular regions unshaded are not activated for ablation. Regions 1922 facing sensitive structures may not be activated to preserve those sensitive structures from being ablated. A larger quantity of regions 1922 can provide more activation flexibility in certain such embodiments. A smaller quantity of regions 1922 can provide less manufacturing complexity. In some embodiments, each angular region 1922 comprises a spring contact pad that can allow electrical power to flow through the disc when the disc is over region 1922.

FIG. 19D illustrates an example transducer connection implementation in which stacked discs 1924 that rotate on the edge of transducer 1920 can electrically connect or disconnect the angular regions 1922. As shown in FIG. 19D, the angular regions 1922 that are shaded are electrically connected via stacked discs 1924 and can be collectively activated for ablation. The angular regions 1922 are not connected via stacked discs 1924 cannot be activated for ablation. In some embodiments, stacked discs 1924 may be rotated independently through push and pull wires. In some embodiments, stacked discs 1924 comprises a single half disc 1924, two stacked half discs 1924, a single two-thirds disc 1924, a single three-quarters disc 1924, etc. Discs 1924 can provide an ablation profile that inhibits or prevents ablation in a region where a sensitive structure or other structure desirably not ablated is located. The rotation of the disc 1924 can be controlled from the proximal side of the catheter, for example, through a wheel that rotates a shaft with appropriate torquability. Two radiopaque symbols located on the actuating shaft can inform the operator about the positioning of discs 1924 and thus about the ablation profile that is or would be created.

Referring again to FIG. 8, elongated shaft 101 may need to navigate somewhat tortuous anatomy, including, for example, a right turn into the right atrium followed soon by a U-turn in the right ventricle. If any portion of elongated shaft 101 is too stiff or not flexible enough to make such turns, then distal region 104 might not be able to be delivered to the target location(s). FIG. 19E schematically illustrates an example transducer 1950 comprising a plurality of longitudinal segments 1952. Transducer 1950 may comprise any suitable quantity of longitudinal segments 1952 (e.g., two segments, three segments, four segments (e.g., as shown in FIG. 19E), five segments, six segments, and ranges between such quantities). More segments 1952 are also possible. Segments 1952 can be abutting or spaced apart by a distance. Segments 1952 may be spaced during navigation and then an actuator (e.g., controlling a pull wire and/or push rod) can cause the segments to abut during ablation. Transducer 1950 can ease the bending of the distal portion of the catheter during navigation to the target location(s) because the catheter is able to bend between segments 1952. In some embodiments, segments 1952 can provide electronic focusing of an ultrasound beam using phased wave generation. Segments 1952 may be partially activated, for example, similar to the hemicylinder portions 1912a, 1912b and/or angular regions 1922 described herein. For example, one, some, or all of segments 1952 may be activated for ablation depending on where the targeted nerves for ablation are located and where sensitive structures may be located.

FIGS. 20A to 20D illustrate example outer surface shapes of example transducers. FIG. 20A is an end view or a cross-sectional view of a transducer 2020 having a round outer shape 2022. The outer surface of transducer 2020 does not need to be a perfect circle. For example, transducer 2020 may be oval, elliptical, egg-shaped, etc. Transducer 2020 having an outer surface shape being round or arcuate can provide an ultrasound beam that is projected out in all directions, for example as schematically shown in FIG. 20A. An ultrasound beam projecting out in all directions can allow for ablation to occur around all areas surrounding a vessel wall at an ablation site, which optionally reduces or eliminates rotation of the transducer 2020 because an entire circumferential area can be treated with one ablation. Using only one ablation can reduce procedure time. Reduced procedure time for a target location can be especially important, for example, when multiple target locations are treated (e.g., multiple locations in the RPA, LPA, and PT), and/or if an anchor is collapsed and then re-expanded between ablations.

FIGS. 20B to 20D illustrate additional example outer surface shapes of transducers. FIG. 20B is an end view or a cross-sectional view of transducer 2024 having an octagonal outer shape. FIG. 20C is an end view or a cross-sectional view of transducer 2026 having a decagonal outer shape. FIG. 20D is an end view or a cross-sectional view of transducer 2028 having a dodecagonal outer shape. Transducers having any number of polygonal sides, preferably greater than five and less than 32, are also possible. While not a perfect circle, a higher number polygon outer shape can function similarly to a round outer shape in that the ultrasound beams projected out are in all directions from the transducer and produce a large amount of coverage. The transducer does not have an overall flat shape. For example, the transducer is not flat, two-sided, triangular, square, trapezoidal, parallelogram, or rectangular. Transducers of flat shapes, such as those listed herein, may not be able to provide a complete projection of ultrasound energy, and/or may require rotating the transducer to ablate all targeted nerves.

The transducers 2022, 2024, 2026, 2028 may include a plurality of hemi-pieces or wedge-shaped regions (e.g., as described with respect to FIGS. 19B and/or 19C), a plurality of longitudinal segments (e.g., as described with respect to FIG. 19E). Such regions and/or segments may be individually, partially, and/or collectively activated, as desired.

Any one of the transducers described herein or other transducers may optionally be coupled to a lens to focus or defocus the ultrasound energy. For example, energy from a cylindrical transducer can be focused by a lens to produce a toroid or doughnut-shaped treatment region around the transducer. Other shapes are also possible (e.g., spherical, ellipse, egg, arch, hemisphere, cigar, disk, plate, bulged versions thereof, etc.). The transducer may be acoustically coupled to the lens with piezoelectric material. The combination of the transducer and the lens may be called a transducer assembly, which may include the coupling material. In certain embodiments in which the device does not include a lens, the reference to a transducer assembly herein may refer to the transducer itself and optionally related components such as a conductor wire, material to couple the transducer to the shaft, etc. The focal length may be affected by the profile of the lens, the energy applied to the transducer, the efficiency of the components and/or assembly, and/or other parameters. In some embodiments, the efficiency of the assembly is tested by the manufacturer or a testing laboratory and the known efficiency is used during treatment.

Figure 21A:
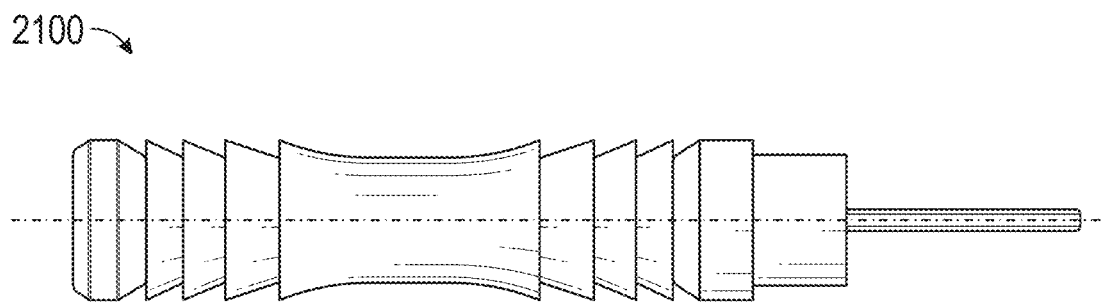
FIG. 21A illustrates an exemplary lens constructed in accordance with the principles of the present disclosure.
Figure 21B:
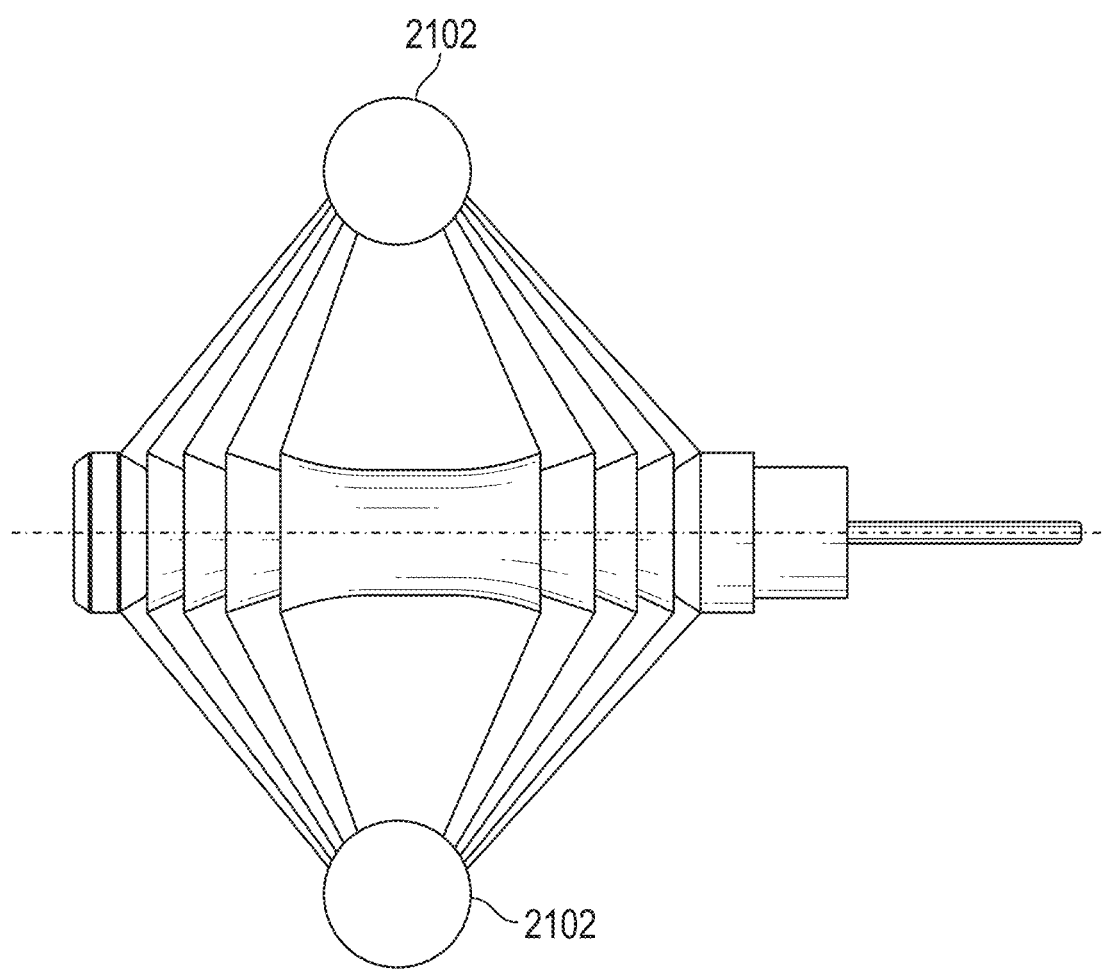
FIG. 21B schematically illustrates energy rays emanating from the lens of FIG. 21A to longitudinally focus and concentrate energy.
Figure 21C:
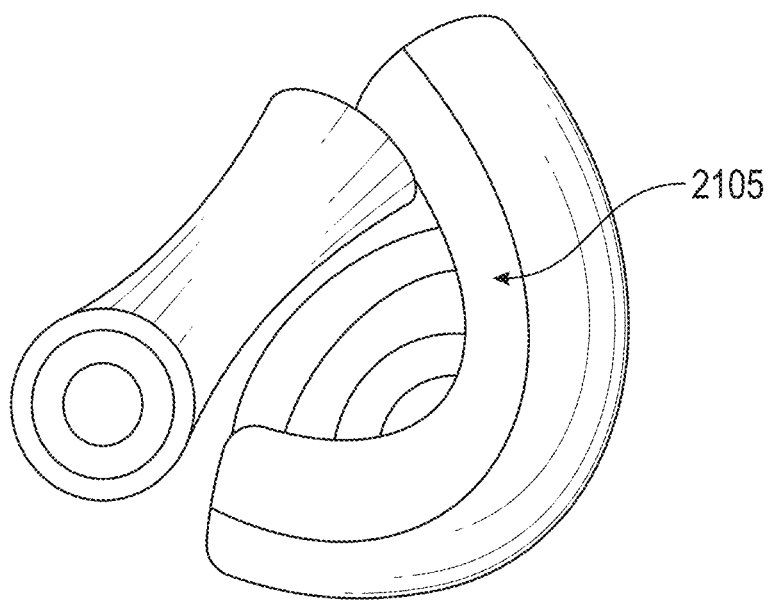
FIG. 21C illustrates a portion of an energy application shape.

FIG. 21A illustrates an example Fresnel lens 400. Lens 400 is acoustically coupled to a transducer. Fresnel lens 400 comprises a plurality of prisms configured to change the direction of the acoustic energy from the transducer so that the energy is generally focused to a common longitudinal area. The Fresnel lens can reduce the overall diameter of a catheter system, e.g., catheter system 100, and/or a portion thereof (e.g., a distal portion) because the prisms are able to redirect energy while maintaining a low profile (e.g., compared to a convex surface that may have a diameter that increases towards the longitudinal edges). FIG. 21B schematically illustrates example energy rays emanating from the prisms to longitudinally focus and concentrate acoustic energy to a smaller section 2102 around the transducer assembly. In practice, section 2102 can be tissue surrounding a vessel in which the transducer is positioned. In some embodiments, for a 22 mm focal point measured from the center of the transducer radially outward, a lesion that can be created by the energy may be pre-focal (e.g., about 1.5-5 mm from the vessel wall, depending on vessel diameter and other parameters). A larger amount of energy delivered and/or a longer delivery duration can increase the focal depth. A smaller amount of energy delivered and/or a shorter delivery duration can reduce the focal depth. The focus point of the energy does not have to be a pinpoint location or band. FIG. 21C illustrates an example portion of an energy application shape. Part of a toroidal area 2105 is illustrated. The energy application shape may be a full toroid, but shown in FIG. 21C as only part of a toroid for clarity. In some embodiments, the partial toroid shown in FIG. 21C may be created, for example, by activation of less than an entire transducer (e.g., one, two, or some wedges). The energy produced by a transducer may be at least partially absorbed by tissue in and/or around the vessel, which can create the toroidal ablation site 2105. Other energy application shapes are also possible (e.g., spherical, ellipse, egg, arch, hemisphere, cigar, disk, plate, bulged versions thereof, etc.).

The lens preferably comprises one or more materials that are acoustically conductive, good thermal conductors, good electrical insulators, and/or biocompatible. No one material may possess all of these properties, so a plurality of layers can be used (e.g., the outer-most layer can be biocompatible to protect the body from inner layers that are not as biocompatible). In some embodiments, the lens comprises aluminum that has been anodized or otherwise treated to have a coating of aluminum oxide (alumina). The aluminum and alumina are both good thermal conductors, the aluminum is acoustically conductive (e.g., the speed of sound through aluminum is about 4× the speed of sound through blood), and the alumina is biocompatible and a good electrical insulator. In some embodiments, the lens comprises silicon dioxide. Silicon dioxide is a good thermal conductor and biocompatible, and with certain doping, for example, may be suitably acoustically conductive.

Figure 21D:
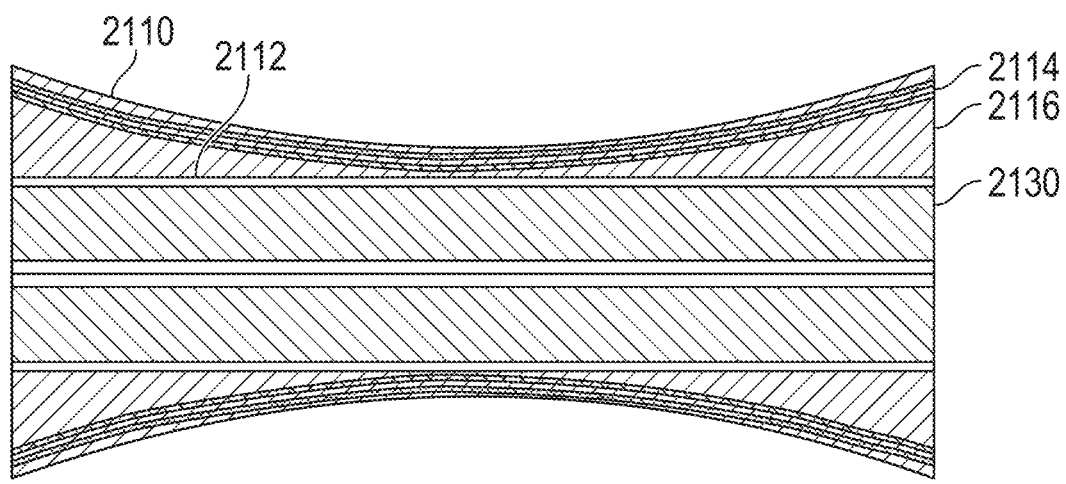
FIG. 21D illustrates an exemplary transducer assembly constructed in accordance with the principles of the present disclosure.

FIG. 21D illustrates an example transducer assembly. The assembly includes another example of lens 2110 coupled to a transducer (e.g., as described herein). Lens 2110 may be an ultrasonic lens. FIG. 21D is a cross-sectional view through the longitudinal axis L and depicts a transducer assembly comprising a cylindrical transducer 2130 and an ultrasonic lens 2110. Lens 2110 has an inner cylindrical surface and an outer surface shaped with a concave profile. Lens 2110 is acoustically coupled to the transducer 2130. The transducer assembly also comprises piezoelectric element 2112. Lens 2110 can focus energy from the transducer 2130 (e.g., as described herein). Because lens 2110 does not include a plurality of prisms, lens 2110 may have a larger diameter than Fresnel lens 400. Lens 2110 may be easier to manufacture than Fresnel lens 2100. Lens 2110 may be easier to flush with saline prior to insertion into vasculature than Fresnel lens 2100.

Lens 2110, or Fresnel lens 2100, increases the surface in contact with blood inside the vessel, which can improve the ability of the transducer to cool down by acting as a heat sink. To act as a heat sink, the lens material is preferably a thermal conductor (e.g., aluminum, alumina, silicon dioxide). The plurality of prisms of Fresnel lens 2100 can act as fins for the heat sink. In some embodiments, lens 2100, 2110 comprises biocompatible layer 2114. The lens covers piezoelectric material 2112 of transducer 2130 and inhibits or prevents contact between the blood and the outer surface of the transducer. In some embodiments, the lens comprises electrical insulation layer 2116. Insulation layer 2116 isolates the patient from the high voltage used to drive the transducer energy. The lens material may support dielectric properties to protect the patient from high voltage.

The devices described herein may lack or be devoid of a cooling system, which can advantageously significantly reduce device cost. For example, the blood flow through the pulmonary arteries may be sufficient to cool the transducer assembly. In contrast, a transducer assembly positioned in a renal artery may not be exposed to sufficient blood flow to provide enough cooling, and such devices may include a cooling system (e.g., a saline lumen pumped through the transducer before, during, and/or after ablation).

The size of a lens may depend, for example, at least partially on the material(s) and/or frequency (e.g., the natural frequency and/or the applied frequency from the ultrasound beam generator). Frequency adjustments can be made during the calibration or the setup of the transducer, for example so such adjustments do not need to be made during a procedure. Different frequencies may be used to ablate different depths outside the vessel. The material selected for the lens may impact the frequency needed for ablation. For example, if an acoustically poor material such as glass is used, the lens would be thinner to account for the losses caused by the acoustically poor material. If, for example, the material used has good acoustics, the lens may be thinner. For example, for a 25 mm focal length at 3 MHz over a 4 mm outer diameter transducer, an aluminum lens (c=6500 m/s) can have a profile of 5.4 mm, while an epoxy lens (c=2430 m/s) can have a profile of 7 mm for the same focal length.

Each transducer and lens combination has an associated data sheet that characterizes the transducer assembly and accounts for the differences in the transducer and lens combinations. Since the absorption of the acoustic energy by the tissue is a function of the frequency of the ultrasound beam, the transducer assembly should be carefully designed to meet the desired specifications. In an example implementation, a 4 mm outer diameter transducer is coupled to a 5 mm outer diameter aluminum Fresnel lens having a 25 mm focal length for operation at 4.5 MHz. In another example implementation, a 4 mm outer diameter transducer is coupled to a 6 mm outer diameter epoxy Fresnel lens having a 25 mm focal length for operation at 4.5 MHz. In another example implementation, a 1.5 mm outer diameter transducer is coupled to a 2.15 mm outer diameter aluminum Fresnel lens having a 10 mm focal length for operation at 6 MHz. In another example implementation, a 1.5 mm outer diameter transducer is coupled to a 2.8 mm outer diameter epoxy Fresnel lens having a 10 mm focal length for operation at 6 MHz. The catheter may comprise one or a plurality of flushing ports to inhibit or prevent introducing bubbles inside the patient (e.g., bubbles that might otherwise be trapped in the prisms of a Fresnel lens).

As described above, during ablation, a transducer assembly (e.g., as described herein) may be anchored within a vessel, e.g., via anchor 200. If the transducer assembly is not anchored, it may float or flop around in the blood flow, especially high blood flow like in pulmonary arteries, which can cause very unpredictable, or at the very least blurry and inefficient, ablation. Accordingly, the position of the transducer may be steadied by an anchor.

The anchors described herein may be configured to preserve blood flow through the vessel, including when the anchor is in a deployed state. A method including the anchor may comprise allowing blood to flow through the vessel when the anchor is in a deployed state. In some embodiments, the anchor does not comprise a balloon. For example, the edges of the prisms of a lens (e.g., Fresnel lens 2100) may damage a balloon anchor. In some embodiments, the anchor is not occlusive, allowing blood to continue to flow to downstream vessels and organs (e.g., the lungs). Renal denervation devices, for example comprising balloons, are typically occlusive because it is possible to pause blood flow to the kidneys without negative systemic effects. In some embodiments, a device configured to be used in pulmonary branch vessels (RPA and/or LPA) may comprise an anchor that occludes blood flow to one lung at a time because the other lung may be sufficient to oxygenate the blood for a short duration.

FIG. 22A illustrates an example embodiment of anchor 2200 comprising a plurality of struts 2204 in a collapsed or delivery state. Anchor 2200 is navigated to a vessel in the delivery or collapsed state. In some embodiments, anchor 2200 may be covered with a sheath during delivery or at other times in the delivery state. Anchor 2200 is deployable towards a deployed state.

FIG. 22B illustrates anchor 2200 in the deployed state. Depending on the diameter of the vessel, it may not be possible to achieve the delivery state shown in FIG. 22B, but expansion of anchor 2200 such that anchor 2200 is able to maintain a substantially constant position of the transducer assembly 2201 in the vessel may be considered the deployed state. Ablation preferably occurs when anchor 2200 is in the deployed state, or is not in the delivery state.

Plurality of struts 2204 may, for example, be cut (e.g., laser cut) from a hypotube or sheet. Cutting struts 2204 from a tube or sheet may, for example, provide quick and repeatable manufacturing. In some embodiments, plurality of struts 2204 are discrete wires. The wires are optionally not cut from a tube or sheet, or may be originally cut from a tube or a sheet in a manner that allows at least some of struts 2204 to be discrete (e.g., not directly coupled by strut material to another strut). Using discrete wires may provide flexibility in determining the shape and configuration of struts 2204. For example, plurality of struts 2204 may comprise wires that are straight, twisted, flat, round, combinations thereof, etc. (e.g., as shown in FIGS. 22A-22D). The wires may have a polygonal cross-section (e.g., rectangle, square, diamond, trapezoid, bulged versions thereof, etc.), a round or arcuate cross-section (e.g., circle, oval, ellipse, etc.), combinations thereof, and the like.

Struts 2204 may be coupled (e.g., individually coupled) (e.g., adhered, soldered, welded, not separated when being cut from a tube or sheet, combinations thereof, and the like) distal and proximal to transducer assembly 2201. As shown in FIG. 22A, distal portions of struts 2204 are coupled to a distal shaft 2202 and proximal portions of the struts 2204 are coupled to proximal shaft 2212. The distal shaft 2202 may comprise an atraumatic tip. The distal portions of struts 2204 may be coupled to the distal shaft 2202 distal to transducer assembly 2201. The proximal portions of struts 2204 may be coupled to the proximal shaft 2212 proximal to transducer assembly 2201. Transducer assembly 2201 may be substantially radially centered between struts 2204 in the delivery state and/or in the deployed state. The distal shaft 2202 is longitudinally movable relative to proximal shaft 2212. Such longitudinal movement may be allowed during self-expansion of anchor 2200 and/or used to expand anchor 2200. When struts 2204 bow radially outward, the longitudinal distance between the distal portion of the struts 2204 and the proximal portion of the struts 2204 is reduced. Transducer assembly 2201 may be substantially radially centered between the struts 2204 in the delivery state and/or in the deployed state.

In some embodiments, anchor 2200 is deployed by pushing the proximal and distal portions of the struts 2204 together (e.g., proximally retracting the distal shaft 2202 and/or distally advancing the proximal shaft 2212), causing the struts 2204 to bow radially outwards, as shown in FIG. 22B. In the deployed state, the plurality of struts 2204 expand out to contact or appose vessel walls. The anchor 2200 may maintain a longitudinal position of the transducer assembly 2201. This umbrella-type method of deployment can provide better control of the radial force being applied to the vessel wall by the anchor 2200. If the movement is manual by a hand of a user, for example, the user will be able to feel when the struts 2204 contact the vessel wall and stop expanding the struts 2204 at the appropriate deployed state. If the movement is motorized, for example, sensors may be used to measure force and stop movement upon reaching a certain force. To return to a delivery state, the struts 2204 are pulled apart (e.g., by distally advancing the distal shaft 2202 and/or proximally retracting the proximal shaft 2212) to collapse the struts 2204 back to the delivery state. The anchor 2200 is configured to expand to fit any appropriate size vessel. For example, the LPA, RPA, and PT do not have the same diameters as each other or uniform intra-vessel diameters, and the anchor 2200 is configured to expand to contact the vessel wall in all suitable locations of the LPA, RPA, and PT. In implementations such as ablation around renal arteries, the anchor 2200 is configured to expand to contact the vessel walls in all suitable locations in the left renal artery and the right renal artery.

The struts 2204 may be self-expanding. For example, the anchor 2200 may be collapsed and deployed by retracting and advancing an outer sheath 2210 to expose or cover the struts 2204. The outer sheath 2210 is proximally retracted in the direction of the arrow 2208 to allow the struts 2204 to at least partially self-expand. The anchor 2200 is returned to the collapsed state by distally advancing the outer sheath 2210 in the direction of the arrow 2209 to apply a radially inward force to the struts 2204 to cause the struts 2204 to collapse. In some embodiments, the outer sheath 2210 may be distally advanced to deploy the struts 2204 and proximally retracted to collapse the struts (e.g., using a push-pull mechanism such as a pull wire extending through the distal portion 502).

In some embodiments, the outer sheath 2210 may be used with umbrella-type expansion. For example, the outer sheath 2210 may protect the vasculature from the struts 2204 and vice versa during navigation to the target location. For another example, the outer sheath 2210 may have a lubricious surface that aids in navigation. For another example, the outer sheath 2210 may hold one or more sensors useful for measuring parameters near the transducer assembly 2201. For another example, the outer sheath may comprise a Swan-Ganz balloon to float the catheter to a target location (without using a separate Swan-Ganz catheter).

The outer diameter of the distal portion of the catheter including the transducer assembly 2201, the anchor 2200, and optionally the outer sheath 2210 is between about 3 mm and about 12 mm (e.g., about 3 mm, about 4 mm, about 5 mm, about 6 mm, about 7 mm, about 8 mm, about 10 mm, about 12 mm, and ranges between such values). A smaller diameter distal portion can allow insertion through a smaller incision. A smaller incision can reduce scar size, potential infection site size, and/or healing time.

In some embodiments, a combination of partial self-expansion and umbrella-type expansion are used. For example, the outer sheath 2210 may be proximally retracted, which can allow the struts 2204 to partially self-expand. This partial self-expansion may be sufficient to appose the vessel walls. In some alternative implementations in which anchoring is not desired but spacing between the transducer assembly 2201 and the vessel wall can be provided by the struts being partially self-expanded, this partial self-expansion may be sufficient. If the partial self-expansion is not sufficient (e.g., to sufficiently appose the vessel walls), then the umbrella-type expansion may be used to further expand the struts 2204, for example as described herein.

The plurality of struts 2204 preferably comprise a shape-memory material (e.g., Nitinol, chromium cobalt, MP35N, 35NPT, Elgiloy, etc.). Even in embodiments in which the anchor 2200 is not purely self-expanding, shape-memory material can help the plurality of struts 2204 maintain a shape, respond to external forces (including device-based expansion forces), etc. Other strut materials are also possible (e.g., stainless steel).

In some embodiments, the struts 2204 are not aligned with the transducer. For example, even if the transducer comprises four wedge-shaped pieces and the anchor 2200 comprises four struts 2204, the struts 2204 do not necessarily need to be aligned with (e.g., at intersections of) the transducer pieces. Rather, the struts 2204 can be independent of the transducer pieces.

The transducer assembly 2201 may be substantially radially centered between the struts 2204. If the struts uniformly expand, then the transducer assembly 2201 may be substantially centered in the vessel. Centering the transducer assembly 2201 in the vessel can help ensure that tissue all around the vessel is treated. For example, if the transducer assembly 2201 has a penetration radius of 20 mm and is centered in a vessel where the diameter of the vessel is 18 mm, then the penetration depth all around the vessel is about 11 mm. If the same transducer assembly 2201 was not centered in that same vessel, then penetration depth could be 3 mm in one direction and 19 mm in the opposite direction, either or both of which could affect undesired tissue. It will be appreciated that these numbers are for example purposes and that true numbers would take into account, for example, ultrasound absorption, diffraction at interfaces, Snell Descartes' law, etc.

FIGS. 22A and 22B schematically illustrate positions of some example radiopaque markers 2270, 2272, 2274, 2276. The marker 2270 is at a distal tip of the distal portion. The marker 2270 may be slightly spaced from the distal tip of the distal portion. The marker 2272 is at a distal end of the outer sheath 2210. The marker 2272 may be slightly spaced from the distal end of the outer sheath 2210. The marker 2274 is at a distal end of the anchor 2200. The marker 2274 may be slightly spaced from the distal end of the anchor 2200. The marker 2276 is at a proximal end of the anchor 2200. The marker 2276 may be slightly spaced from the proximal end of the anchor 2200. In some embodiments, the material of the anchor 2200 may be radiopaque such that the marker 2274 and/or the marker 2276 is the visible ends of the anchor 2200 (e.g., no separate marker material is used).

The marker 2270 can be used to control the distal tip of the device, for example to inhibit or prevent perforation distal to the treatment site and/or to inhibit or prevent application of pressure on small vessels. The marker 2272 can be used to determine the position of the outer sheath 2210, for example relative to other components. If the marker 2272 is distal to the marker 2274, the user knows that the anchor 2200 is covered by the outer sheath 2210. If the marker 2272 is proximal to the marker 2276, the user knows that the anchor 2200 is not covered by the outer sheath 2210. The user may observe the relative positions of the markers 2274, 2276 to gauge the expansion of the anchor 2200. For example, as seen in FIGS. 22A and 22B, when the markers 2274, 2276 are further apart, the anchor 2200 is closer to the collapsed position, and when the markers 2274, 2276 are closer together, the anchor 2200 is closer to the deployed or expanded position. In some embodiments, the distance between the markers 2274, 2276 can be measured (e.g., directly using fluoroscopy measurement (e.g., using the length of the transducer 2201 for scale), using indicia on the device, etc.) to determine the extent of expansion, which may include the diameter of the vessel at the deployment site. The extent of expansion and/or the diameter of the vessel at the deployment site may be used to set neuromodulation (e.g., ablation) parameters. The radiopaque markers described herein may be implemented in the other catheter systems described herein, e.g., catheter system 100.

The transducer assembly 2201 may be longitudinally movable relative to the distal shaft 2202 and/or the proximal shaft 2212 (e.g., by being coupled to an independent transducer shaft). For example, although the transducer assembly 2201 is illustrated as being large relative to the anchor 2200, the transducer assembly 2201 could extend over a much smaller longitudinal extent of the anchor 2200. The transducer assembly 2201 could move relative to the anchor 2200 to perform a plurality of ablations without collapsing and redeploying the anchor. For example, the transducer assembly 2201 could be at a first distal position in the anchor 2200, perform a first ablation, then can be proximally retracted to a second intermediate position in the anchor 2200 without moving the anchor 2200, perform a second ablation, then can be further proximally retracted to a third proximal position in the anchor 2200 without moving the anchor 2200, and perform a third ablation. In some embodiments, the transducer assembly 2201 could be at a first proximal position in the anchor 2200, perform a first ablation, then can be distally advanced to a second intermediate position in the anchor 2200 without moving the anchor 2200, perform a second ablation, then can be further distally advanced to a third distal position in the anchor 2200 without moving the anchor 2200, and perform a third ablation. In some embodiments, the transducer assembly 2201 could be at a first intermediate position in the anchor 2200, perform a first ablation, then can be distally advanced to a second distal position in the anchor 2200 without moving the anchor 2200, perform a second ablation, then can be proximally retracted to a third proximal position in the anchor 2200 without moving the anchor 2200, and perform a third ablation. The movability of the transducer assembly 2201 in the anchor 2200 is generally more important than the precise implementation of movement. While this may be mechanically more complex (e.g., as opposed to the transducer assembly 2201 being mounted between the distal shaft 2202 and the proximal shaft 2212), such movement could reduce operation time by reducing or eliminating the collapsing, repositioning, and redeploying of the anchor after each of the first and second ablations.

The struts 2204 may have a thickness between about 30 μm and about 500 μm (e.g., about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 500 μm, and any ranges between these values). This thickness is measured in the radial direction of each individual strut 2204. The thinner the struts 2204, the less likely the struts 2204 are to cause interference or scattering with an ultrasound signal. For example, the struts 2204 may cast an ultrasound shadow resulting in areas covered by the shadow not being ablated.

The plurality of struts 2204 may comprise between about four struts and about 64 struts (e.g., about four struts, about six struts, about eight struts, about ten struts, about twelve struts, about sixteen struts, about twenty struts, about thirty struts, about forty struts, about fifty struts, about 64 struts, and ranges between such values).

The applicant has discovered that strut thicknesses less than about 100 μm does not appreciably affect an ultrasound signal. In embodiments having thin struts (e.g., between about 30 μm and about 100 μm), a larger quantity of struts (e.g., between about) may be used to increase the amount of total apposition force on the vessel wall to provide suitable anchoring.

Some embodiments may comprise thicker struts (e.g., between about 110 μm and about 500 μm). For example, the interference or shadow caused by the thicker struts may be advantageously used to protect a portion of the vessel wall while ablating the targeted tissue (e.g., including nerves) beyond the vessel wall. The thicker struts may provide higher radial force on the vessel wall for a more secure anchoring.

A balance between reducing interference or a shadow produced by the struts 2204 and sufficient radial force may be desirable. The number or quantity of struts 2204 may be varied to counteract any interference or shadows and/or to increase radial force as may be appropriate. A lower number of struts 2204 can reduce potential interference and shadows. A higher number of struts 2204 can increase radial force.

Figure 22C:
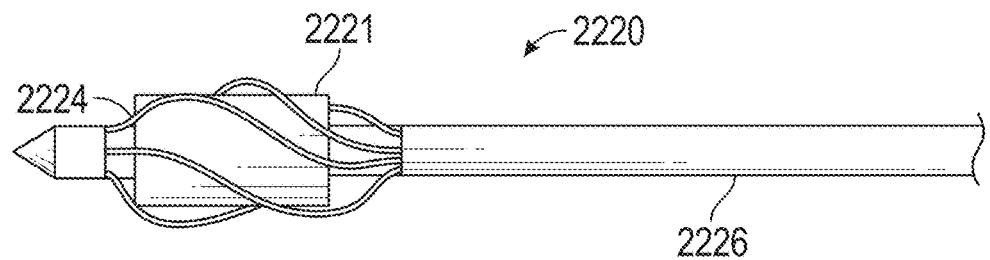
FIG. 22C illustrates another exemplary anchor in a collapsed delivery state constructed in accordance with the principles of the present disclosure.
Figure 22D:
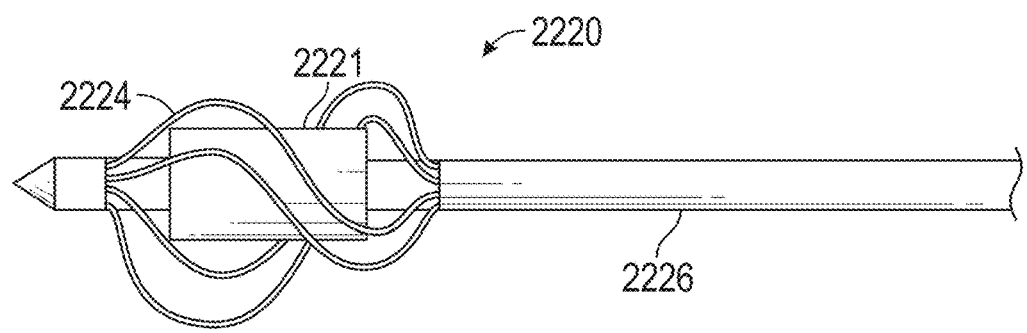
FIG. 22D illustrates the anchor of FIG. 22C in a deployed state.

FIG. 22C illustrates another example of an anchor 2220. FIG. 22C illustrates a collapsed or delivery state of the anchor 2220. FIG. 22D illustrates a deployed state of the anchor 2220. The anchor 2220 comprises a plurality of struts 2224 that are twisted around the transducer 2221. The plurality of struts 2224 may be collapsed and deployed via any of the methods described herein (e.g., self-expanding, umbrella-type, and combinations thereof). The twisted configuration of the plurality of struts 2224 can reduce the overall interference or ultrasound shadows that the plurality of struts 2224 may create across the transducer assembly 2221. For example, there is less interference produced in the longitudinal direction by each strut 2224 because the twisted configuration will only cover a portion of the transducer assembly 2221 in the longitudinal direction instead of an entire section of the transducer assembly 2221 in the longitudinal direction.

As shown in FIG. 22D, along any longitudinal line, there may be a portion of one or several struts 2224, but there is no longitudinal line that is entirely a strut. The twisted configuration allows for coverage by the struts 2224 to be positioned in various sections of the transducer assembly 2221, such that entire longitudinal sections are not covered. Combined with the application of power to the length of the transducer assembly 2221 and the focusing provided by the lens, a twisted configuration of the plurality of struts 2224 may increase the probability of all the targeted tissue (e.g., including nerves) being ablated due to the reduction in potential interference or shadows caused by the struts 2224. Twisted struts 2224 can provide a partially lateral dimension to the anchor 2220, which can help to provide better vessel wall apposition, for example providing a counter force to longitudinal blood flow. Straight struts 2204 may be less prone to cause blood turbulence. The various strut configurations described herein may be implemented in other catheter systems described herein, e.g., catheter system 100.

Figure 23A:
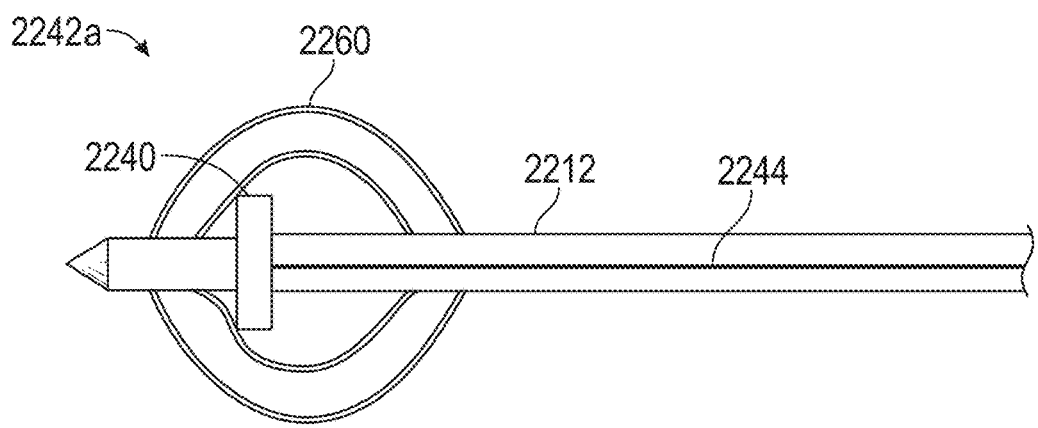
FIGS. 23A and 23B illustrate an exemplary transducer assembly constructed in accordance with the principles of the present disclosure.
Figure 23B:
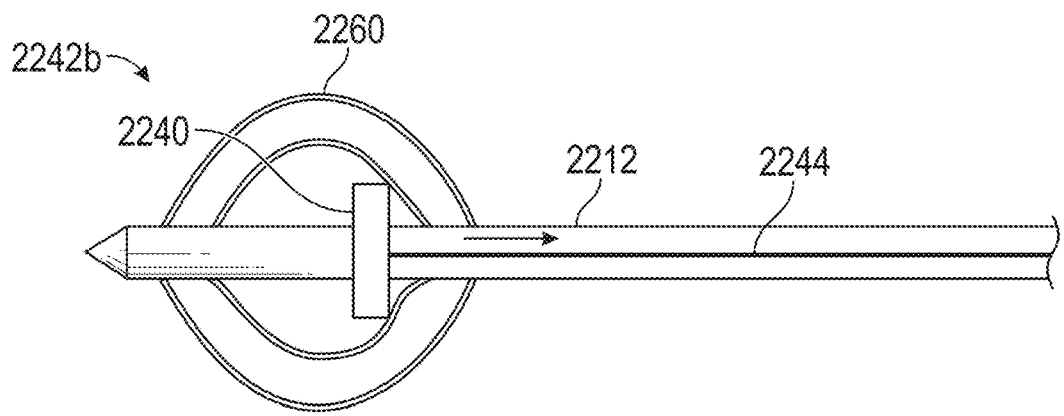

FIGS. 23A and 23B illustrate an example transducer assembly including a transducer 2240 that is configured to slide over an inner shaft 2212 when the anchor is deployed. When the anchor 2260 is deployed, the transducer 2240 is translated across the inner shaft 2212 to ablate several ablation sites (e.g., a first ablation site 2242a and a second ablation site 2242b) at one anchoring position. The transducer 2240 may be translated to one, two, three, four, five, or more ablation sites, or more if desired, at one anchoring position. This method of translating the transducer 2240 can reduce treatment time by reducing the amount of times the anchor 2260 is collapsed and moved, and then redeployed within a vessel. In some embodiments, the anchor 2260 may be only partially collapsed or not collapsed before movement (e.g., it may be worth possible vessel wall damage to reduce procedure time by moving an at least partially expanded anchor). The transducer 2240 may be connected to a pull and/or push wire 2244 to move the transducer 2240 along the inner shaft 2212.

Figure 23C:
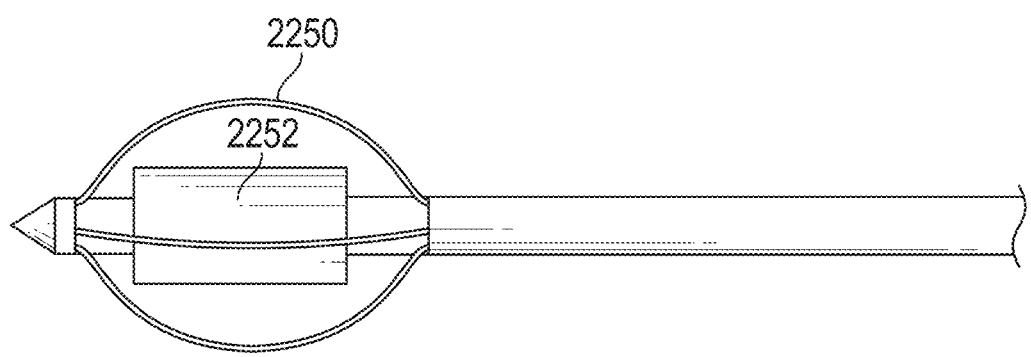
FIGS. 23C to 23E illustrate an exemplary method of rotating an anchor between ablations.
Figure 23D:
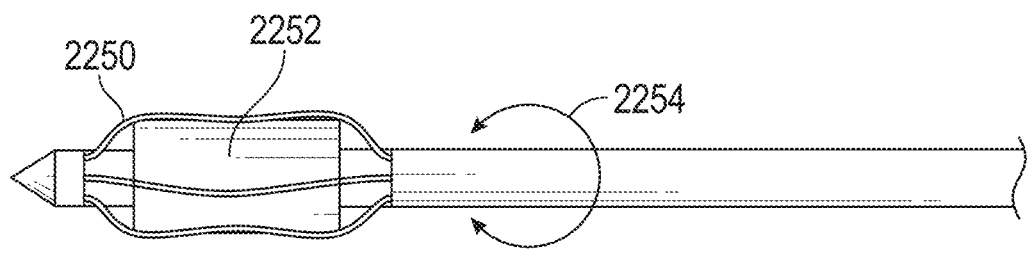
Figure 23E:
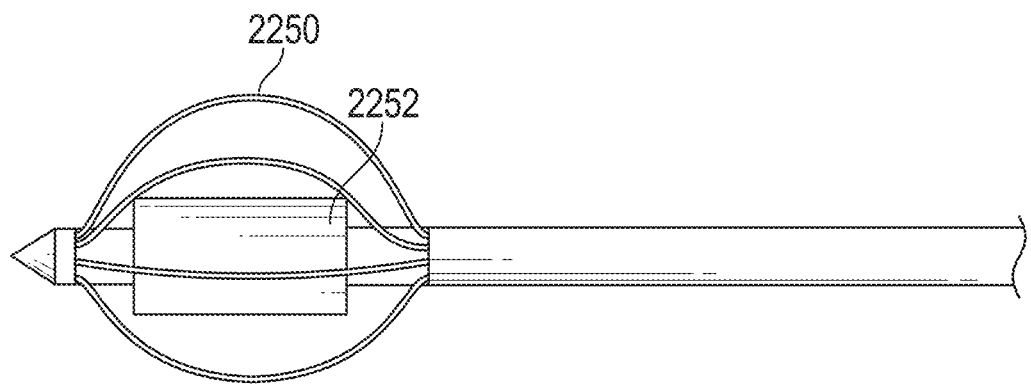

FIGS. 23C to 23E illustrate an example method of rotating an anchor 2250 between ablations. Rotation of the anchor 2250 may counteract or account for any interference caused by shadows created by the anchor 2250. After a first ablation conducted in a deployed state as shown in FIG. 23C, the anchor 2250 may be collapsed to a delivery state as shown in FIG. 23D. The anchor 2250 may then be rotated as shown by the arrow 2254. The anchor 2250 is preferably not longitudinally moved during rotation. The anchor 2250 is then redeployed with the struts touching a different portion of the vessel wall, as shown in FIG. 23E. The struts of the anchor 2250 are in different positions than in FIG. 23C, which results in any interference or shadows occurring in different areas of the vessel, which can allow the transducer 2252 to ablate the tissue where the shadows were cast in FIG. 23C, thereby providing a more complete ablation. This process will be repeated as many times as desired to account for interference or shadows.

Figure 24A:
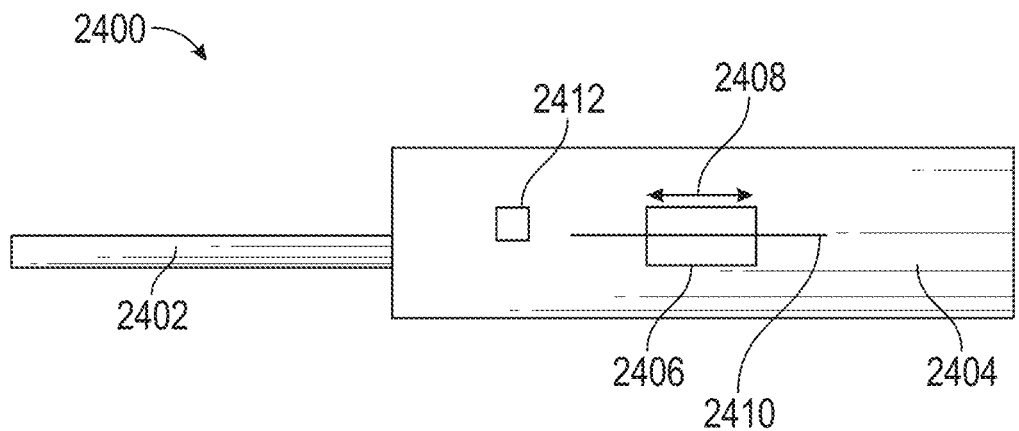
FIG. 24A schematically illustrates an exemplary catheter comprising a handle and an elongate shaft constructed in accordance with the principles of the present disclosure.

FIG. 24A schematically illustrates an example embodiment of a catheter 2400 comprising a handle 2404 and an elongate shaft 2402. A distal portion of the elongate shaft 2402 may comprise the transducer assembly, anchor, etc. The handle comprises an actuator 2406. The actuator 2406 may be used to collapse and/or deploy the anchor 2400. The actuator 2406 may comprise, for example, a thumb wheel or slider. In some embodiments in which the actuator 2406 comprises a slider, the actuator 2406 can slide along a path 2410 in either direction, as indicated by the arrow 2408. In some embodiments, the actuator 2406 can inform the operator about the inner diameter of a vessel. For example, as described herein, the longitudinal distance between the distal shaft 2402 and the proximal shaft 2412 is related to the radial expansion of the struts 2404. If the actuator 2406 proximally retracts the distal shaft 2402 by a certain distance, then the corresponding extent of the radial expansion of the struts 2404, and thus the diameter of the vessel that stopped expansion of the struts 2404, can be determined. The handle 2404 may comprise indicia along the path 2410. Vessel diameter information may be used to select the energy value (e.g., time and/or modulation) to increase the safety and the efficacy of the treatment.

In some embodiments, the handle 2404 may comprise a button 2412 configured to start ablation. A foot switch, a software button located on an instrument touch screen, a mouse click, and/or other ablation inciting inputs are possible.

In embodiments comprising an outer sheath, the handle 2404 may comprise a mechanism to proximally retract and/or distally advance the outer sheath (e.g., a second actuator). In some embodiments, the outer sheath may be directly manipulated by the user (e.g., distal to the handle 2404 and/or proximal to the handle 2404).

In some embodiments, the handle 2404 may comprise components for retracting the distal portion of the elongate shaft by a controlled distance between ablation sites, as described in additional detail herein. For example, the handle 2404 may comprise a third actuator. If the handle 2404 comprises a plurality of actuators, the actuators may be labeled with indicia (e.g., letters or numbers), comprise different colors, etc. Preferably, each of the actuators is at least partially different. For example, a plurality of actuators each configured to slide in a path may have different shapes, surface textures, colors, etc. In some embodiments, the actuators are distinguishable by being different types of actuators (e.g., thumb wheel for operation of the outer sheath, slider for deployment of the anchor, knob for controlled retraction of the distal portion, etc.).

Figure 24B:
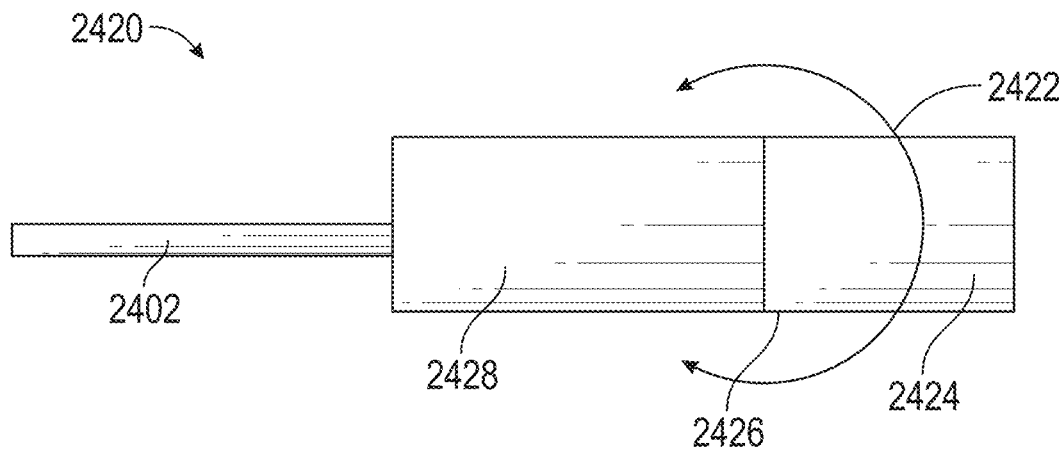
FIG. 24B schematically illustrates another exemplary catheter comprising a handle and an elongate shaft constructed in accordance with the principles of the present disclosure.

FIG. 24B schematically illustrates another example embodiment of a catheter 2420 comprising a handle 2424 and an elongate shaft 2402. The handle 2424 may comprise the features of the handle 2404. The handle 2424 comprises a proximal part 2426 and a distal part 2428. The proximal part 2426 may be rotated relative to the distal part 2428 as shown by the arrow 2422 to advance or retract the distal portion of the catheter 2420 within a vessel. The rotation of the proximal part 2426 is translated into linear motion advancing or retracting the distal portion of the catheter 2420 within a vessel, for example using a helix, a worm gear, rack and pinion, etc. Rotating the proximal part 2426 in one direction advances the distal portion of the catheter 2420, and rotating the proximal part 2426 in the opposite direction retracts the distal portion of the catheter 2420. The handle 2424 may comprise detents to help the user determine an appropriate amount of rotation and thus movement of the distal portion of the catheter 2420. For example, each controlled turn of the proximal part 2426 may proximally retract the distal portion of the catheter a set distance, for example between about 0.25 cm and about 2 cm (e.g., about 0.25 cm, about 0.5 cm, about 1 cm, about 1.5 cm, about 2 cm, and ranges between such values). Distal advancement of the distal portion is also possible.

In some embodiments, the distal portion of the catheter 2420 is advanced to a first target location, such as a distal location in the LPA. The anchor is deployed and the tissue around the first target location is ablated. The anchor is then collapsed and the proximal part 2424 is rotated to proximally retract the distal portion of the catheter 2420, for example by 0.5 cm, to a second target location. The handle 2424 may comprise an interlock that inhibits or prevents rotation of the proximal part 2426 if the anchor is in a deployed state. The anchor is redeployed and the tissue around the second target location is ablated. This collapse, retract (or otherwise move), redeploy, ablate sequence can be repeated for the length of the LPA and then the length of the PT. The distal portion of the catheter 2420 is then advanced to an nth target location, such as a distal location in the RPA (e.g., after user manipulation of a guidewire). The anchor is redeployed and the tissue around the nth target location is ablated. The collapse, retract (or otherwise move such as distally advance), redeploy, ablate sequence can be repeated for the length of the RPA. The handle configurations described herein may be implemented in other catheter systems described herein, e.g., catheter system 100.

Any sequence of treatment of pulmonary arteries is possible. For example: LPA, then PT, then RPA; RPA, then PT, then LPA; LPA, then RPA, then PT; RPA, then LPA, then PT; PT, then RPA, then LPA; PT, then LPA, then RPA. Preferably, the PT is ablated after the LPA or the RPA to reduce navigation. In some embodiments, the PT may be ablated after the LPA and after the RPA.

Figure 25A:
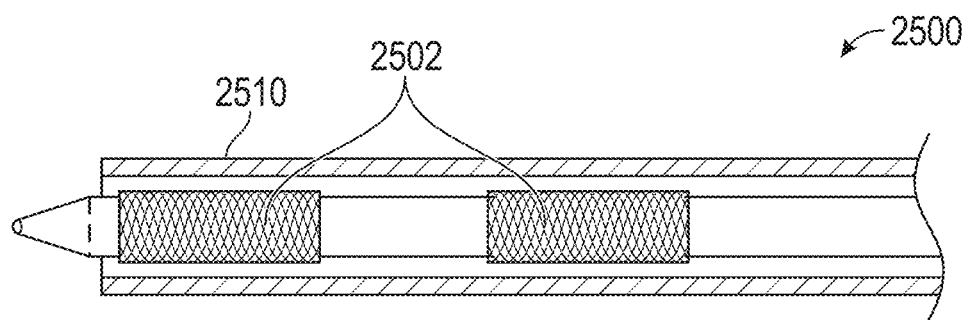
FIG. 25A illustrates another exemplary anchor in a collapsed delivery state constructed in accordance with the principles of the present disclosure.
Figure 25B:
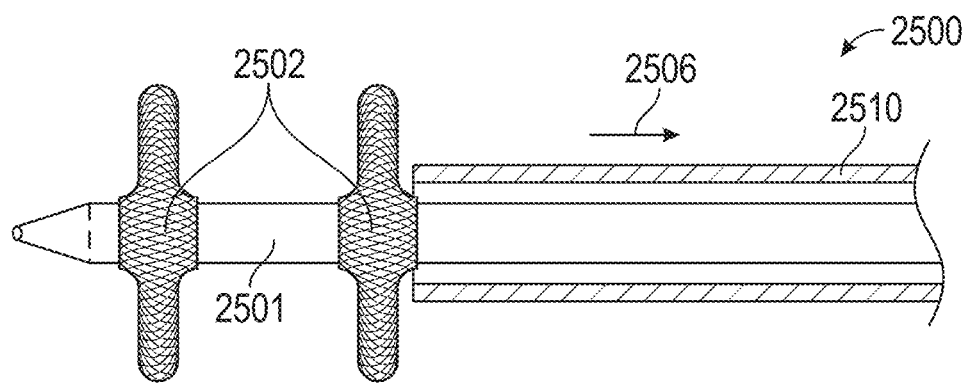
FIG. 25B illustrates the anchor of FIG. 25A in a deployed state.

FIGS. 25A and 25B illustrate another example embodiment of an anchor 2500. FIG. 25A illustrates the anchor 2500 in a collapsed state. In some embodiments, an outer sheath 2510 inhibits or prevents the anchor 2500 from expanding while in the collapsed state. FIG. 25B illustrates the anchor 2500 in a deployed state. The anchor 2500 comprises components on each side of the transducer assembly 2501. The anchor 2500 comprises two braid configurations 2502. Additional braid configurations 2502 are also possible. The first braid configuration 2502 is distal to the transducer assembly 2501, and the second braid configuration 2502 is proximal to the transducer assembly 2501. Braid configurations 2502, for example having a high braid angle, can provide superior radial force compared to a plurality of struts having similar thicknesses, etc.

Figure 26A:
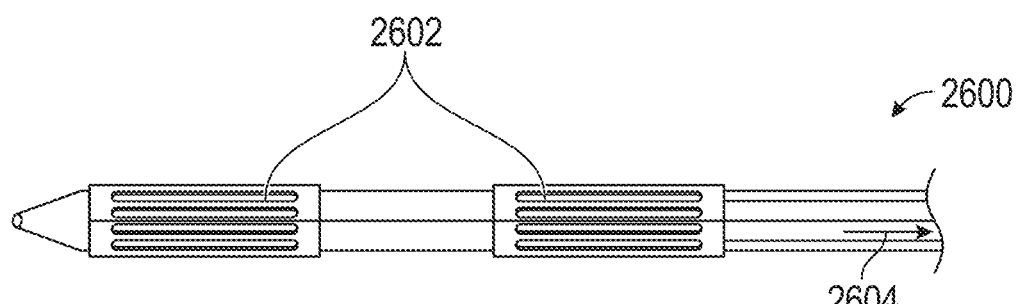
FIG. 26A illustrates another exemplary anchor in a collapsed delivery state constructed in accordance with the principles of the present disclosure.
Figure 26B:
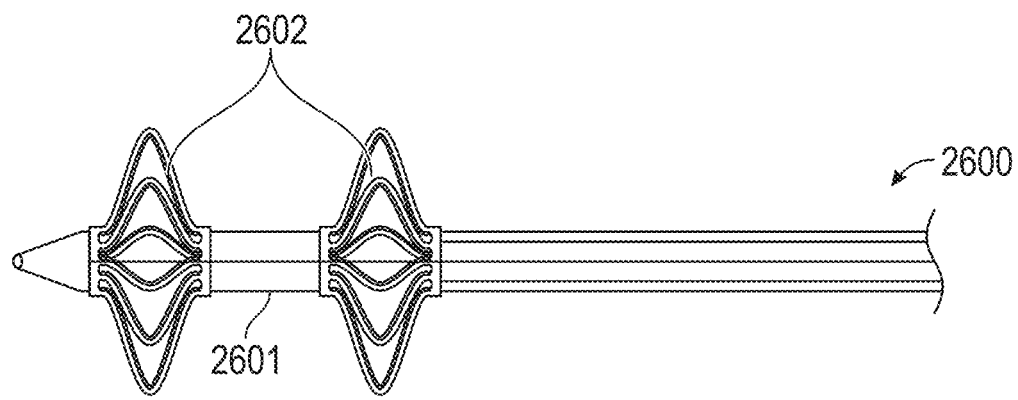
FIG. 26B illustrates the anchor of FIG. 26A in a deployed state.

FIGS. 26A and 26B illustrate another embodiment of an anchor 2600. FIG. 26A illustrates the anchor 2600 in a collapsed state. In some embodiments, an outer sheath inhibits or prevents the anchor 2600 from expanding while in the collapsed state. FIG. 26B illustrates the anchor 2600 in a deployed state. The anchor 2600 comprises a plurality of struts 2602 on each side of the transducer assembly 2601. The anchor 2600 comprises two pluralities of struts 2602. Additional pluralities of struts 2602 are also possible. The plurality of struts 2602 may be configured and operate in any of the ways the plurality of struts 2204 are described herein. For example, the size and shape of the struts 2602 may be any of the embodiments described herein, and the deploying and collapsing of the anchor 2600 may occur in any of the ways described herein. Pluralities of struts 2602 can provide simpler and/or more repeatable manufacturing compared to braid configurations 2502, for example in terms of coupling to proximal and/or distal shafts.

In some embodiments, the anchor 2500, 2600 is deployed by pushing the braid configurations 2502 or the pluralities of struts 2602 together, causing the braid configurations 2502 or the pluralities of struts 2602 to bow radially outwards, as shown in FIGS. 25B and 26B. In some embodiments, the anchor 2500, 2600 is self-expanding. The anchor 2500, 2600 may be collapsed and deployed by moving an outer sheath 2510 (FIGS. 25A and 25B) to cover or expose the anchor 2500, 2600. The outer sheath 2510 is moved in the direction of the arrow 2506 to deploy the anchor 2500, 2600. Additionally or alternatively, the anchor 2500, 2600 may be collapsed and deployed via a pull wire connected to one, some or all of the braid configurations 2502 or the pluralities of struts 2602. The anchor 2500, 2600 deploys when the pull wire(s) are pulled, and the anchor 2500, 2600 collapses when the pull wire(s) are advanced. In addition to or alternative to a pull wire, a shaft or tube could be used to push and/or pull a proximal and/or distal part of an anchor to deploy and/or collapse the anchor. In some embodiments, the pull wire(s) may be biased towards the collapsed state for a fail-collapsed configuration. In some embodiments, the fail-collapsed configuration could be achieved by heat shaping the anchor in the collapsed configuration. In certain such embodiments, a push mechanism could be used to achieve the deployed configuration. The anchor may be actuated and/or kept actuated by a wheel locker in a handle. Being fail-collapse can collapse the anchor upon failure (e.g., of the wire, shaft, etc.) while deployed in the subject.

Figure 27A:
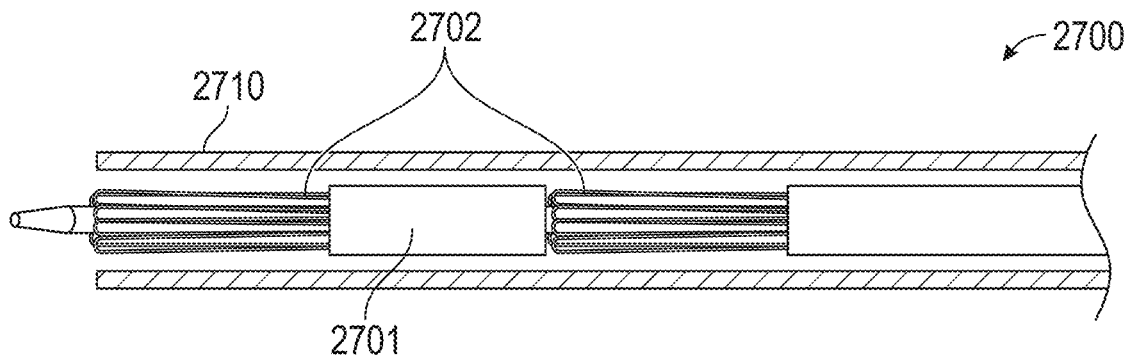
FIG. 27A illustrates another exemplary anchor in a collapsed delivery state constructed in accordance with the principles of the present disclosure.
Figure 27B:
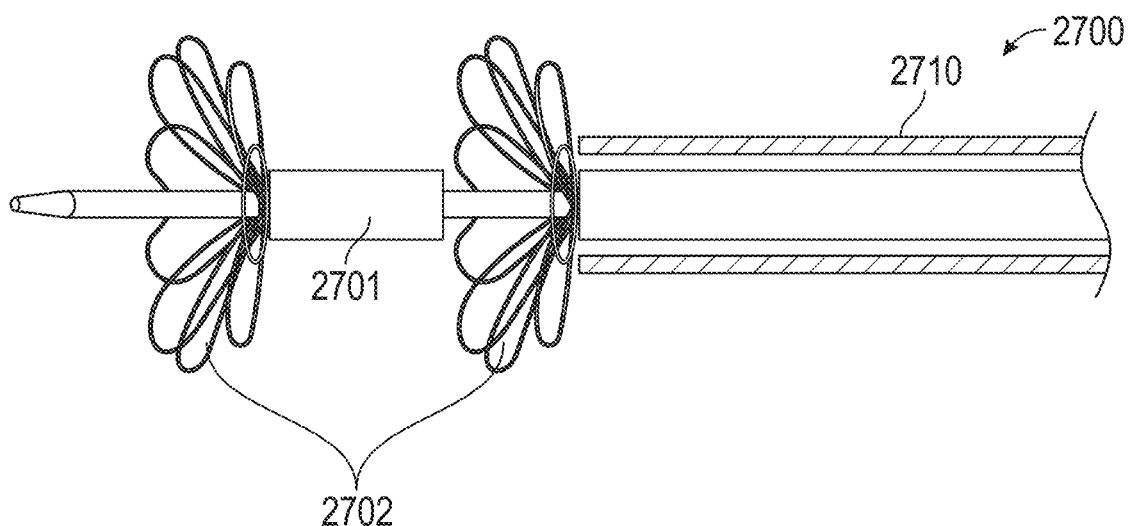
FIG. 27B illustrates the anchor of FIG. 27A in a deployed state.

FIGS. 27A to 27D illustrate another embodiment of an anchor 2700. FIG. 27A illustrates the anchor 2700 in a collapsed state. In the embodiment illustrated in FIG. 27A, the outer sheath 2710 is inhibiting or preventing the anchor 2700 from radially expanding, for example causing stress-induced martensite. FIG. 27B illustrates the anchor 2700 in a deployed state. When the petal configurations 2702 are not confined by the outer sheath 2710, the anchor 2700 can self-expand due to a phase change to austenite. The anchor 2700 comprises a petal configuration 2702 on each side of the transducer assembly 2701. The anchor 2700 comprises two petal configurations 2702. Additional petal configurations 2702 are also possible.

The petal configurations 2702 comprise one or more wires shaped as a flower with multiple petals 2706. The petals 2706 may circumferentially overlap. The wire(s) may be shape set in the deployed state so that the petal configurations 2702 are self-expanding. In some embodiments, the anchor 2700 includes a float section (e.g., a segment generally parallel to the longitudinal axis) at the tip of the petals to increase the contact surface between the anchor 2700 and the vessel wall. The increase in contact surface may reduce the radial force applied to the vessel wall while still achieving the same anchoring (e.g., providing a substantially constant transducer assembly 2701 position under the same forces such as blood flow).

The anchor 2700 may be configured in multiple orientations. The petal configurations 2702 may be oriented to open facing the distal portion of the catheter, for example as shown in FIG. 27B. The petal configurations 2702 may be configured to face the handle (e.g., as described herein) of the catheter, for example as shown in FIGS. 27A to 27D. The petal configurations 2702 may be configured to face each other. The petal configurations 2702 may be configured to face away from each other.

The anchor 2700 may be self-expanding. The anchor 2700 may be collapsed and deployed by moving an outer sheath 2710 to cover or expose the petal configurations 2702. In some embodiments, the anchor 2700 is collapsed and deployed via a pull wire. If a petal configuration 2702 faces the handle, a pull wire may be used to collapse the petal configuration 2702 that is not collapsible by an outer sheath 2710 due to the direction the petal configuration 2702 is facing.

Figure 27C:
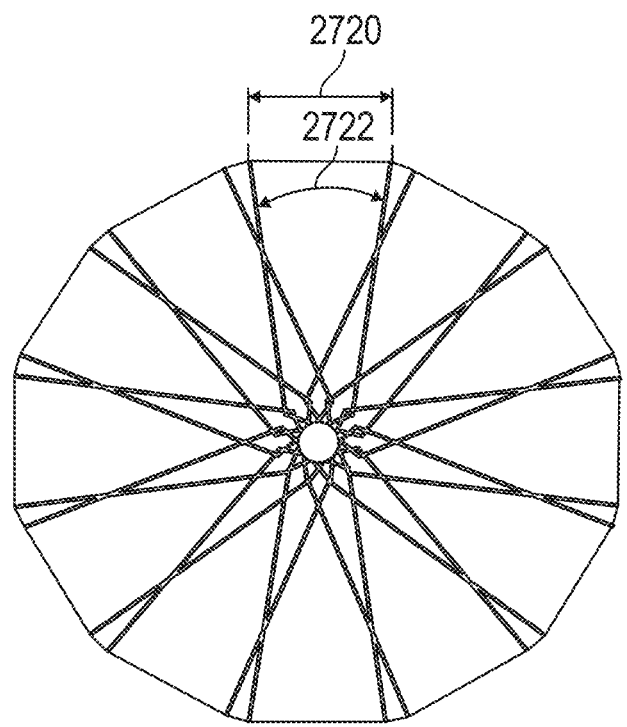
FIG. 27C is a top view of an exemplary petal configuration for the anchor of FIG. 27A.

FIG. 27C is a top view of an example petal configuration for the anchor 2700 of FIG. 27A. The petals may have a circumferential width 2720 between about 5 mm and about 15 mm (e.g., about 5 mm, about 7 mm, about 9 mm, about 11 mm, about 13 mm, about 15 mm, and ranges between such values). The base of the petal configurations may be configured to create angles 2722 of between about 10 degrees and about 20 degrees (e.g., about 10 degrees, about 12 degrees, about 14 degrees, about 16 degrees, about 18 degrees, about 20 degrees, and ranges between such values).

Figure 27D:
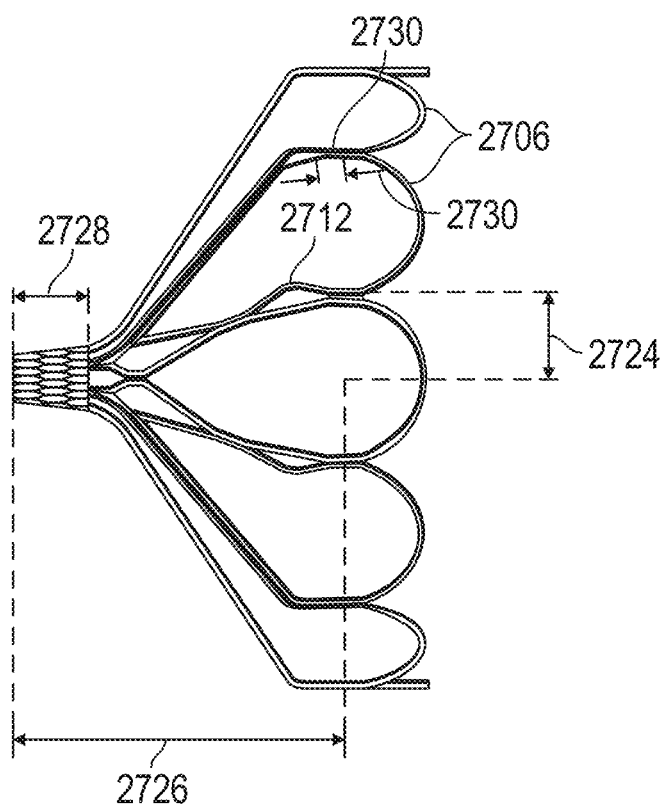
FIG. 27D is a side view of the petal configuration of FIG. 27C.

FIG. 27D is a side view of the example petal configuration of FIG. 27A. The top portion of the petals may have a radius 2724 between about 1 mm and about 8 mm (e.g., about 1 mm, about 2 mm, about 3 mm, about 4 mm, about 5 mm, about 6 mm, about 7 mm, about 8 mm, and ranges between such values). The distance 2726 between the base of the petal configuration and the center of the diameter of the petals may be between about 12 mm and about 20 mm (e.g., about 12 mm, about 14 mm, about 16 mm, about 18 mm, about 20 mm, and ranges between such values). The distance 2728 between the base of the petal configuration and start of the petals may be between about 2 mm and about 8 mm (e.g., about 2 mm, about 3 mm, about 4 mm, about 5 mm, about 6 mm, about 7 mm, about 8 mm, and ranges between such values). The distance 2730 between the angle portion of the petal and the start of the arc of the petal may be between about 0.5 mm and about 2.5 mm (e.g., about 0.5 mm, about 1 mm, about 1.5 mm, about 2 mm, about 2.5 mm, and ranges between such values).

The anchors 2500, 2600, 2700 can apply a radial force on the vessel wall to anchor the transducer assembly 2501, 2601, 2701 within the vessel. The anchor 2500, 2600, 2700 is configured to conform to the different diameters of the vessels, as described herein. For example, the PT is typically larger in diameter than the LPA and RPA and the anchor 2500, 2600, 2700 expands according to the diameter of the ablation site. Depending on the diameter of the vessel, it may not be possible to achieve the delivery states shown in FIGS. 8B, 9B, and 10B, but expansion of the anchor 2500, 2600, 2700 such that the anchor 2500, 2600, 2700 is able to maintain a substantially constant position of the transducer assembly 2501, 2601, 2701 in the vessel may be considered the deployed state. Ablation preferably occurs when the anchor 2500, 2600, 2700 is in the deployed state, or is not in the delivery state.

The anchors 2500, 2600, 2700 are proximal and distal to the transducer assemblies 2501, 2601, 2701, respectively. The anchors 2500, 2600, 2700 do not longitudinally overlap with the transducer assemblies 2501, 2601, 2701 and do not cast shadows, scatter acoustic energy, or otherwise block ablation energy. The anchors 2500, 2600, 2700 can allow a single ablation without rotation because the ablation energy can be circumferential and not blocked.

FIGS. 25A and 25B illustrate two braid configurations 2502, FIGS. 26A and 26B illustrate two pluralities of struts 2602, and FIGS. 27A to 27D illustrate two petal configurations 2702, but some embodiments of anchors may comprise any number of braid configurations, pluralities of struts, petal configurations, combinations thereof, and/or the like. For example, an anchor may comprise one braid configuration and one plurality of struts, one braid configuration and one petal configuration, or one plurality of struts and one petal configuration, for example to provide certain benefits of each type of anchor.

Figure 28A:
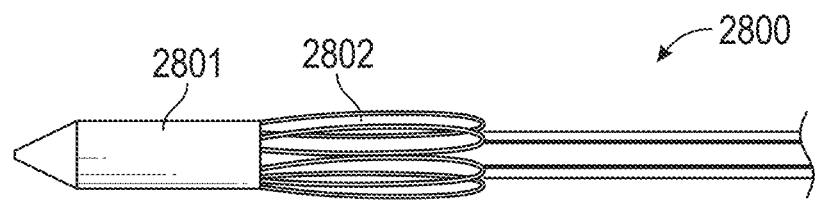
FIG. 28A illustrates another exemplary anchor in a collapsed delivery state constructed in accordance with the principles of the present disclosure.
Figure 28B:
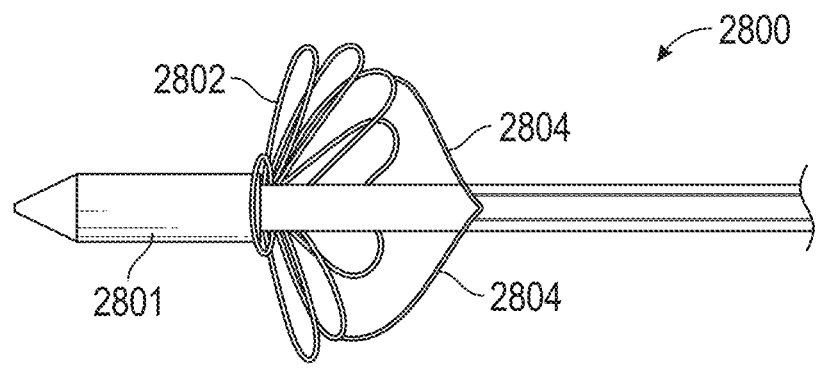
FIG. 28B illustrates the anchor of FIG. 28A in a deployed state.

FIGS. 28A to 28D illustrate another embodiment of an anchor 2800. FIG. 28A illustrates the anchor 2800 in a collapsed state. FIG. 28B illustrates the anchor 2800 in a deployed state. The anchor 2800 comprises one petal configuration 2802. The petal configuration 2802 may be configured in any of the described embodiments of petal configurations 2702.

Figure 28C:
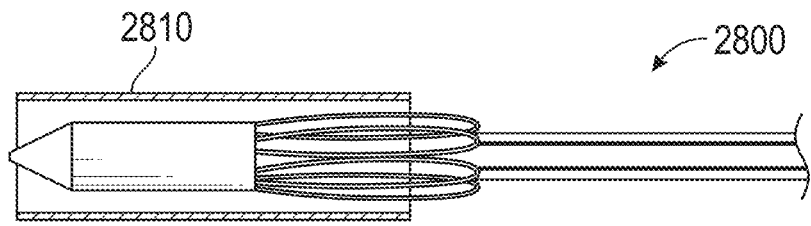
FIG. 28C illustrates another exemplary anchor in a collapsed delivery state constructed in accordance with the principles of the present disclosure.
Figure 28D:
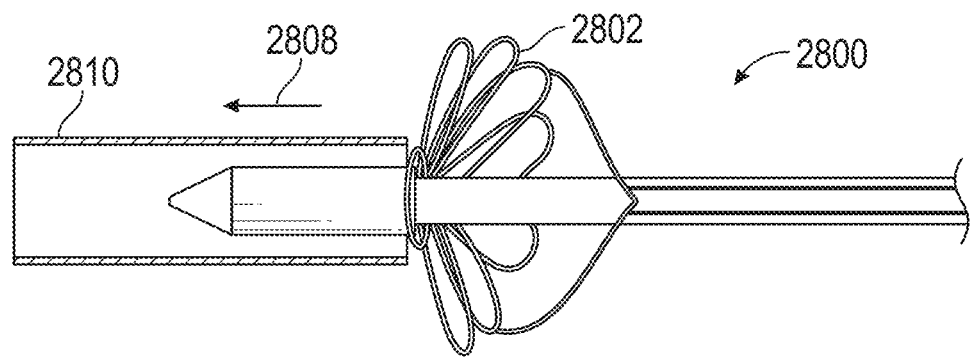
FIG. 28D illustrates the anchor of FIG. 28C in a deployed state.

The anchor 2800 can be configured with the petal configuration 2802 facing proximally. When the petal configuration 2802 is proximal to the transducer assembly 2801, the petal configuration 2802 faces away from the transducer assembly 2801 (e.g., as shown in FIG. 28B). When the petal configuration 2802 is distal to the transducer assembly 2801, the petal configuration 2802 faces towards the transducer assembly 2801. The anchor 2800 may be deployed and collapsed via an outer sheath 2810 and/or pull wire(s) 2804 connected to one, some, or all of the petals of the petal configuration 2802. If the pull wire(s) 2804 is not connected to all petals, the overlapping of the petals can cause all petals to be collapsed when the pull wire 2804 is pulled. FIGS. 28C and 28D illustrate the use of an outer sheath 2810 to deploy and collapse the anchor 2800. The outer sheath 2810 is positioned on the distal portion of the catheter. The outer sheath 2810 is distally advanced in the direction of the arrow 2808 to allow the anchor 2800 to expand to the deployed state. The outer sheath 2810 is then proximally retracted to collapse the anchor 2800.

Figure 29A:
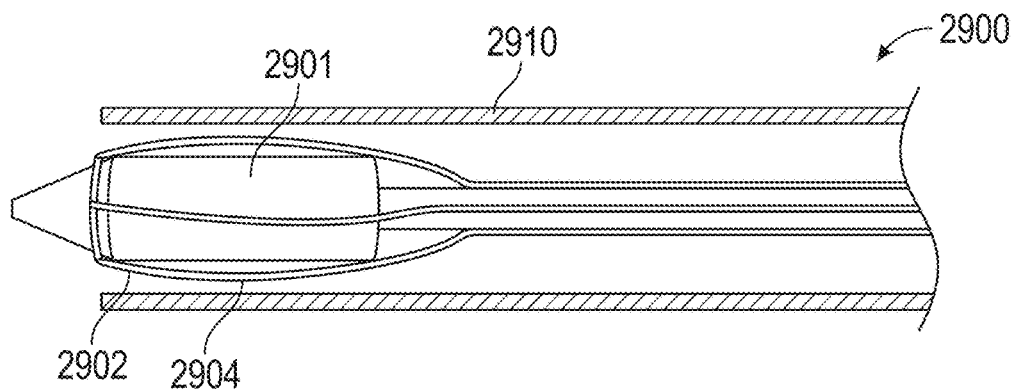
FIG. 29A illustrates another exemplary anchor in a collapsed delivery state constructed in accordance with the principles of the present disclosure.
Figure 29B:
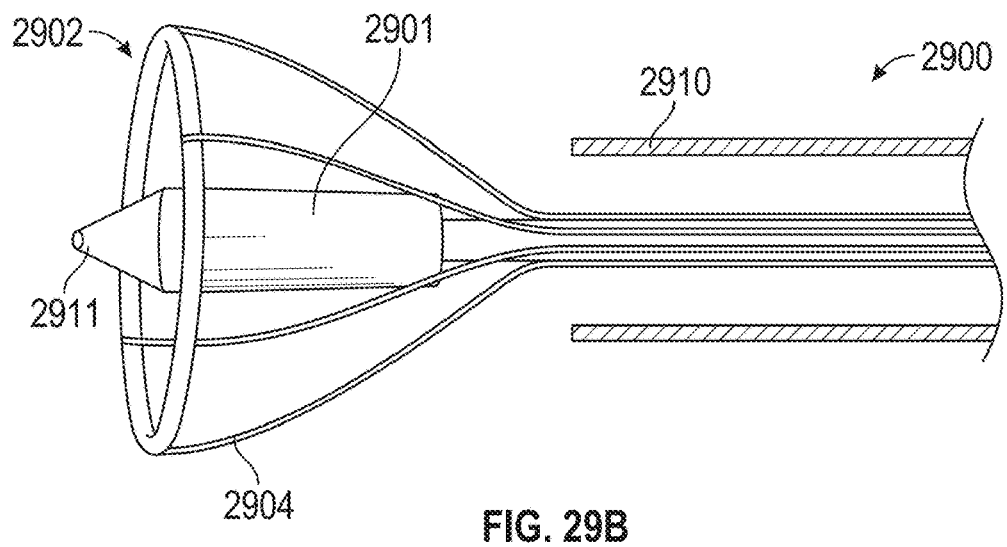
FIG. 29B illustrates the anchor of FIG. 29A in a deployed state.

FIGS. 29A and 29B illustrate another embodiment of an anchor 2900. FIG. 29A illustrates anchor 2900 in a collapsed state. In the embodiment illustrated in FIG. 29A, outer sheath 2910 is inhibiting or preventing anchor 2900 from radially expanding. For example, anchor 2900 may include ring balloon 2902 coupled to a plurality of self-expanding struts 2904. Struts 2904 may be coupled to ring balloon 2902 at equally spaced locations along the circumference of ring balloon 2902. FIG. 29B illustrates anchor 2900 in a deployed state. When ring balloon 2902 and struts 2904 are not confined by outer sheath 2910, struts 2904 may self-expand. In addition, ring balloon 2902 may be inflated, e.g., via an inflation lumen extending through one of the struts of plurality of struts 2904, to fully deploy anchor 2900 such that ring balloon 2902 contacts the inner wall of the blood vessel, to thereby centralize transducer 2901 within the blood vessel. Accordingly, the distance between tip 2911 and transducer 2901 may be minimized, and transducer 2901 further may be positioned visually without additional movement during anchor deployment. Moreover, anchor 2900 is coincident with the location of transducer 2901.

Figure 30A:
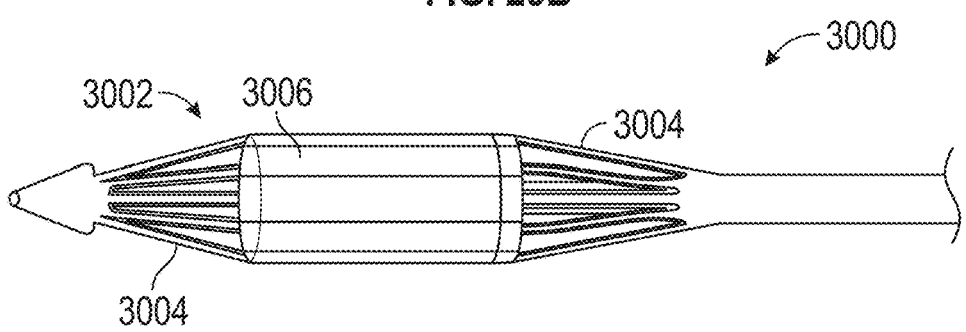
FIG. 30A illustrates another exemplary anchor in a collapsed delivery state constructed in accordance with the principles of the present disclosure.
Figure 30B:
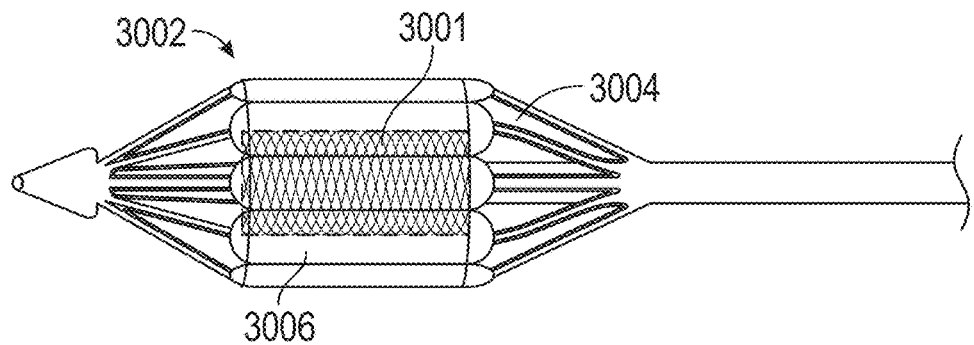
FIG. 30B illustrates the anchor of FIG. 30A in a deployed state.

FIGS. 30A and 30B illustrate another embodiment of an anchor 3000. FIG. 30A illustrates anchor 3000 in a collapsed state. Anchor 3000 includes a plurality of individually inflatable balloons 3002, each coupled to a respective struts of a plurality of struts 3004. Struts 3004 may each include an inflation lumen for inflating balloons 3002. Moreover, anchor 3000 includes sleeve 3006 circumferentially wrapped around balloons 3002. FIG. 30B illustrates anchor 3000 in a deployed state. For example, anchor 3000 may be delivered to the target blood vessel within a delivery sheath, such that upon retraction of the sheath to expose anchor 3000, balloons 3002 may be inflated, as shown in FIG. 30B, to thereby centralize transducer 3001 within the blood vessel. In the deployed state, sleeve 3006 contacts the inner wall of the blood vessel, and blood is permitted to flow across anchor 3000 between balloons 3002 and transducer 3001. Moreover, transducer 3001 may be positioned visually without additional movement during anchor deployment, and anchor 3000 is coincident with the location of transducer 3001.

Figure 31A:
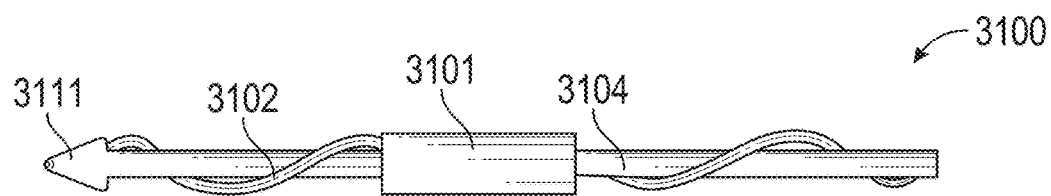
FIG. 31A illustrates another exemplary anchor in a collapsed delivery state constructed in accordance with the principles of the present disclosure.
Figure 31A:
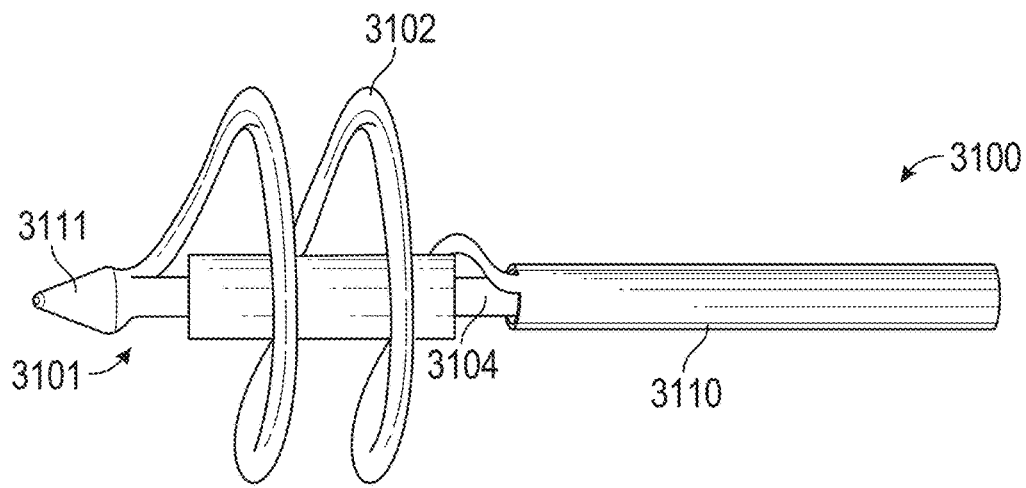

FIGS. 31A and 31B illustrate another embodiment of an anchor 3100. FIG. 31A illustrates anchor 3100 in a collapsed state. Anchor 3100 includes coil 3102 circumferentially wrapped around the longitudinal axis of anchor 3100. A distal end of coil 3102 may be coupled to tip 3111 disposed at the end of inner catheter 3104, and a proximal end of coil 3102 may be coupled to the distal end of outer catheter 3110, wherein inner catheter 3104 is slidably movable within outer catheter 3110. Accordingly, relative movement between inner catheter 3104 and outer catheter 3110 may cause coil 3102 to transition between a collapsed state, as shown in FIG. 31A, and a deployed state, as shown in FIG. 31B, by moving the proximal and distal ends of coil 3102 toward and away from each other. In some embodiments, coil 3102 may be self-expanding, e.g., biased toward the deployed state. Moreover, transducer 3101 may be positioned visually without additional movement during anchor deployment, and anchor 3100 is coincident with the location of transducer 3101.

Figure 32A:
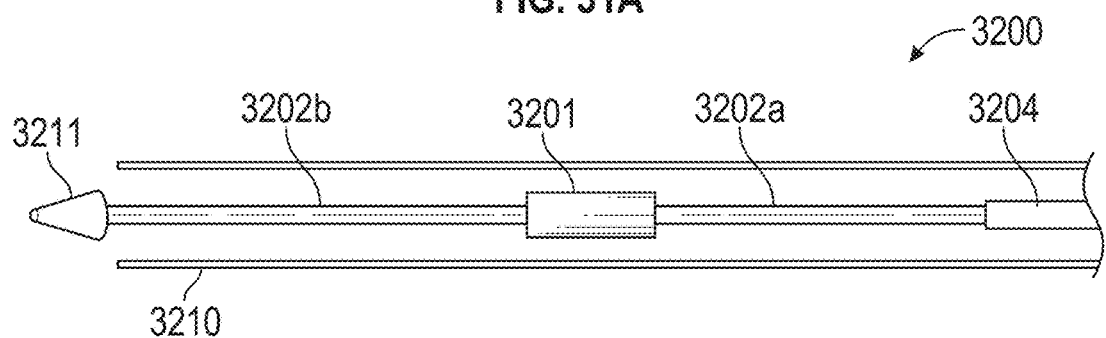
FIG. 32A illustrates another exemplary anchor in a collapsed delivery state constructed in accordance with the principles of the present disclosure.
Figure 32B:
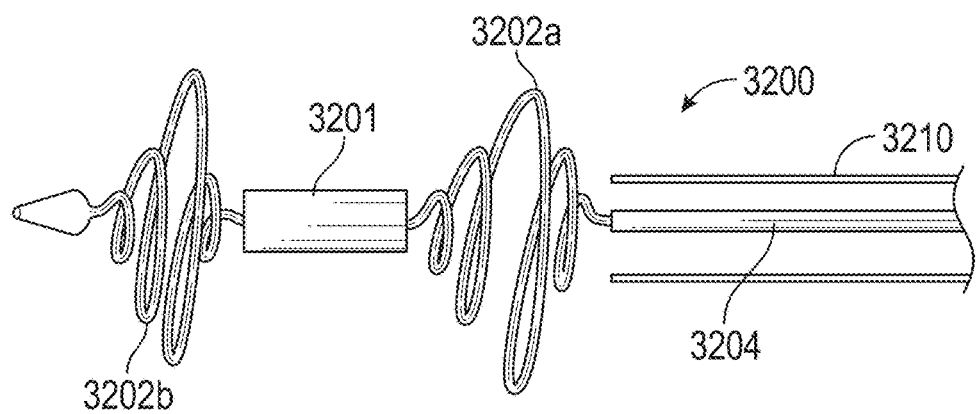
FIG. 32B illustrates the anchor of FIG. 32A in a deployed state.

FIGS. 32A and 32B illustrate another embodiment of an anchor 3200. FIG. 32A illustrates anchor 3200 in a collapsed state. In the embodiment illustrated in FIG. 32A, outer sheath 3210 is inhibiting or preventing anchor 3200 from radially expanding. For example, anchor 3200 may include proximal coil 3202*a* disposed between catheter 3204 and transducer 3201, and distal coil 3202*b* disposed between tip 3211 and transducer 3201. Proximal coil 3202*a* and distal coil 3202*b* may be formed of a shape memory metal, e.g., Nitinol, such that proximal coil 3202*a* and distal coil 3202*b* are biased toward the expanded state. Upon retraction of sheath 3210, proximal coil 3202*a* and distal coil 3202*b* may transition to the expanded state, as shown in FIG. 32B, to thereby centralize transducer 3201 within the blood vessel.

FIGS. 33A to 33D illustrate another embodiment of an anchor 3300. The anchor 3300 comprises a loop wire 3302.

The anchor 3300 may comprise one, two, or more loop wires 3302. FIGS. 33C and 33D illustrate the loop wire 3302. FIG. 33A illustrates the anchor 3300 in a collapsed state. An outer sheath as described herein may be used to inhibit or prevent the anchor 3300 from expanding. FIG. 33B illustrates the anchor 3300 in a deployed state.

The loop wires 3302 may be positioned distal and proximal of transducer assembly 3303 anchor the transducer assembly 3303 in a vessel. In embodiments comprising a single loop wire 3302, the loop wire 3302 may be located distal to or proximal to the transducer assembly 3303. In some embodiments, the loop wire 3302 is self-expanding and can be actuated by pushing the wire (e.g., one or both legs) from the proximal side of the catheter. The loop wire 3302 is then collapsed by pulling the wire.

All embodiments of the anchor described herein may be modified and combined to create additional embodiments. For example, all embodiments may consist of one, two, three or four anchors. In embodiments comprising more than one anchor, the anchors may be of different types. For example, one embodiment of an anchor may comprise a plurality of struts and a braid configuration. Any combination of the disclosed embodiments may be possible. All methods of deploying and collapsing the different anchor embodiments may apply to any of the anchor embodiments, including but not limited to, the umbrella method, the movement of an outer sheath, the use of a pull wire, the use of actuating shafts (e.g., telescoping shafts), and the use of self-expanding material. In embodiments in which neuromodulation is provided by, for example, acoustic energy (e.g., ultrasound), microwave energy, radiofrequency (RF) energy, thermal energy, electrical energy, infrared energy, laser energy, phototherapy, plasma energy, ionizing energy, mechanical energy, cryoablation, chemical energy, combinations thereof, and the like, the anchor may optionally push the transducer or other element against the vessel wall.

Figure 34A:
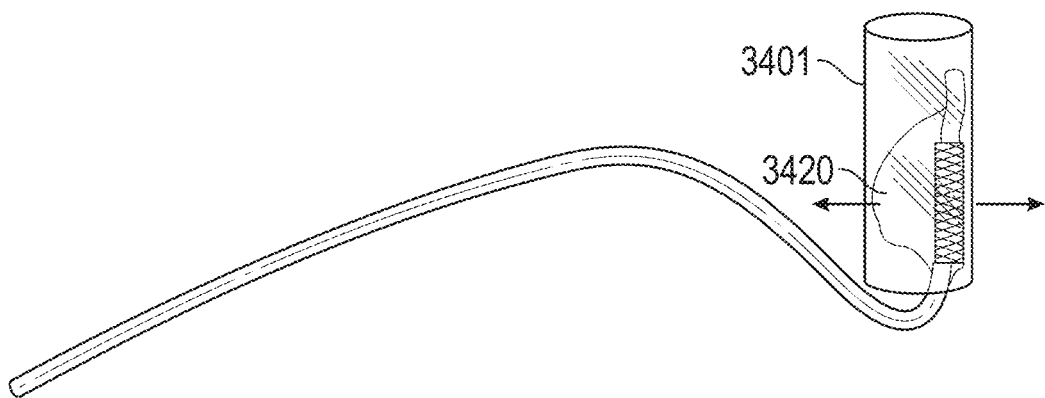
FIG. 34A illustrates an exemplary catheter in a vessel that is not properly anchored.

As described above, the distal portion of the catheter system (e.g., distal region 104 of catheter system 100) is flexible enough to navigates a variety of vessels, and cavities such as heart chambers, and rigid enough to be advanced through valves such as the tricuspid valve and the pulmonary valve. This combination of flexibility and rigidity may cause undesirable effects when the distal portion is anchored ablation. FIG. 34A illustrates an example catheter in a vessel 3401 that is not properly anchored. As shown in FIG. 34A, the transducer assembly 3420 is supposed to be anchored for ablation. The curvature of the catheter proximate to the anchor pushes the transducer assembly 3420 to the right side because the radial force of the anchor is not able to overcome the force of the catheter.

Figure 34B:
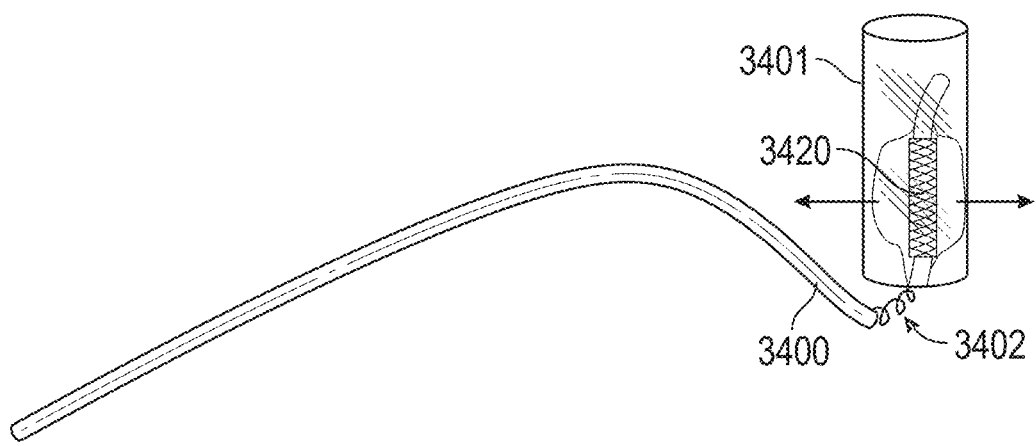
FIG. 34B illustrates an exemplary catheter in which the stiffness of a shaft can be effectively negated proximate a distal portion.

FIG. 34B illustrates an example embodiment of a catheter in which the stiffness of the shaft 3400 can be effectively negated proximate the distal portion. To reduce the impact of the shaft 3400 stiffness, some embodiments comprise a suspension 3402. The suspension 3402 may comprise a coil or other type of flexible shaft portion configured to release some of the constraints due to the shaft 3400 stiffness and curvature proximate the distal portion. The suspension 3402 is more flexible then the shaft 3400, which can allow the distal portion to effectively ignore the forces of the shaft 3400, which are absorbed by the suspension 3402. The suspension 3402 can provide better anchoring and centering of the transducer assembly 3420. The suspension 3420 may comprise any suitably flexible material.

Figure 35A:
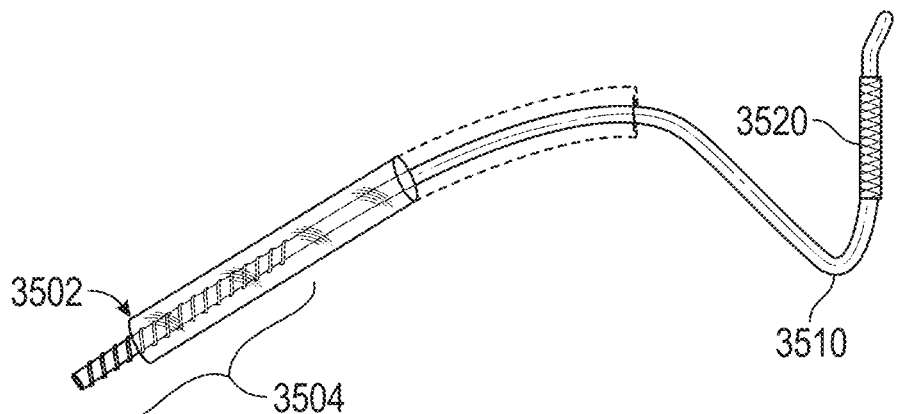
FIG. 35A illustrates an exemplary retraction feature constructed in accordance with the principles of the present disclosure.

The distal portion of the catheter system (e.g., distal region 104 of catheter system 100) may be navigated through vessels to multiple ablation sites. The distance between ablation sites may be controlled (e.g., as described with respect to the handle 2424 and/or handle 300') and/or monitored. The movement (e.g., retraction, advancement) features described herein may be used to monitor the distance between ablation sites. FIG. 35A illustrates a distal portion of a catheter comprising a shaft 3510 and a transducer assembly 3520. The catheter is configured to enter the patient at a vein access point 3502. Vein access points include but are not limited to femoral, jugular, and radial access points. Any suitable vein access point may be used.

The shaft 3510 may comprise electrodes 3504 located along a proximal portion of the shaft 3510. The electrodes 3504 are configured to sense the electrical conduction between each electrode to determine the distance the transducer assembly 3520 was pulled or pushed from an ablation site. In some embodiments, the conduction between a first set of electrodes are high impedance, while the conduction between the rest of the electrodes is low impedance. A variance between low and high impedance may be used to account for the electrical conductivity of the blood that is in contact with the electrodes positioned within the body. For example, the electrodes 3504 outside the vein access point 3502 in FIG. 35A will have a high impedance, while the electrodes 3504 within the vein will have a lower impedance.

In some embodiments, the electrodes 3504 are located at fixed points along the shaft 3510. The fixed locations allow software running on an instrument (e.g., as described herein) to detect the number of electrodes 3504 moved in or out of the body. Tracking the movement of electrodes 3504 may be used to determine the approximate distance between positions of the transducer assembly 3520 and the different ablation sites. In some embodiments, data about the transducer assembly position, diameter of the deployed anchor, and/or ablation parameters can be stored. A report can be produced. Reports from the treatment of various subjects can be combined with data about the effectiveness of the treatment for those subjects to improve the system (e.g., determining ideal ablation spacing, ablation parameters, etc.). Embodiments comprising electronics may comprise interlocks, for example inhibiting or preventing an ablation until the catheter has been moved to a different ablation site.

Figure 35B:
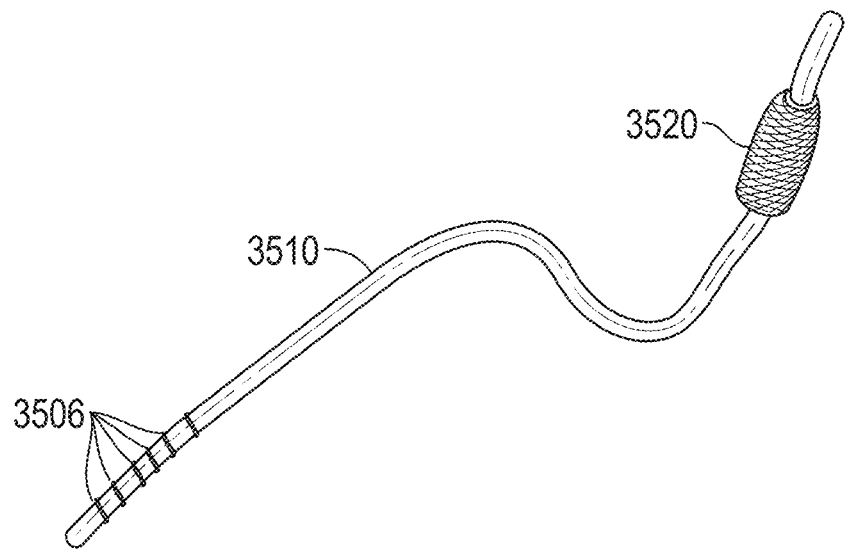
FIG. 35B illustrates another exemplary retraction feature constructed in accordance with the principles of the present disclosure.

FIG. 35B illustrates another example embodiment of movement (e.g., retraction, advancement) features. The shaft 3510 comprises marks or indicia 3506. Any number of marks 3506 along the shaft 3510 can be used. The marks 3506 can be separated any distance, for example every half centimeter. The marks 3506 allow the operator to control and monitor the distance between two ablation sites when pulling or pushing the catheter. For example, the marks 3506 may be compared to a stationary object (e.g., an access point). Some embodiments may include additional and/or alternative methods to control the distance between two ablation sites when pulling or pushing the catheter. For example, an actuator (e.g., the actuator 2406 and/or pusher 1200) may be configured to push or pull the catheter a specified distance with each actuation. For another example, magnetic beacons can be used. For another example, a wheel with appropriate gearing can be used.

In some embodiments, the movement (e.g., retraction, advancement) feature may comprise radiopaque markers on the distal portion of the catheter that can be observed under fluoroscopy. Such a movement feature may provide the ability to make sure that the movement of the catheter (e.g., by manipulating a handle) translates into the expected or desired movement in the vessel. Fluoroscopy can also or alternatively be used in combination with any of the movement features described herein.

Figure 36:
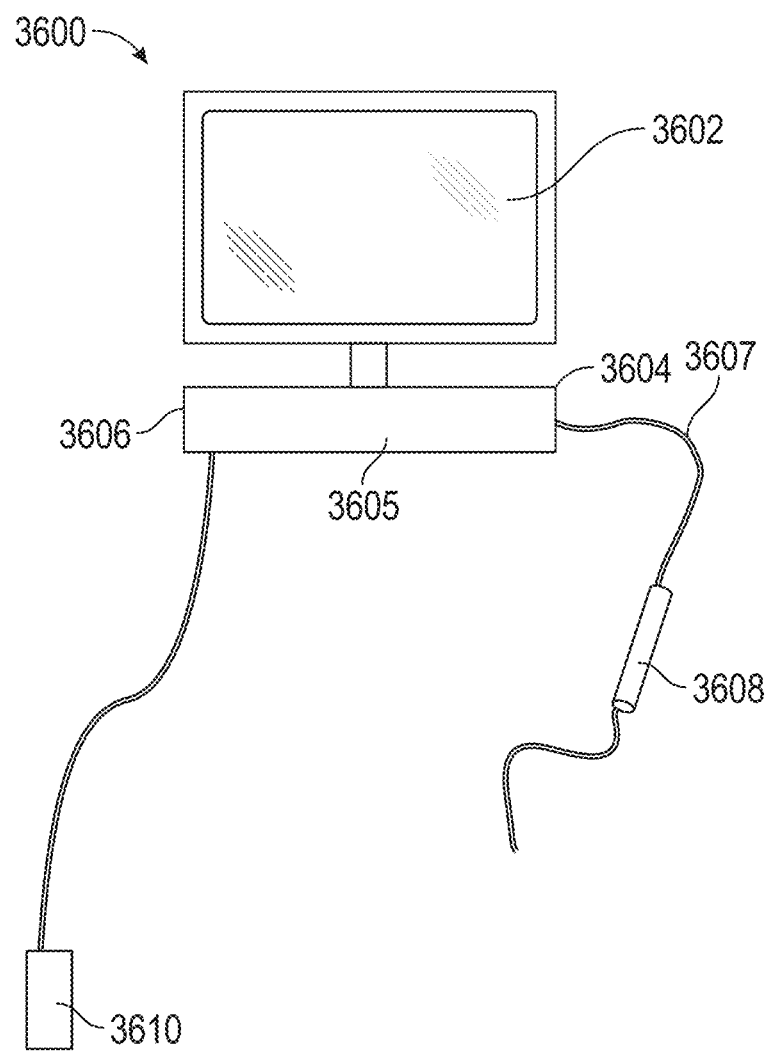
FIG. 36 is a schematic diagram of an example ablation instrument in accordance with the principles of the present disclosure.

FIG. 36 is a schematic diagram of an example ablation instrument 3600. The instrument 3600 serves as the user interface and provides the electrical power to a catheter 3608, e.g., catheter system 100. The instrument 3600 includes a display screen 3602, an ultrasound beam generator 3604, a power monitor 3605, a control computer 3606, a removable catheter connector 3607 between the control computer 3606 and a catheter 3608, and a foot pedal 3610 that may be used to initiate ablation. The display screen 3602 may be a touch screen. The instrument 3600 may comprise other inputs (e.g., a mouse, a keyboard, a track ball, etc.).

The ultrasound beam generator 3604 comprises an electrical power amplifier with an output between 1.5 MHz to 11 MHz capable of 200 Watts or more of electrical power in continuous wave mode or in pulse wave mode. The ultrasound beam generator 3604 supports a programmatic interface, for example through an internal USB to Serial port interface. The interface allows the control computer 3606 to start or stop the ultrasound emission. The ultrasound beam generator 3604 can embed a firmware in charge of the pulse emission communication with the control computer 3604 to check internal devices such as temperature sensors (e.g., as described herein), fans, etc.

The tissue around the pulmonary artery, which may include nerves, can be ablated by applying ultrasound energy to the transducer, which is focused by the lens. The energy can be applied for a duration between about 0.5 seconds and about 1 minute (e.g., about 0.5 seconds, about 1 second, about 2 seconds, about 3 seconds, about 4 seconds, about 5 seconds, about 6 seconds, about 7 seconds, about 8 seconds, about 9 seconds, about 10 seconds, about 15 seconds, about 30 seconds, about 45 seconds, about 1 minute, and ranges between such values).

The energy can be between about 20 Watts (W) and about 80 W acoustic (e.g., about 20 W, about 30 W, about 40 W, about 50 W, about 60 W, about 70 W, about 80 W, and ranges between such values). The acoustic wattage is at least partially based on electric power applied and the efficiency of the system such as the transducer assembly. For example, if the system is 50% efficient, the application of 40 W electric would be 20 W acoustic. If transducer assemblies are between about 50% and about 80% efficient, then the electrical power applied can be between about 25 W and about 160 W to produce between about 20 W and about 80 W acoustic.

Although described herein with respect to ultrasound, other energy modalities are also provided, for example unfocused ultrasound, focused ultrasound such as high-intensity or low-intensity focused ultrasound, microwave energy, radiofrequency (RF) energy (e.g., monopolar, bipolar, etc.), thermal energy (e.g., cryoenergy, heat or cold provided by a fluid (e.g., water, saline, liquid medicament, etc.) or gas (e.g., steam)), electrical energy (e.g., non-RF electrical energy), infrared energy, laser energy, phototherapy or photodynamic therapy (e.g., in combination with one or more activation agents), plasma energy, ionizing energy delivery (e.g., X-ray, proton beam, gamma rays, electron beams, alpha rays, etc.), mechanical energies delivered by cutting or abrasive elements, cryoablation, chemical energy or modulation (e.g., chemoablation), or combinations thereof. In some embodiments, disruption or interruption of nerves is carried out by chemicals or therapeutic agents (for example, via drug delivery), either alone or in combination with an energy modality. In some embodiments, pharmaceuticals are combined with the neuromodulation (e.g., ablation) described herein to reduce the dosage or duration of pharmacology therapy, thus reducing side effects. In various embodiments, different energy modalities may be used in combination (either simultaneously or sequentially).

The power monitor 3605 measures the electrical power using a directional coupler. The directional coupler comprises two coils with ferrite to measure power without inducing a loss due to measurement. The power monitor 3605 measures the power being sent to the transducer (forward power) and the power being reflected back (reverse power). The forward or the reverse power are measured through an Analog to Digital Converter that are read in real-time by the control computer through an internal USB interface.

The efficiency and natural frequency of each catheter, transducer, and/or transducer assembly may be measured prior to use, for example by the manufacturer, another facility, an independent company, and/or the like.

During the ablation procedure, the user inputs the efficiency and the natural frequency of the transducer being used. Each system can include an indicator of the efficiency of that particular system so that the ultrasound beam generator can account for losses to deliver the appropriate acoustic energy. The indicator may be a fact sheet that is input by a user. The fact sheet may be a sticker on the box, on the instructions for use, on a sterile wrapper, on a package insert, and/or the like. The indicator may be a bar code or QR code that may be read by an appropriate device. The indicator may be embedded in a flash memory such as an EPROM that can be automatically read by the ultrasound beam generator when the catheter 3608 is coupled to the connector 3607. The memory may be in a USB stick, a SD card, or other hard media that may be required to be inserted in the control computer 3606 for the system to function. The beam generator can use information from the indicator to ensure that a catheter is not reused for multiple procedures (e.g., at all, unless a user indicates appropriate sterilization, etc.). A simpler indicator may reduce costs. A more complicated indicator can reduce the risk of user error.

During use, the power monitor 3605 will monitor the reverse power (unused power that is reflected back) and compare it to the expected results from the inputted data. If the reverse power losses are calculated as being too high or indicate a broken transducer (or any problem with the transducer), the procedure can be stopped. For example, if there is too much reverse power, the energy is not converted into acoustic and therefore the system is in some variety of failure (e.g., broken cable linking generator and transducer, solder failure, too many bubbles reflecting the power back to the source, parasitic capacitance, etc.).

The control computer 3606 is configured to assist the user during a procedure. The control computer 3606 controls the user interface, drives the power generator, and controls the power output. For example, the control computer 3606 may be loaded with data from a planning tool to assist in ablation. This data may comprise ablation site positions, diameters of the vessels, distances between ablation sites, etc. The preloaded data may comprise data that was previously collected via CT scan images, MRIs, IVUS, or other medical scans, images, tests of the patient, etc. By knowing this information prior to the procedure, the user may define the diameter of the artery at the ablation site using the control computer 3606 to set or optimize the acoustic power and the pulse duration. After the initial phase of positioning the catheter, the treatment may then be automatically monitored using the electrodes, described herein, to generate a treatment report.

The treatment report may include a report of the power delivered at each ablation site. A report of the power delivered will increase the user's overall efficiency and capability from procedure to procedure. The report may also indicate the different sizes of toroidal ablation based on vessel size. For example, the smaller the vessel, the smaller the toroidal ablation site should be. If the reported size varies from the expected size, the user may adapt the power or time of ablation based on the vessel size. In some embodiments, the anchor may be configured to measure the vessel size to be included in the treatment report.

Figure 37A:
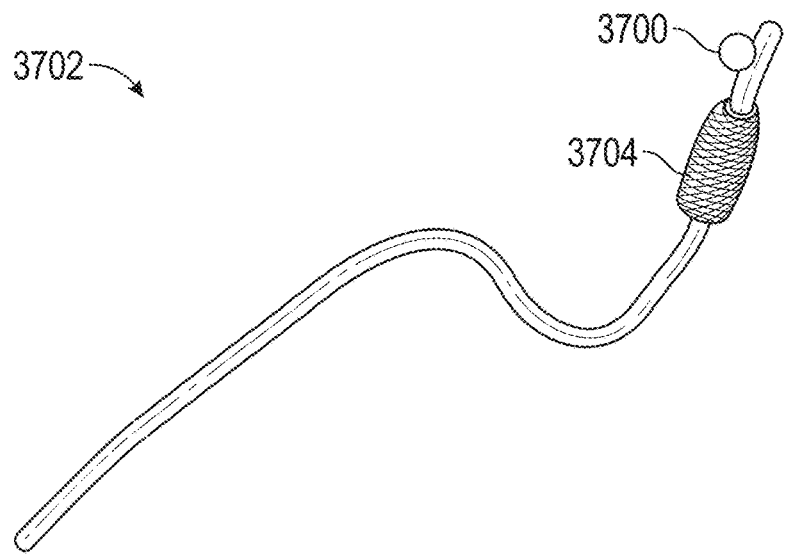
FIG. 37A illustrates an exemplary catheter comprising a sensor constructed in accordance with the principles of the present disclosure.

Sensors (e.g., sensor 3700) may be used to monitor different values during ablation. FIG. 37A illustrates an example catheter 3702 comprising a sensor 3700 located on a distal portion of a catheter 3702. The sensor 3700 may be positioned distal to the transducer 3704, as shown, proximal to the transducer 3704, or in any other suitable configuration. The sensor 3700 may be configured to monitor temperature to track safety and efficiency of the ablation procedure.

Figure 37B:
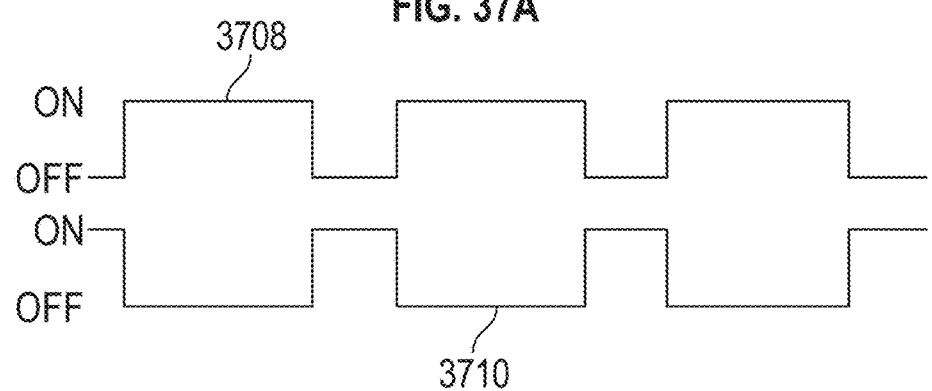
FIG. 37B is a graph depicting example temperature measurement and pulse emission during ablation.

FIG. 37B is a graph depicting temperature measurement 3710 and pulse emission 3708 during ablation. As shown in FIG. 37B, the temperature measurement 3710 should be consistent while ablating. The pulse emission 3708 should also be consistent during ablation. The sensor may be configured to indicate if there is a change in temperature or an unexpected temperature. For example, a temperature that is too high may indicate that there is something wrong and that the procedure should be stopped. The temperature measurement samples in between two pulse emissions 3708 may work around the viscous heating effect of the thermocouple measurement while the thermocouple is located inside the ultrasound beam. This viscous heating effect can be an artifact that rises the temperature value and could lead to wrong measurement. The sensor 3700 may also be configured to measure other values such as blood pressure, flow rate, heart rate, and/or any measurement that may be relevant to the procedure or safety of the patient. Any measurements taken, such as blood pressure, may be used to synchronize the ultrasound emission with the measurement taken.

In some embodiments, the transducer assembly could be used to measure the efficiency by measuring a returned signal during the neuromodulation. For example, during a pulse emission, some energy is reflected back to the transducer when the ultrasound wave travels through an interface between media. When tissue heats, the characteristic of that medium changes, and the change in the energy reflected back from an interface including that medium can be detected using the transducer as a sensor. The reflected energy may change the impedance of the transducer assembly, which can induce a modification of the reflected power returned back to the generator. The reflected power signal analysis can be used to detect a threshold when the pulse starts to be efficient enough, for example, to ablate the tissue. This information could be used to stop the pulse emission when the heating is sufficient for the nerve denaturation. In some embodiments, a multielement ultrasound probe having a cylindrical shape could be added to the system, separate from the transducer used for the neuromodulation, to perform ultrasound thermometry from the inside of the lumen and inform on the procedure efficacy.

Figure 37C:
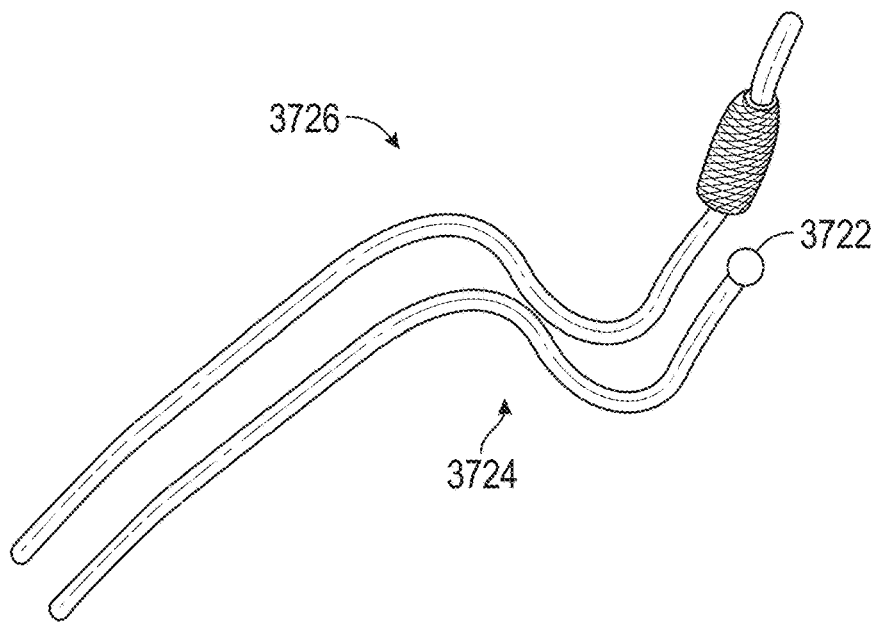
FIG. 37C illustrates an exemplary catheter system including a second catheter comprising a sensor constructed in accordance with the principles of the present disclosure.

FIG. 37C illustrates an example catheter system including a second catheter 3724 embodiment comprising a sensor 3722. The second catheter 3724 is separate from the catheter 3726 comprising the transducer. The sensor 3722 being on a second catheter 3724 can increase the flexibility of where measurements may be taken. For example, the second catheter 3724 may be positioned in a different vessel than the first catheter 3726 or in a different location within the same vessel as the first catheter 3726. In some embodiments, the first catheter 3726 may comprise a lumen (e.g., having an exit port proximal to the transducer) to help guide the second catheter 3724 proximate to its intended position.

Figure 37D:
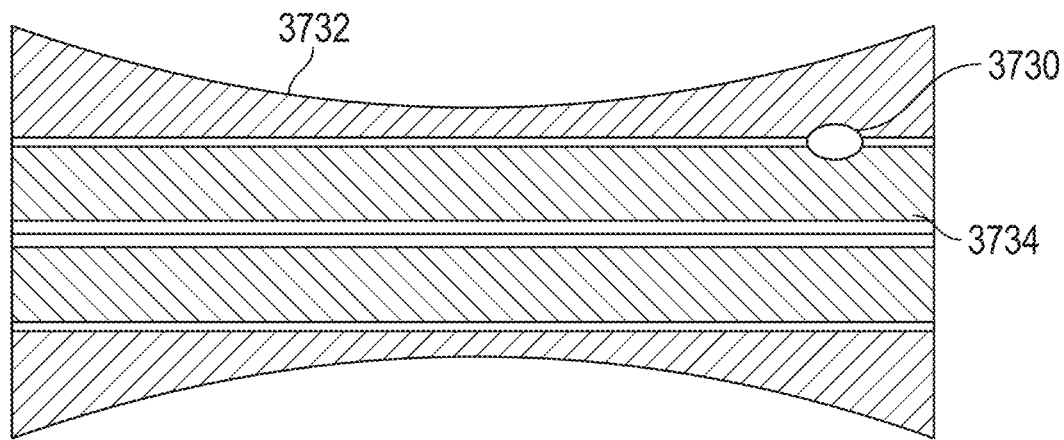
FIG. 37D illustrates a sensor coupled to the interior of an exemplary lens.

FIG. 37D illustrates a sensor 3730 coupled to the interior of a lens 3732. The sensor 3730 is configured to measure the lens temperature. The sensor 3730 may be a thermocouple sensor. This temperature may be monitored to inhibit or prevent overheating of the transducer 3734 to protect the transducer 3734 from being damaged. The temperature of the lens 3732 may be monitored because a lens that has too high a temperature may create clots in a patient.

Figure 37E:
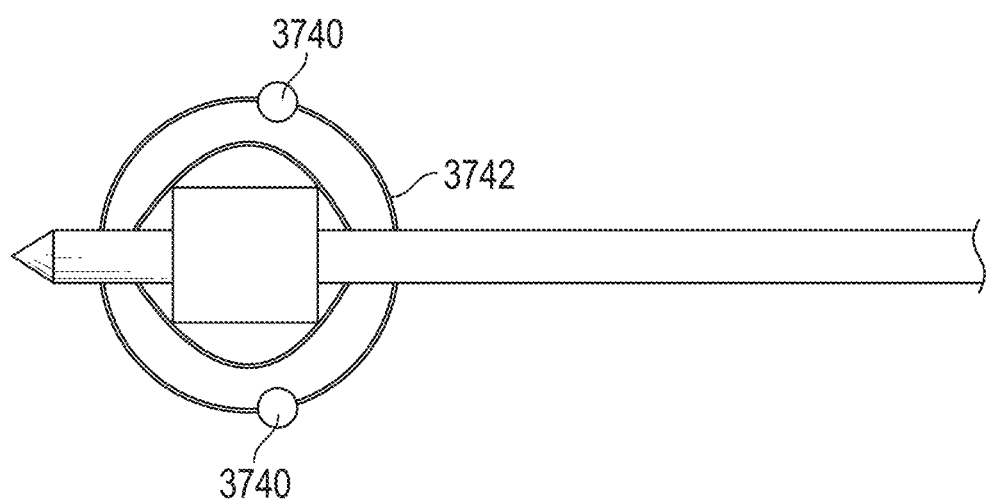
FIG. 37E illustrates a plurality of sensors located on an exemplary anchor in accordance with the principles of the present disclosure.

FIG. 37E illustrates a plurality of sensors 3740 located on an anchor 3742. The sensors 3740 may be thermocouple sensors. One sensor 3740 may be used. In some embodiments, one, some, or all of the struts or other components (e.g., petals) comprises a sensor 3740. In some embodiments, some struts comprise a sensor 3740. The sensors 3740 may be used to measure the temperature next to a vessel wall.

Figure 38A:
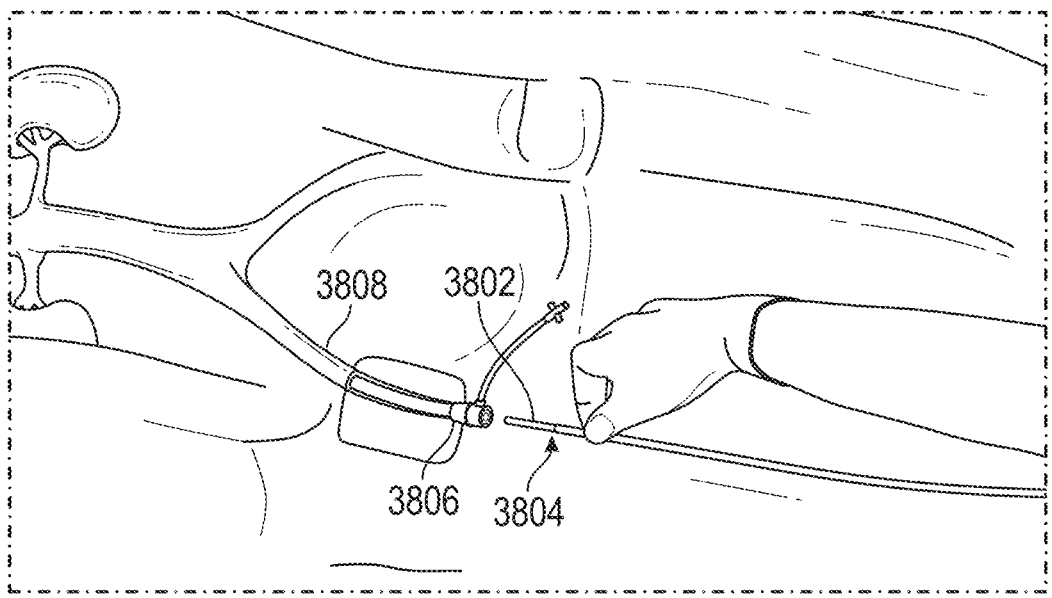
FIGS. 38A-38B illustrate an exemplary method of inserting and navigating a catheter to a vessel in accordance with the principles of the present disclosure.
Figure 38B:
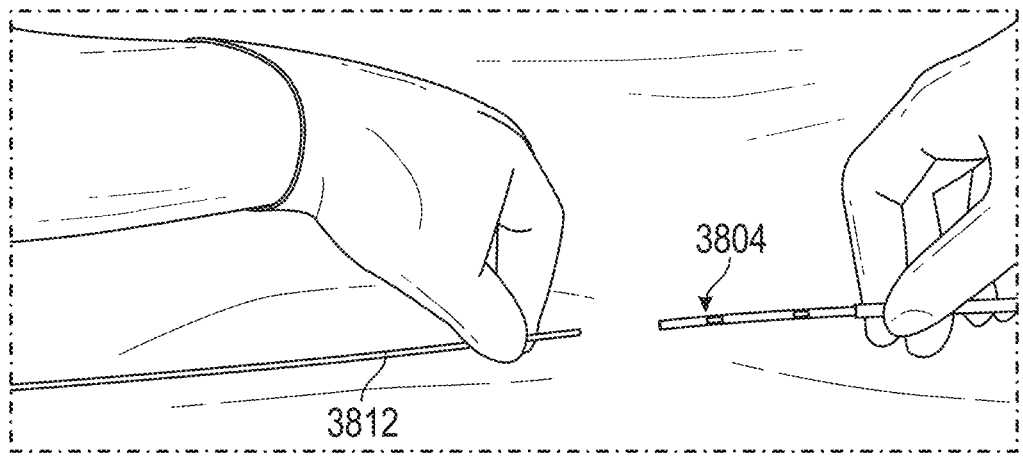

Ablation using any embodiment of the device described herein may occur at multiple ablation sites using a collapse and deploy method. FIG. 38A illustrates the positioning of a first catheter 3804 in a vein 3808 at an insertion site or vein access point 3806. The first catheter 3804 may comprise a balloon 3802. The first catheter 3804 may be positioned in the vein 3808, and the balloon 3802 may then be inflated. The inflated balloon 3802 may then be carried by blood in the venous vasculature, through the right heart, and to a first pulmonary artery. A guidewire 3812 may then be navigated to the first pulmonary artery and the first catheter 3804 may be removed, and described above with regard to step 704 of method 700. FIG. 38B illustrates a treatment catheter 3804 being positioned over the guidewire 3812. The treatment catheter 3804 is tracked over the guidewire 3812 to the first pulmonary artery, and described above with regard to step 710 of method 700. The treatment catheter 3804 may be any of the previously described embodiments.

Figure 38C:
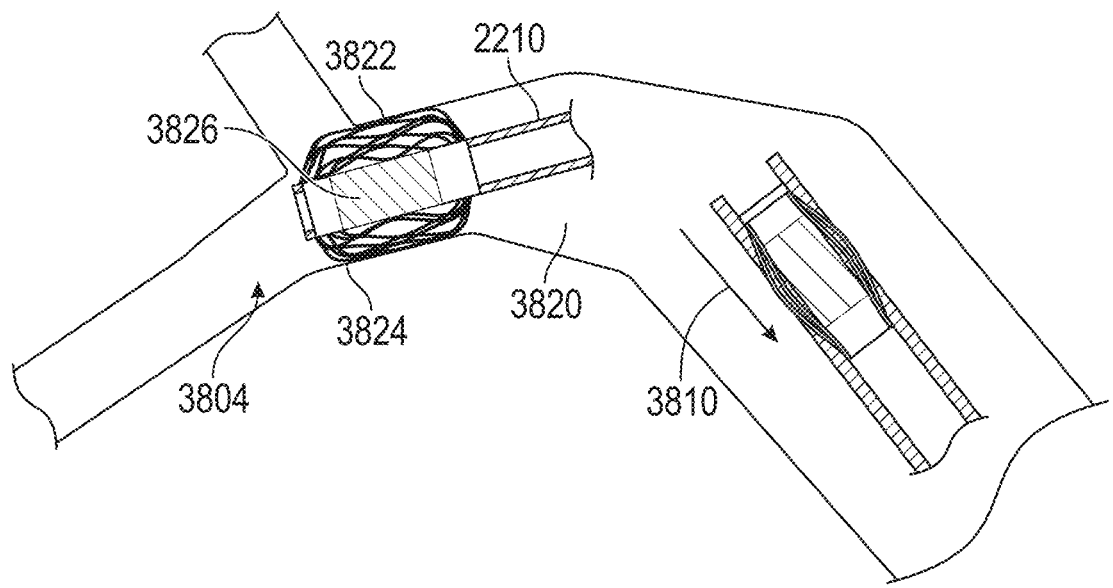
FIGS. 38C-38D illustrate an exemplary method of treating tissue around the right pulmonary artery in accordance with the principles of the present disclosure.

FIG. 38C illustrates the distal portion of the shaft of the treatment catheter 3804 being positioned within the right pulmonary artery (RPA) 3820. The anchor 3822 has been positioned and deployed, according to any of the methods described herein, e.g., step 712 of method 700, within the RPA 3820 at a first ablation site. The anchor 3822 anchors the transducer 3826 within the RPA 3820. The anchor 3822 deploys to contact the artery wall 3824 applying a radial force. After deploying the anchor 3822, the tissue surrounding the first ablation site (e.g., including nerves) is ablated, and described above with regard to step 714 of method 700. Interrupting the nerves around the RPA 3820 can reduce pulmonary hypertension. In some embodiments, neuromodulation is accomplished (e.g., via ablation, denervation, which may or may not be reversible, stimulation, etc.). Ablation may occur at one location during the deployed state, or the transducer 3826 may be translated as described herein to perform multiple ablations during a single deployed anchor position.

An ablation site may be ablated for between about 0.5 seconds and about 1 minute (e.g., about 0.5 seconds, about 1 second, about 5 seconds, about 30 seconds, about 1 minute and ranges between such values). The frequency used during ablation may be between about 1.5 MHz and about 11 MHz (e.g., about 1.5 MHz, about 2 MHz, about 2.5 MHz, about 3.5 MHz, about 4.5 MHz, about 6 MHz, about 7.5 MHz, about 9 MHz, about 11 MHz, and ranges between such values). The acoustic power used during ablation may be between about 20 W and about 80 W (e.g., about 20 W, about 30 W, about 40 W, about 50 W, about 60 W, about 70 W, about 80 W, and ranges between such values). This translates to electric power of between about 25 W and about 160 W and ranges between such values.

Each ablation site may be of a different diameter. As shown in FIGS. 38C to 38I, not all diameters of the pulmonary arteries are the same. The anchor 3822 may be deployable to accommodate the different diameters, as described herein. The locations being ablated may be at different depths or focal points within the vessel walls. The ablation power and time or frequency of the ultrasound beam may be varied to accommodate the varying diameters and depths of the locations to be ablated. In some embodiments, a single set of ablation parameters (e.g., power, duration, frequency) could be used to accommodate various artery diameters. For example, the parameters (e.g., power, duration, frequency) could be set to a target range of lesion depth could be set to exclude tissue where ablation should not occur. In some embodiments, each ablation could include 50 W for one minute followed by 100 W for at least 30 seconds, with optional additional pulses at 100 W for particular locations.

Figure 38D:
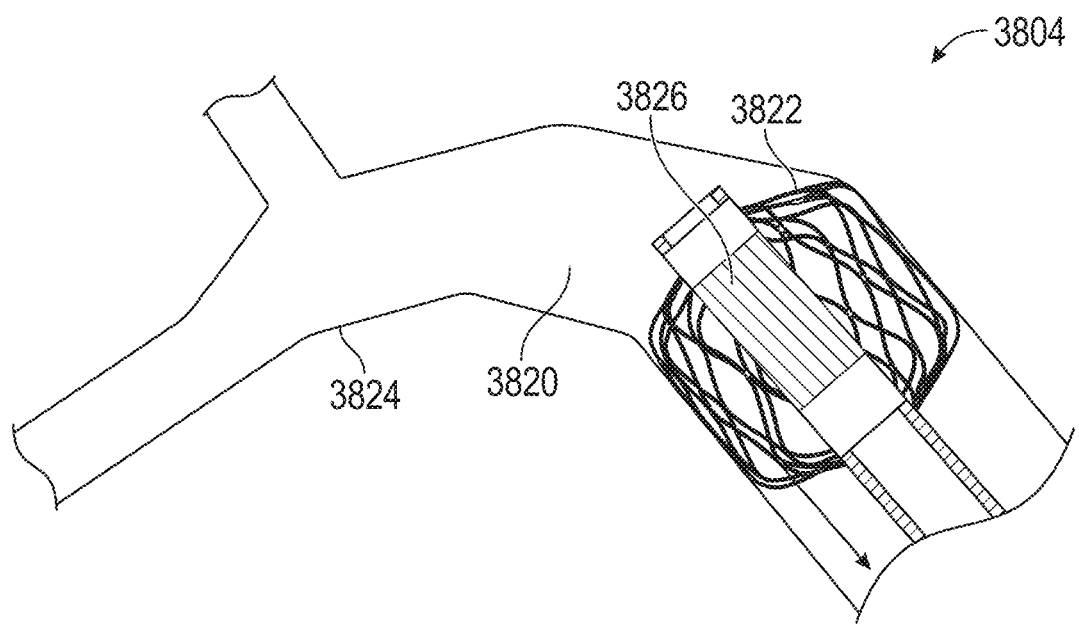

After a first ablation site has been ablated, the anchor 3822 is collapsed by any of the methods described herein, e.g., step 716 of method 700. The distal portion may then be retracted (or advanced) a distance within the RPA 3820, as shown by the arrow 3810 in FIG. 38C, and positioned and deployed at a second ablation site, as shown in FIG. 38D. The deploying, ablating, collapsing, and retracting steps may be repeated until the tissue around the desired amount of the RPA 3820 (e.g., the entire length of the RPA, ¾, ⅔, ½, ⅓, ¼, and ranges between such values) has been covered by the ablation. Because nerves can act like wires where cutting at any point along the length may be sufficient to disable the nerve, smaller lengths or segments of the RPA may be ablated to have a beneficial effect. Because nerves are not necessarily straight, can branch, can start or stop along the length of the RPA, etc. larger lengths may be used to have a beneficial effect. Ablation may be repeated at some or all ablation sites to account for any interference or shadows caused by the anchors, as discussed herein.

Figure 38E:
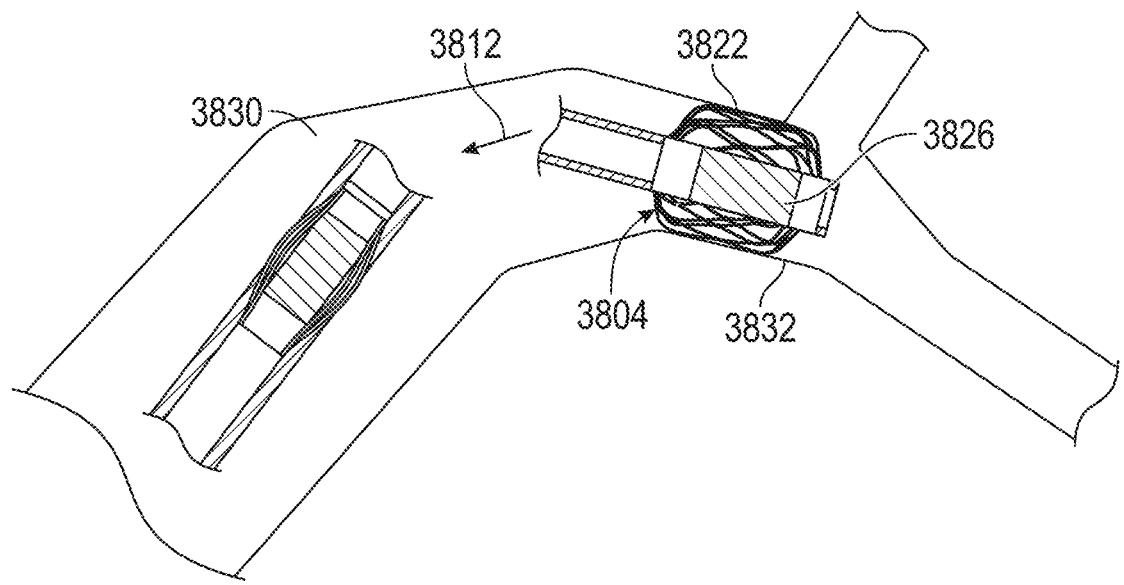
FIGS. 38E-38F illustrate an exemplary method of treating tissue around the left pulmonary artery in accordance with the principles of the present disclosure.

FIG. 38E illustrates the distal portion of the shaft of the treatment catheter 3804 positioned within the left pulmonary artery (LPA) 3830. The anchor 3822 is positioned and deployed, according to any of the above described methods, within the LPA 3830 at a first ablation site. The anchor 3822 anchors the transducer 3826 within the LPA 3830. The anchor 3822 deploys to contact the artery wall 3832 applying a radial force. After deploying the anchor 3822, the tissue surrounding the first ablation site (e.g., including nerves) is ablated. Interrupting the nerves around the LPA 3822 can reduce pulmonary hypertension. Ablation may occur at one location during the deployed state, or the transducer 3826 may be translated as described herein to perform multiple ablations during a single deployed anchor position.

Figure 38F:
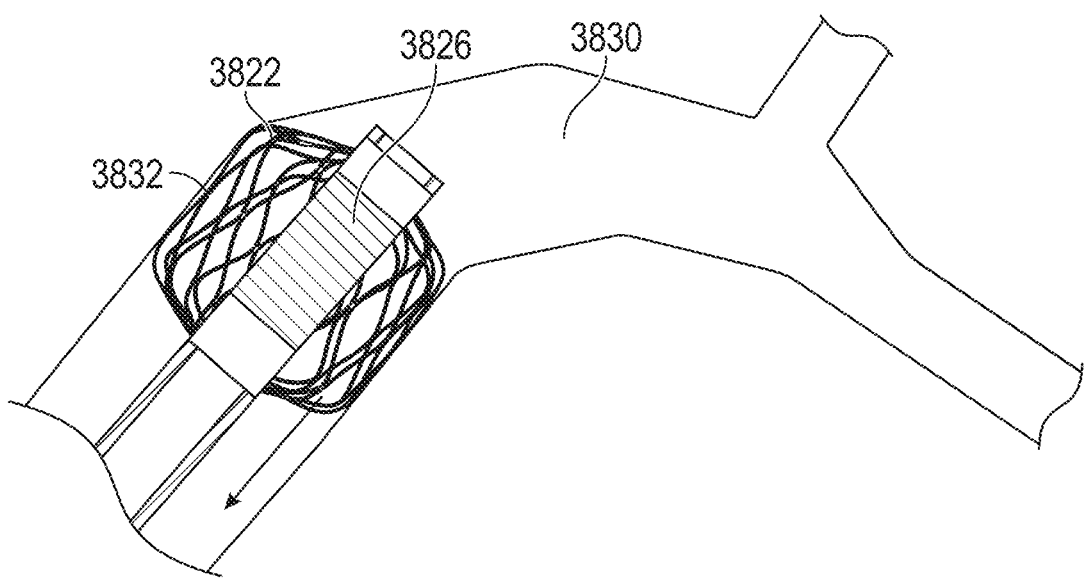

Once the first ablation site has been ablated, the anchor 3822 may be collapsed by any of the methods described herein. The distal portion may then be retracted (or advanced) a distance within the LPA 3830, as shown by the arrow 3812 in FIG. 38E, and positioned and deployed at a second ablation site, as shown in FIG. 38F. The deploying, ablating, collapsing, and retracting steps may be repeated until the tissue around the desired amount of the LPA 3830 (e.g., the entire length of the LPA, ¾, ⅔, ½, ⅓, ¼, and ranges between such values) has been covered by the ablation. Because nerves can act like wires where cutting at any point along the length may be sufficient to disable the nerve, smaller lengths or segments of the LPA may be ablated to have a beneficial effect. Because nerves are not necessarily straight, can branch, can start or stop along the length of the LPA, etc. larger lengths may be used to have a beneficial effect. Ablation may be repeated at some or all ablation sites to account for any interference or shadows caused by the anchors, as discussed herein.

Figure 38G:
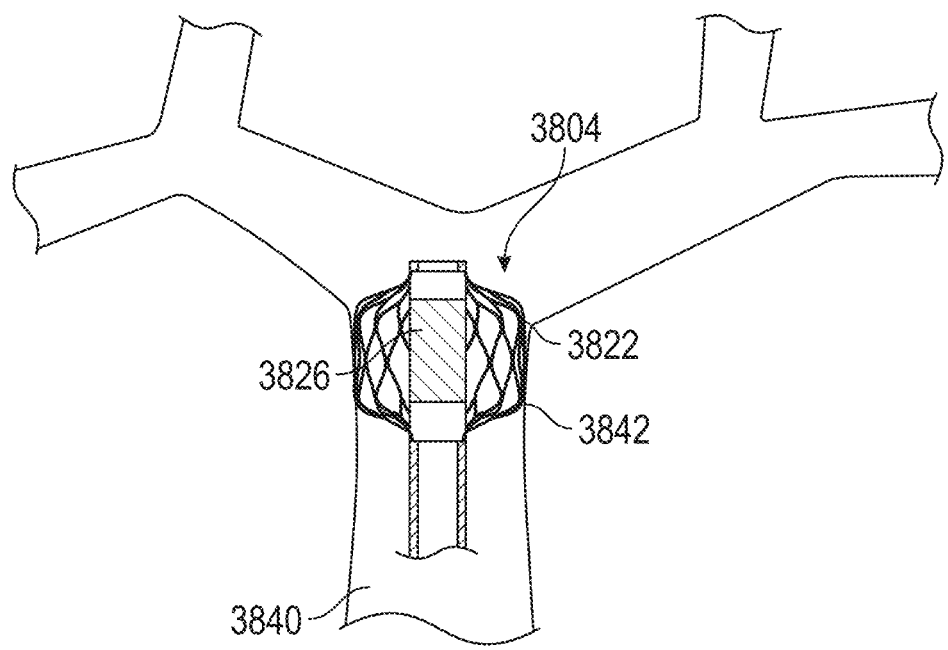
FIGS. 38G-38I illustrate an exemplary method of treating tissue around the pulmonary trunk in accordance with the principles of the present disclosure.
Figure 38H:
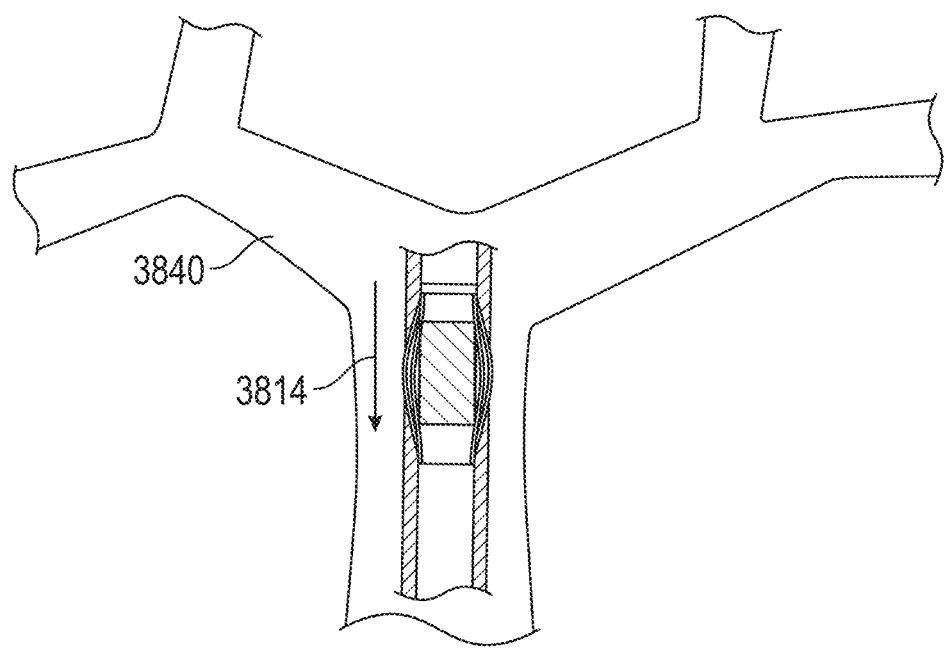
Figure 38I:
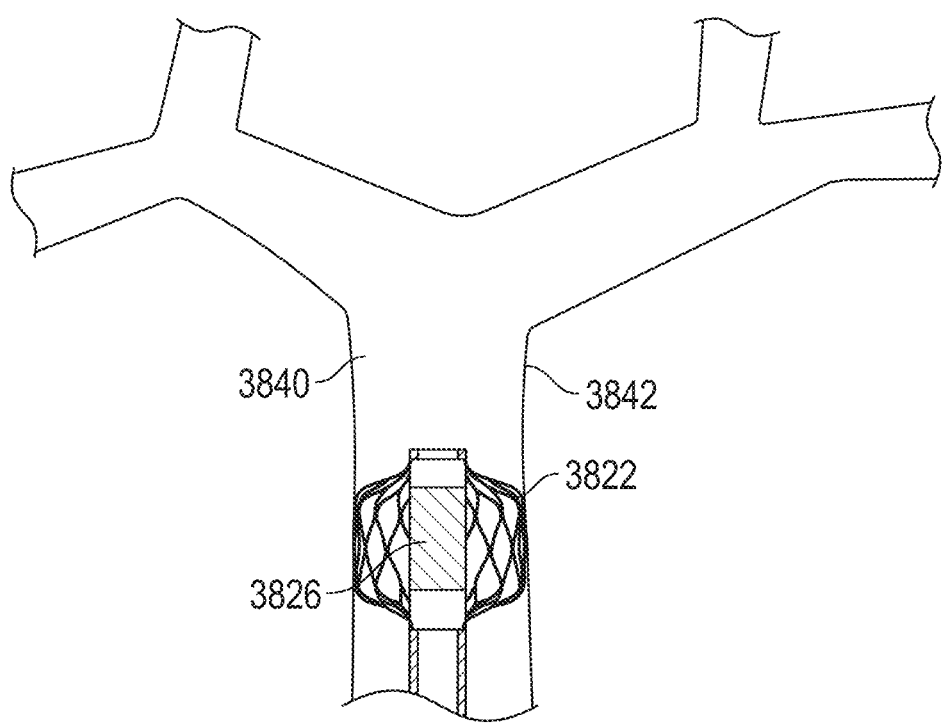

FIG. 38G illustrates a transducer 3826 positioned within a pulmonary trunk 3840 at a first ablation site. The anchor 3822 may be deployed by any of the described methods herein to anchor the transducer 3826 within the pulmonary trunk 3840. The anchor 3822 may be deployed to contact the pulmonary trunk walls 3842 applying a radial force to center the transducer 3826. The first ablation site may be ablated. Interrupting the nerves around the pulmonary trunk 3840 can reduce pulmonary hypertension. The anchor 3822 may be collapsed by any of the methods described herein. The transducer 3826 may then be retracted (or advanced) a distance within the pulmonary trunk 3820, as shown by the arrow 3814 in FIG. 38H, and positioned and deployed at a second ablation site, as shown in FIG. 38I. The second ablation site may be ablated. The deploying, ablating, collapsing, and retracting steps may be repeated until the tissue around the desired amount of the pulmonary trunk 3840 (e.g., the entire length pulmonary trunk, ¾, ⅔, ½, ⅓, ¼, and ranges between such values) has been covered by the ablation. Because nerves can act like wires where cutting at any point along the length may be sufficient to disable the nerve, smaller lengths or segments of the PT may be ablated to have a beneficial effect. Because nerves are not necessarily straight, can branch, can start or stop along the length of the PT, etc. larger lengths may be used to have a beneficial effect. Ablation may occur at one location during the deployed state, or the transducer 3826 may be translated as described herein to perform multiple ablations during a single deployed anchor position. Ablation may be repeated at some or all ablation sites to account for any interference or shadows caused by the anchors, as discussed herein. The treatment catheter may then be removed from the patient.

This method of ablation may be performed in any order. For example, as previously described, the right pulmonary artery (RPA) may be ablated first, followed by the left pulmonary artery (LPA), followed by the pulmonary trunk. Alternatively, the LPA may be ablated first, followed by the RPA, and followed by the pulmonary trunk. Any possible order may be used. If needed, but not necessary, ablation sites may be repeated in each vessel. For example, the pulmonary trunk may be ablated twice and/or either or both of the pulmonary arteries may be ablated twice.

The device used during the ablation method may comprises any of the embodiments described herein. Any of the collapsing and deploying methods described herein may be utilized. The movement features described herein may also be utilized in monitoring the location of the distal portion of the catheter 3804 when retracted or otherwise moved within a vessel.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A method for reducing neural activity of nerves around a blood vessel of a patient, the method comprising:
    measuring first pressure information within the blood vessel;
    applying a first force to an inner wall of the blood vessel to distend the blood vessel;
    measuring second pressure information within the blood vessel while the first force is applied to the inner wall to distend the blood vessel;
    emitting energy via an ablation device positioned within the blood vessel to ablate nerves around the blood vessel;
    applying a second force to the inner wall of the blood vessel to distend the blood vessel;
    measuring third pressure information within the blood vessel while the second force is applied to the inner wall to distend the blood vessel; and
    comparing the second pressure information to the third pressure information to determine whether the emitted energy has reduced neural activity of the nerves around the blood vessel.

2. The method of claim 1, wherein the second pressure information is indicative of a first pressure gradient between pressure within the blood vessel while the first force is applied to the inner wall to distend the blood vessel and pre-distension pressure within the blood vessel associated with the first pressure information, and wherein the third pressure information is indicative of a second pressure gradient between pressure within the blood vessel while the second force is applied to the inner wall to distend the blood vessel and pre-distension pressure within the blood vessel associated with the first pressure information.

3. The method of claim 2, wherein the emitted energy has reduced neural activity of the nerves around the blood vessel if the comparison of the second and third pressure information indicates that the second pressure gradient is less than the first pressure gradient by more than a predetermined threshold.

4. The method of claim 2, wherein the emitted energy has reduced neural activity of the nerves around the blood vessel if the second pressure gradient is zero.

5. The method of claim 1, wherein applying the first and second force to the inner wall of the blood vessel to distend the blood vessel comprises applying a force sufficient to stimulate baroreceptors within the blood vessel.

6. The method of claim 1, wherein applying at least one of the first or second force to the inner wall of the blood vessel to distend the blood vessel comprises expanding an expandable member from a collapsed state to an expanded state, the expandable member disposed on a catheter sized and shaped to be positioned within the blood vessel.

7. The method of claim 6, wherein, in the expanded state, the expandable member does not fully occlude blood through the blood vessel.

8. The method of claim 6, wherein the ablation device is disposed on the same catheter.

9. The method of claim 6, wherein the ablation device is disposed on a second catheter sized and shaped to be positioned within the vessel, the second catheter different from the catheter.

10. The method of claim 1, wherein applying at least one of the first or second force to the inner wall of the blood vessel to distend the blood vessel comprises applying a torque to a catheter shaft to bend the catheter shaft within the blood vessel to apply the force.

11. The method of claim 1, wherein, if the emitted energy has not reduced neural activity of the nerves around the blood vessel based on the comparison of the second and third pressure information, the method further comprises:
    emitting energy via the ablation device positioned within the blood vessel to ablate nerves around the blood vessel;
    applying a third force to the inner wall of the blood vessel to distend the blood vessel;
    measuring fourth pressure information within the blood vessel while the third force is applied to the inner wall to distend the blood vessel; and
    comparing the fourth pressure information to at least one of the second or third pressure information to determine whether the emitted energy has reduced neural activity of the nerves around the blood vessel.

12. The method of claim 1, wherein emitting energy via the ablation device positioned within the blood vessel to ablate nerves around the blood vessel comprises emitting at least one of focused ultrasound, unfocused ultrasound, radio frequency, microwave, cryo energy, laser, or pulsed field electroporation.

13. The method of claim 1, wherein emitting energy via the ablation device positioned within the blood vessel to ablate nerves around the blood vessel comprises emitting ultrasound.

14. The method of claim 1, wherein the blood vessel is a pulmonary artery, and wherein emitting energy via the ablation device within the blood vessel reduces neural activity of nerves around the pulmonary artery to treat pulmonary hypertension.

15. The method of claim 1, wherein emitting energy via the ablation device positioned within the blood vessel to ablate nerves around the blood vessel comprises emitting energy via the ablation device in accordance with a predetermined actuation regime, the predetermined actuation regime comprising predetermined periods of non-ablation between predetermined periods of ablation.

16. The method of claim 1, further comprising deploying an expandable anchor within the vessel to centralize the ablation device within the blood vessel.

17. The method of claim 16, wherein a first end of the expandable anchor is coupled to a first catheter and a second end of the expandable anchor is coupled to a second catheter slidably disposed over the first catheter, and wherein deploying the expandable anchor comprises moving the first catheter relative to the second catheter to cause the expandable anchor to transition from a collapsed state to an expanded state.

18. The method of claim 17, wherein blood flow is permitted across the expandable anchor in the expanded state.

19. A system for reducing neural activity of nerves around a blood vessel of a patient, the system comprising:
    a catheter assembly comprising a proximal region operatively coupled to a handle and a distal region sized and shaped to be positioned within the blood vessel, the distal region of the catheter assembly comprising an ablation device configured to be actuated to emit energy within the blood vessel to reduce neural activity of nerves around the blood vessel;
    a distension mechanism configured to apply a force to an inner wall of the blood vessel sufficient to distend the blood vessel and stimulate baroreceptors within the blood vessel;
    one or more sensors configured to measure pressure within the blood vessel; and a controller operatively coupled to the one or more sensors, the controller programmed to:
  receive first pressure information within the blood vessel from the one or more sensors at a first time;
  receive second pressure information within the blood vessel from the one or more sensors at a second time while the distension mechanism applies a first force to the inner wall to distend the blood vessel;
  receive third pressure information within the blood vessel from the one or more sensors at a third time after energy is emitted within the blood vessel via the ablation device to reduce neural activity of nerves around the blood vessel and while the distension mechanism applies a second force to the inner wall to distend the blood vessel; and
  compare the second pressure information to the third pressure information to determine whether the energy has reduced neural activity of the nerves around the blood vessel.

20. The system of claim 19, wherein the distension mechanism comprises an expandable member configured to be expanded from a collapsed state to an expanded state to apply the force to the inner wall of the blood vessel.

21. The system of claim 19, wherein the distension mechanism comprises a torqueing mechanism configured to bend a shaft of the catheter assembly within the blood vessel to apply the force to the inner wall of the blood vessel.

22. The system of claim 19, wherein the second pressure information is indicative of a first pressure gradient between pressure within the blood vessel while the first force is applied to the inner wall to distend the blood vessel and pre-distension pressure within the blood vessel associated with the first pressure information, and wherein the third pressure information is indicative of a second pressure gradient between pressure within the blood vessel while the second force is applied to the inner wall to distend the blood vessel and pre-distension pressure within the blood vessel associated with the first pressure information.

23. The system of claim 19, wherein the energy has reduced neural activity of the nerves around the blood vessel if the comparison of the second and third pressure information indicates that the second pressure gradient is less than the first pressure gradient by more than a predetermined threshold.

24. The system of claim 19, further comprising an expandable anchor configured to transition between a collapsed delivery state and an expanded deployed state where the expandable anchor centralizes the ablation device within the blood vessel.

25. The system of claim 19, wherein the ablation device is configured to emit at least one of focused ultrasound, unfocused ultrasound, radio frequency, microwave, cryo energy, laser, or pulsed field electroporation.

26. The system of claim 19, wherein the ablation device is configured to emit ultrasound.

27. The system of claim 19, wherein the distension mechanism is disposed on the catheter assembly.

28. The system of claim 19, further comprising:
  a second catheter assembly separate from the catheter assembly,
  wherein the distension mechanism is disposed on the second catheter assembly.

29. The system of claim 19, wherein the catheter assembly comprises:
  an inner catheter comprising a guidewire lumen extending through at least a portion of a length of the inner catheter;
  a transducer shaft comprising a lumen sized and shaped to slidably receive the inner catheter therein, wherein the ablation device is disposed on the transducer shaft;
  an outer catheter comprising a lumen sized and shaped to receive the transducer shaft therein;
  an expandable anchor comprising a distal end coupled to the inner catheter and a proximal end coupled to the outer catheter such that relative movement between the inner catheter and the outer catheter causes the expandable anchor to transition between a collapsed delivery state and an expanded deployed state, the expandable anchor configured to centralize the ablation device within the blood vessel of the patient in the expanded deployed state; and
  a sheath comprising a lumen sized and shaped to slidably receive the outer catheter and the expandable anchor in the collapsed delivery state therein.

30. The system of claim 29, wherein a distal region of the sheath has a stiffness sufficient to facilitate transitioning of the expandable anchor from the expanded deployed state to the collapsed delivery state upon movement of the distal region of the sheath relative to the expandable anchor without buckling the distal region of the sheath.

* * * * *